US011038111B2

(12) United States Patent
Takada et al.

(10) Patent No.: US 11,038,111 B2
(45) Date of Patent: Jun. 15, 2021

(54) ORGANIC ELECTROLUMINESCENCE DEVICE AND MONOAMINE COMPOUND FOR ORGANIC ELECTROLUMINESCENCE DEVICE

(71) Applicant: Samsung Display Co., Ltd., Yongin-si (KR)

(72) Inventors: Ichinori Takada, Tsurumi-ku (JP); Ichiro Imada, Tsurumi-ku (JP)

(73) Assignee: Samsung Display Co., Ltd., Yongin-si (KR)

( * ) Notice: Subject to any disclaimer, the term of this patent is extended or adjusted under 35 U.S.C. 154(b) by 397 days.

(21) Appl. No.: 16/200,412

(22) Filed: Nov. 26, 2018

(65) Prior Publication Data

US 2019/0165273 A1 May 30, 2019

(30) Foreign Application Priority Data

Nov. 28, 2017 (KR) .................. 10-2017-0160887
Aug. 13, 2018 (KR) .................. 10-2018-0094264

(51) Int. Cl.
*H01L 51/50* (2006.01)
*H01L 51/00* (2006.01)
(Continued)

(52) U.S. Cl.
CPC .......... *H01L 51/006* (2013.01); *C07C 211/54* (2013.01); *C07D 307/91* (2013.01);
(Continued)

(58) Field of Classification Search
None
See application file for complete search history.

(56) References Cited

U.S. PATENT DOCUMENTS 9,412,964 B2    8/2016  Sotoyama et al.
9,768,391 B2    9/2017  Mujica-Fernaud et al.
(Continued)

FOREIGN PATENT DOCUMENTS

JP    2002-270374 A    9/2002
JP    2007-238760 A    9/2007
(Continued)

OTHER PUBLICATIONS

Archibald, T.G. et al.; "Thermally Stable Acetylenic Adamantane Polymers"; Macromolecules; 1991; 24; pp. 5261-5265.
(Continued)

*Primary Examiner* — Gregory D Clark
(74) *Attorney, Agent, or Firm* — Lewis Roca Rothgerber Christie LLP

(57) ABSTRACT

An organic electroluminescence device includes a first electrode and a second electrode which are positioned facing each other, and at least one organic layer between the first electrode and the second electrode, wherein the at least one organic layer includes a monoamine compound which is represented by Formula 1 and includes at least one adamantyl group as a substituent, thereby achieving improved device efficiency:

$$Ar_3-N{\overset{Ar_1}{\underset{Ar_2}{\diagdown}}}\quad\text{Formula 1}$$

22 Claims, 2 Drawing Sheets

(51) Int. Cl.
*C09K 11/06* (2006.01)
*C07D 307/91* (2006.01)
*C07D 333/76* (2006.01)
*C07C 211/54* (2006.01)
*C07F 7/08* (2006.01)

(52) U.S. Cl.
CPC .......... *C07D 333/76* (2013.01); *C07F 7/081* (2013.01); *C09K 11/06* (2013.01); *H01L 51/0061* (2013.01); *C07C 2603/26* (2017.05); *C07C 2603/74* (2017.05); *C09K 2211/1007* (2013.01); *C09K 2211/1011* (2013.01); *C09K 2211/1014* (2013.01); *C09K 2211/1018* (2013.01); *H01L 51/0052* (2013.01); *H01L 51/0073* (2013.01); *H01L 51/0074* (2013.01); *H01L 51/5012* (2013.01); *H01L 51/5016* (2013.01); *H01L 51/5056* (2013.01); *H01L 51/5088* (2013.01); *H01L 51/5096* (2013.01)

(56) References Cited

U.S. PATENT DOCUMENTS

| | | |
|---|---|---|
| 9,812,652 B2 | 11/2017 | Arai et al. |
| 9,972,787 B2 | 5/2018 | Miyake et al. |
| 2017/0179398 A1 | 6/2017 | Yokoyama et al. |

FOREIGN PATENT DOCUMENTS

| | | | |
|---|---|---|---|
| JP | 4189719 B2 | 9/2008 | |
| JP | 5609256 B2 | 9/2014 | |
| KR | 10-2016-0032020 A | 3/2016 | |
| KR | 10-1708176 B1 | 2/2017 | |
| KR | 2017116168 * | 7/2017 | ............ H01I 51/50 |
| KR | 10-1772990 B1 | 9/2017 | |
| KR | 10-1790321 B1 | 10/2017 | |
| WO | WO 2016/006629 A1 | 1/2016 | |

OTHER PUBLICATIONS

Gu, Yu et al.; "Tetrasubstituted adamantane derivatives with arylamine groups: Solution-processable hole-transporting and host materials with high triplet energy and good thermal stability for organic light-emitting devices"; Organic Electronics; 25; 2015; pp. 193-199.

Hala, Slavoj et al.; "Oxidation and Thermal Stability of Adamantane Ester Oils"; Technologie Paliv; 1978; 39; pp. 225-243, English lang. summary pp. 242-243.

Zhang, Kai et al.; "A thermally and electrochemically stable organic hole-transporting material with an adamantane central core and triarylamine moieties"; Synthetic Metals; 162; 2012; pp. 490-496.

\* cited by examiner

ORGANIC ELECTROLUMINESCENCE DEVICE AND MONOAMINE COMPOUND FOR ORGANIC ELECTROLUMINESCENCE DEVICE

CROSS-REFERENCE TO RELATED APPLICATION

This application claims priority to and the benefit of Korean Patent Application Nos. 10-2017-0160887, filed on Nov. 28, 2017 and 10-2018-0094264, filed on Aug. 13, 2018, the entire content of each of which is hereby incorporated by reference.

BACKGROUND

One or more aspects of embodiments of the present disclosure are directed toward a monoamine compound and an organic electroluminescence device including the same, and more particularly, to a monoamine compound used in a hole transport region and an organic electroluminescence device including the same.

Recently, the development of an organic electroluminescence display device as an image display device is being actively conducted. Different from a liquid crystal display device, the organic electroluminescence display device is a self-luminescent display device in which holes and electrons injected from a first electrode and a second electrode recombine in an emission layer, and a light emission material including an organic compound in the emission layer emits light to realize the display of images.

In the application of an organic electroluminescence device to a display device, the decrease of the driving voltage, and the increase of the light emission efficiency and the life of the organic electroluminescence device are required (or desired), and developments of materials for an organic electroluminescence device capable of stably attaining the aforementioned characteristics are needed.

In addition, in order to achieve an organic electroluminescence device with high efficiency, development of a material for a hole transport layer capable of restraining the diffusion, etc. of the exciton energy of an emission layer is being conducted.

SUMMARY

One or more aspects of embodiments of the present disclosure are directed toward a monoamine compound as a material for an organic electroluminescence device capable of improving light emission efficiency.

One or more aspects of embodiments of the present disclosure are also directed toward an organic electroluminescence device including the monoamine compound and having improved light emission efficiency.

An embodiment of the inventive concept provides an organic electroluminescence device including a first electrode, a second electrode on the first electrode, and a plurality of organic layers between the first electrode and the second electrode, wherein at least one organic layer among the plurality of organic layers includes a monoamine compound represented by the following Formula 1:

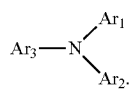

Formula 1

In Formula 1, at least one selected from $Ar_1$, $Ar_2$ and $Ar_3$ is represented by the following Formula 2, and the remaining ones of $Ar_1$, $Ar_2$ and $Ar_3$ are each independently a substituted or unsubstituted aryl group having 6 to 30 carbon atoms for forming a ring, or a substituted or unsubstituted heteroaryl group having 2 to 30 carbon atoms for forming a ring:

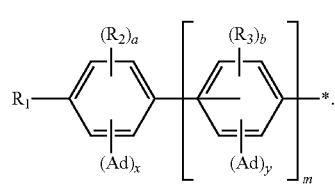

Formula 2

In Formula 2, $R_1$ to $R_3$ are each independently a hydrogen atom, a deuterium atom, a halogen atom, a cyano group, a substituted or unsubstituted silyl group, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring; "m" is 0 or 1; "a", "b", "x" and "y" are each independently an integer of 0 to 4, where if "m" is 0, "x" is an integer of 1 or more, and if "m" is 1, "x+y" is an integer of 1 or more; and "Ad" is represented by the following Formula 3:

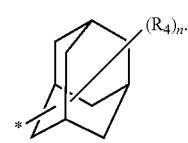

Formula 3

In Formula 3, $R_4$ is a hydrogen atom, a deuterium atom, a halogen atom, a cyano group, a substituted or unsubstituted silyl group, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring; and "n" is an integer of 0 to 15.

In an embodiment, the plurality of organic layers may include an emission layer, and a hole transport region between the first electrode and the emission layer, wherein the hole transport region may include the monoamine compound represented by Formula 1.

In an embodiment, the plurality of organic layers may include an emission layer, a hole injection layer between the first electrode and the emission layer, and a hole transport layer between the hole injection layer and the emission layer, wherein the hole transport layer may include the monoamine compound represented by Formula 1.

In an embodiment, Formula 3 may be represented by the following Formula 3-1 or Formula 3-2:

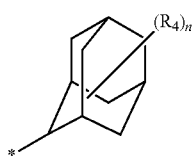

Formula 3-1

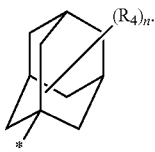
Formula 3-2

In Formula 3-1 and Formula 3-2, $R_4$ and "n" are the same as defined in Formula 3.

In an embodiment, Formula 1 may be represented by the following Formula 1-A or Formula 1-B:

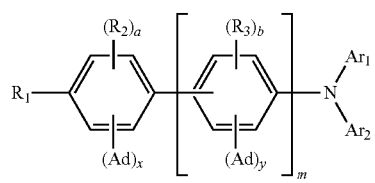
Formula 1-A

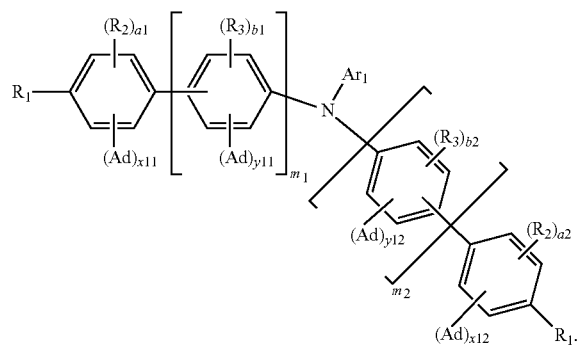
Formula 1-B

In Formula 1-B, "m1" and "m2" are each independently 0 or 1, and "a1", "a2", "b1", "b2", "x11", "x12", "y11", and "y12" are each independently an integer of 0 to 4, where if "m1" is 0, "x11" is an integer of 1 or more, if "m1" is 1, "x11+y11" is an integer of 1 or more, if "m2" is 0, "x12" is an integer of 1 or more, and if "m2" is 1, "x12+y12" is an integer of 1 or more.

In Formula 1-A and Formula 1-B, $Ar_1$ and $Ar_2$ are the same as defined in Formula 1, $R_1$ to $R_3$, "a", "b", "x", "y", and "Ad" are the same as defined in Formula 2.

In an embodiment, Formula 1-A may be represented by any one among the following Formula 1-1 to Formula 1-3:

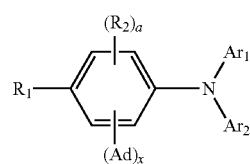
Formula 1-1

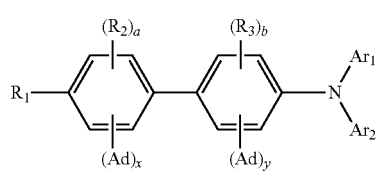
Formula 1-2

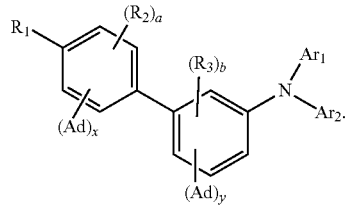
Formula 1-3

In Formula 1-1 to Formula 1-3, $Ar_1$ and $Ar_2$ are the same as defined in Formula 1, and $R_1$ to $R_3$, "a", "b", "x", "y", and "Ad" are the same as defined in Formula 2.

In an embodiment, $Ar_1$ and $Ar_2$ may be each independently a substituted or unsubstituted phenyl group, a substituted or unsubstituted biphenyl group, a substituted or unsubstituted terphenyl group, a substituted or unsubstituted phenanthryl group, a substituted or unsubstituted dibenzofuran group, or a substituted or unsubstituted dibenzothiophene group.

In an embodiment, $Ar_1$ and $Ar_2$ may be each independently an aryl group having 6 to 30 carbon atoms for forming a ring, wherein the aryl group is an unsubstituted aryl group or an aryl group substituted with at least one selected from a halogen atom, a cyano group, an alkyl group having 1 to 20 carbon atoms, an alkoxy group having 1 to 10 carbon atoms, an aryloxy group having 1 to 20 carbon atoms, an alkylthio group having 1 to 10 carbon atoms, an arylthio group having 1 to 20 carbon atoms, a triarylsilyl group having 18 to 50 carbon atoms, and an adamantyl group.

In an embodiment, $Ar_1$ and $Ar_2$ may be each independently a heteroaryl group having 2 to 30 carbon atoms for forming a ring, wherein the heteroaryl group is an unsubstituted heteroaryl group or a heteroaryl group substituted with at least one selected from a halogen atom, a cyano group, an alkyl group having 1 to 20 carbon atoms, an alkoxy group having 1 to 10 carbon atoms, an aryloxy group having 1 to 20 carbon atoms, an alkylthio group having 1 to 10 carbon atoms, an arylthio group having 1 to 20 carbon atoms, a triarylsilyl group having 18 to 50 carbon atoms, and an adamantyl group.

In an embodiment, $Ar_1$ and $Ar_2$ may be each independently represented by any one among the following Formula A-1 to Formula A-20:

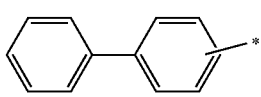
A-1

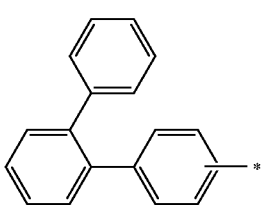
A-2

-continued
A-3
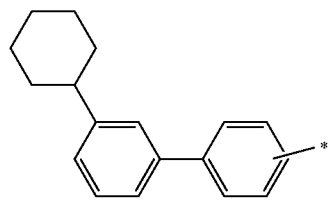
A-4
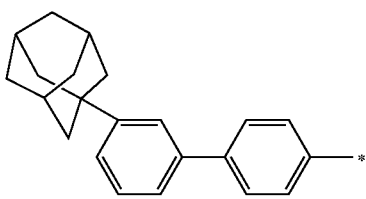
A-5
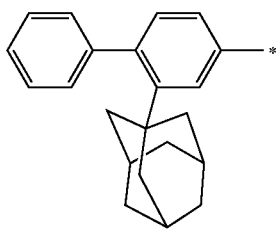
A-6
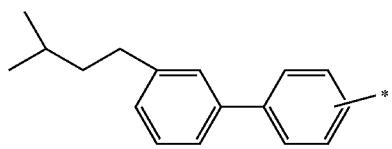
A-7
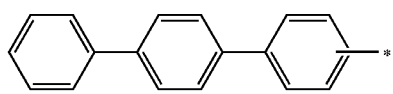
A-8
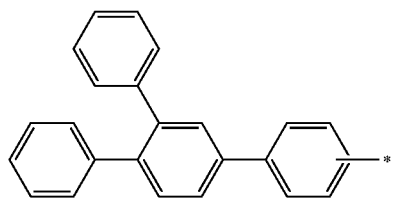
A-9
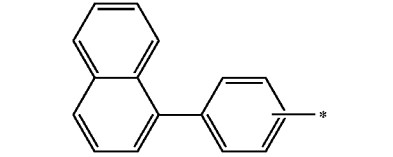
A-10
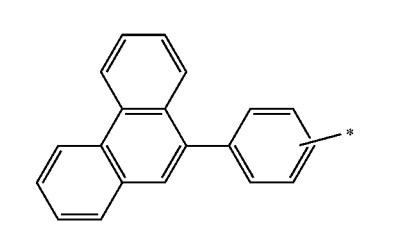
-continued
A-11
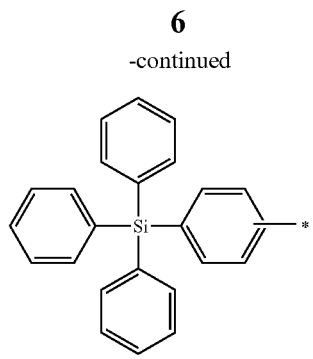
A-12
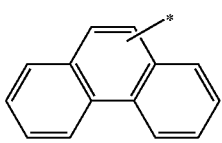
A-13
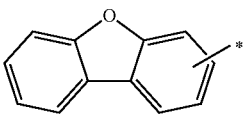
A-14
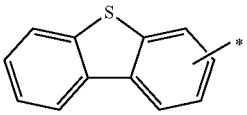
A-15
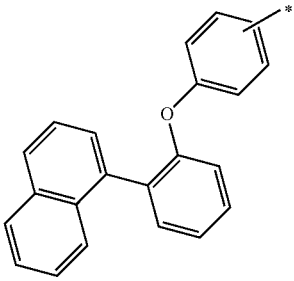
A-16
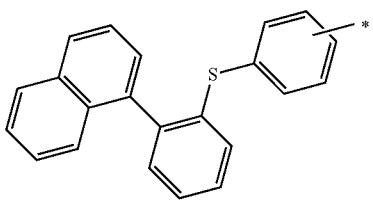
A-17
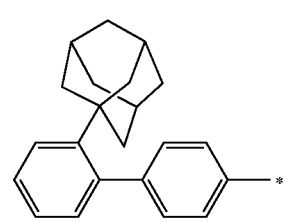
A-18
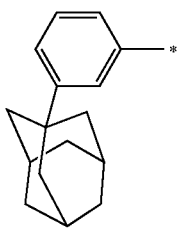

A-19
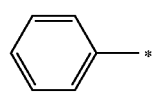
A-20
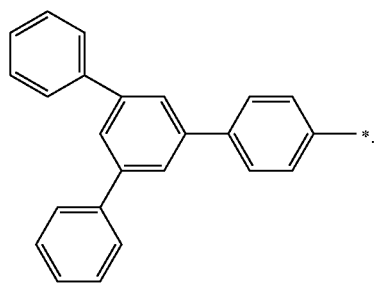
In an embodiment, the monoamine compound may include at least one among the compounds in the following Compound Group 1 and Compound Group 2:
Compound Group 1
1
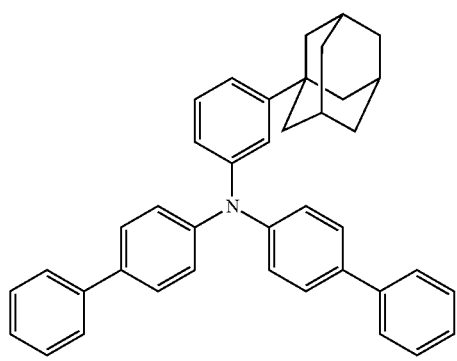
2
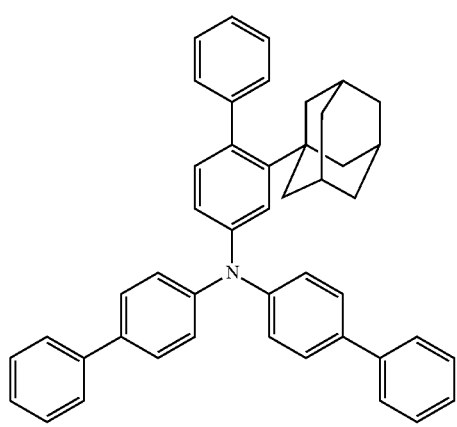
3
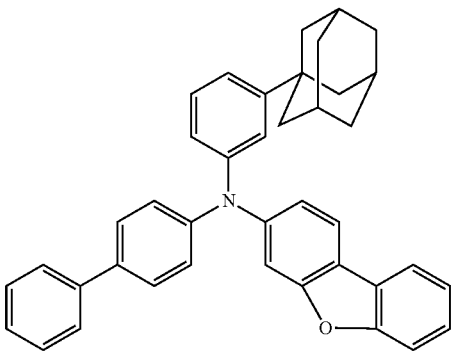
4
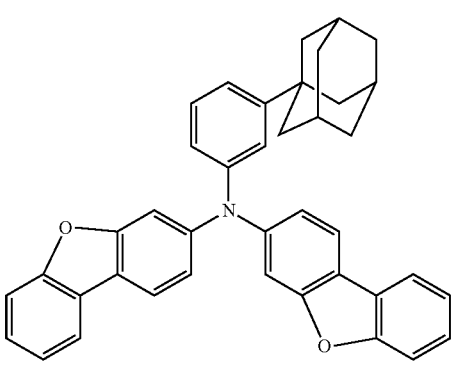
5
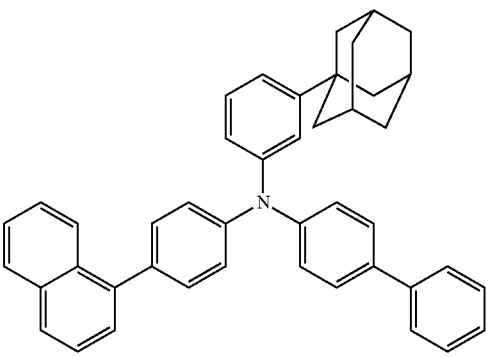
6
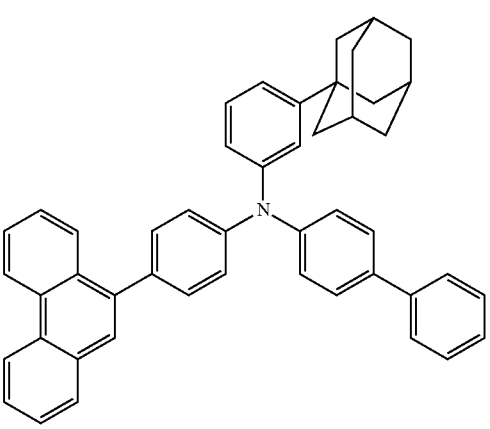

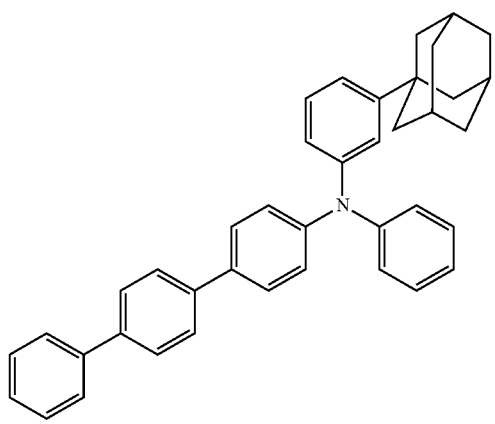
7
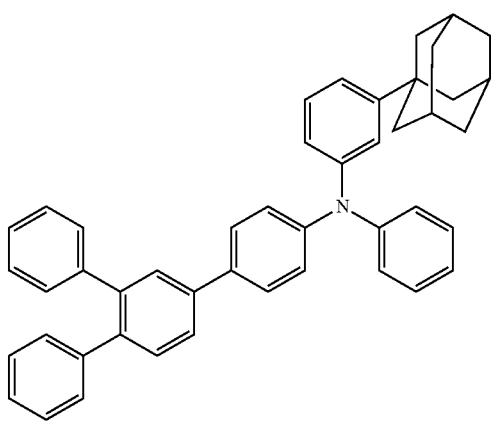
10
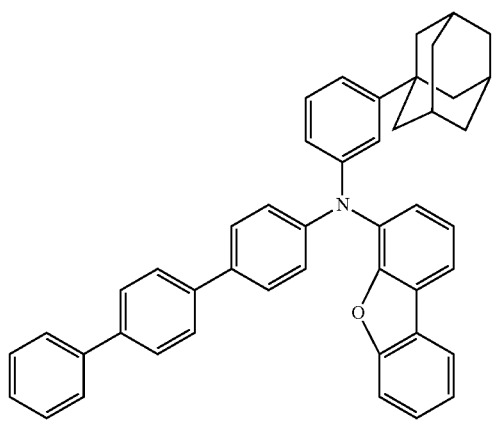
8
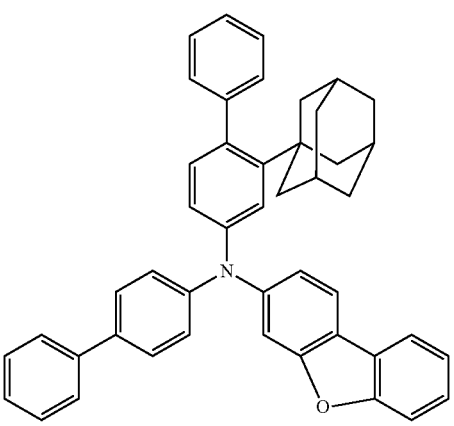
11
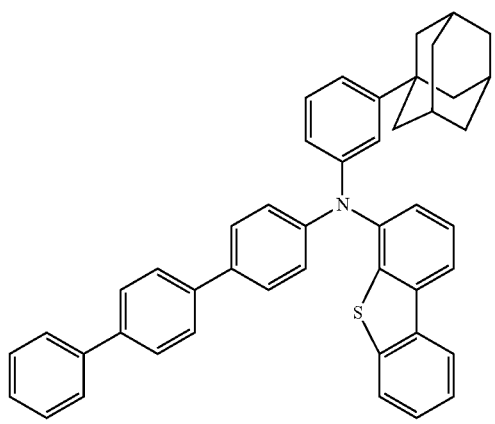
9
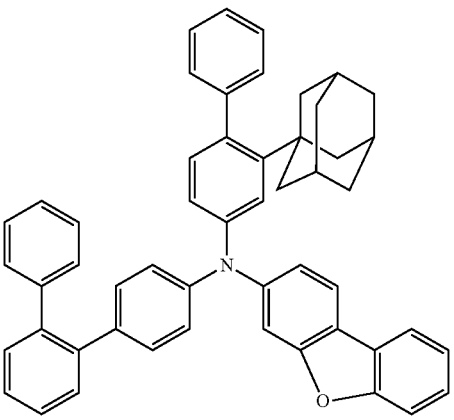
12

13
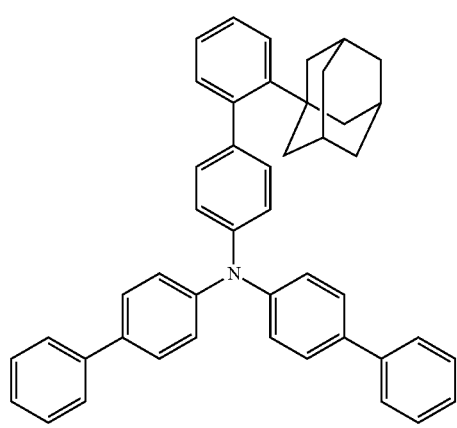
14
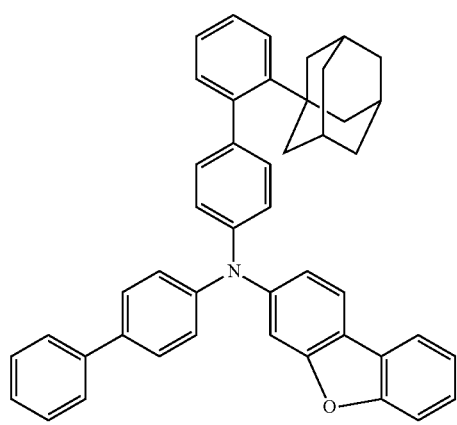
15
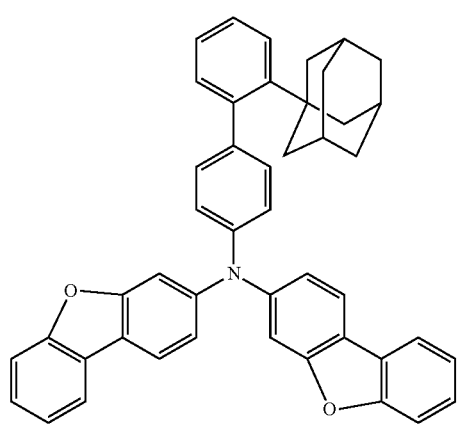
16
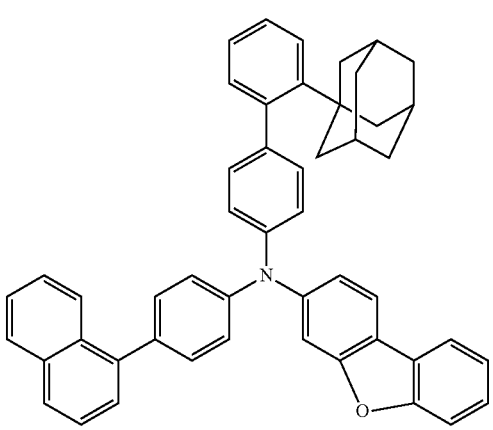
17
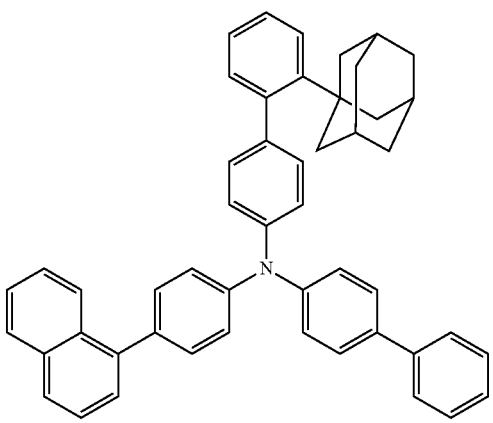
18
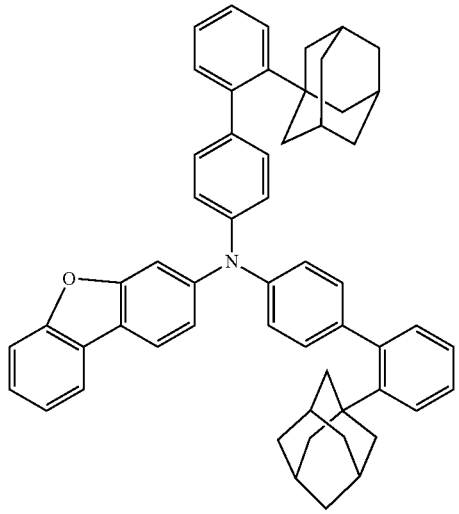

19
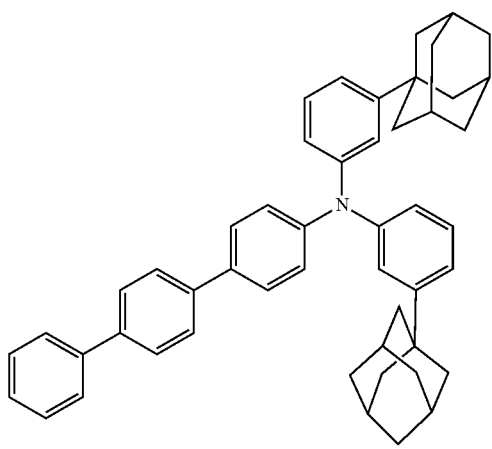
20
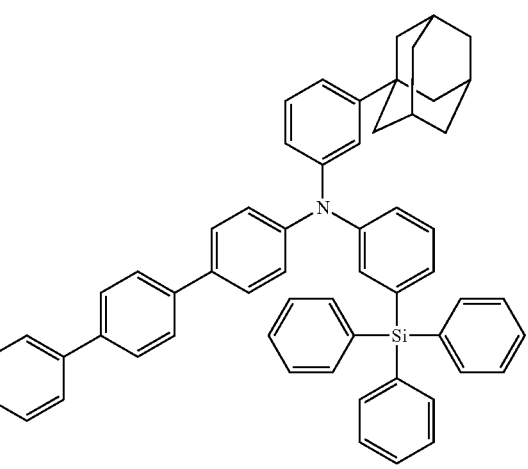
21
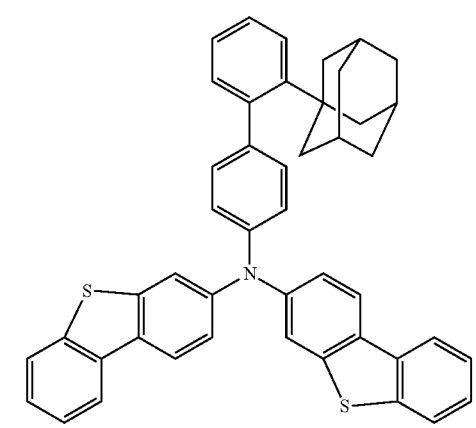
22
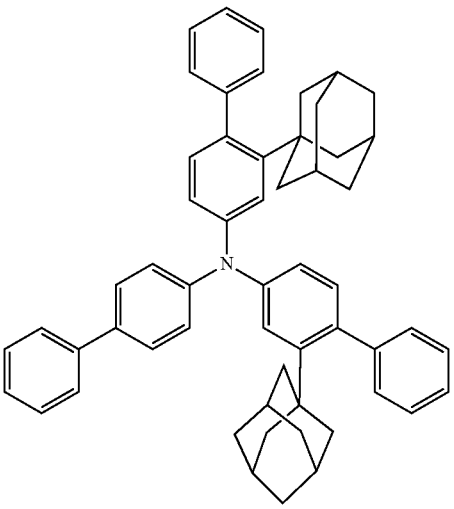
23
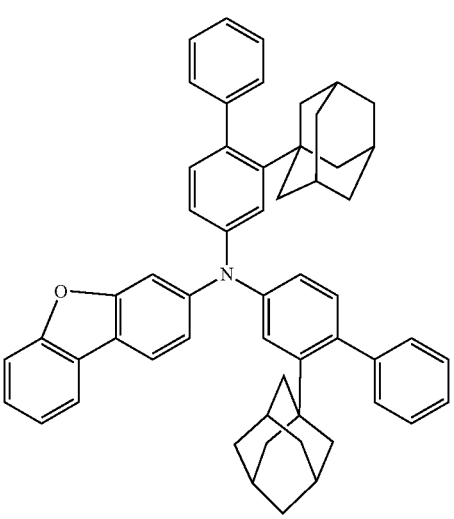
24
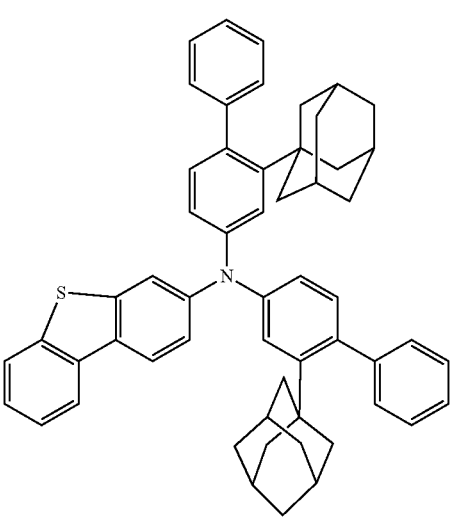

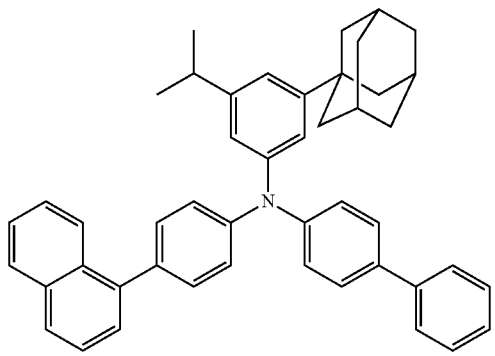
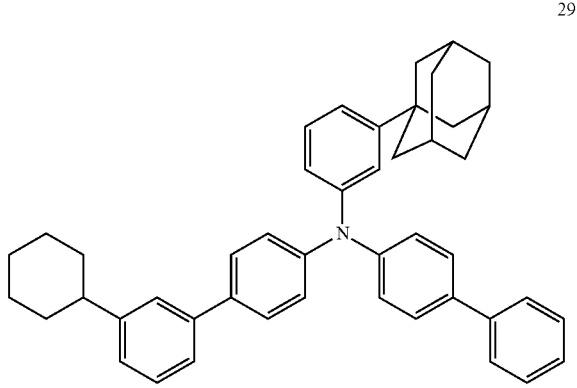
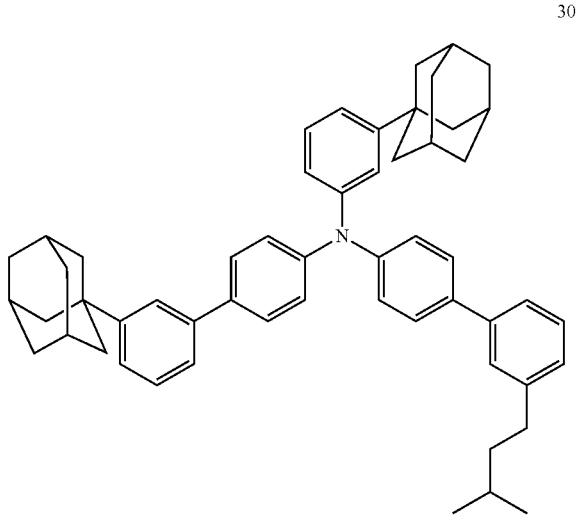
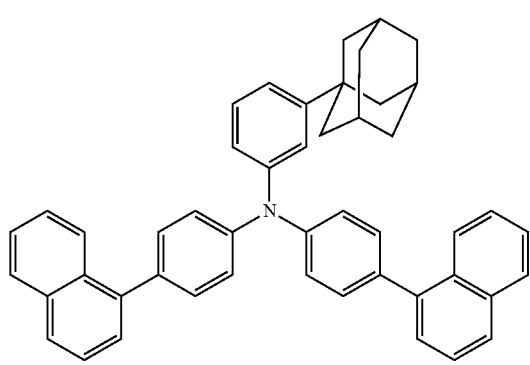
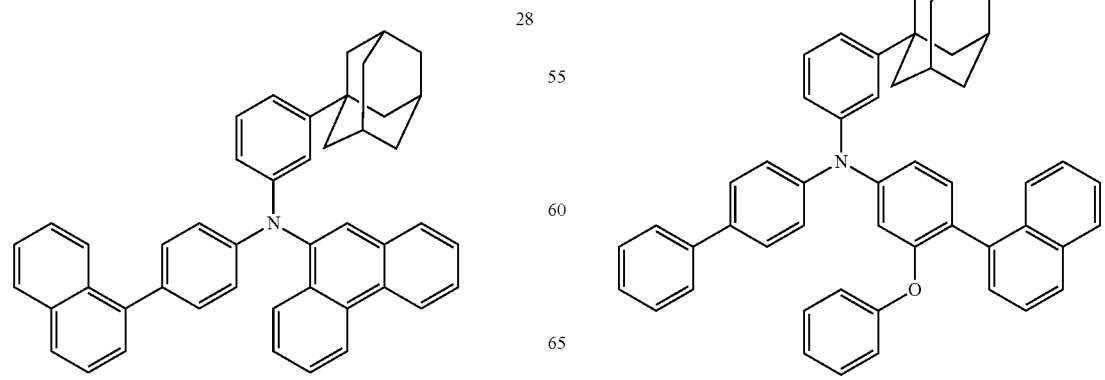

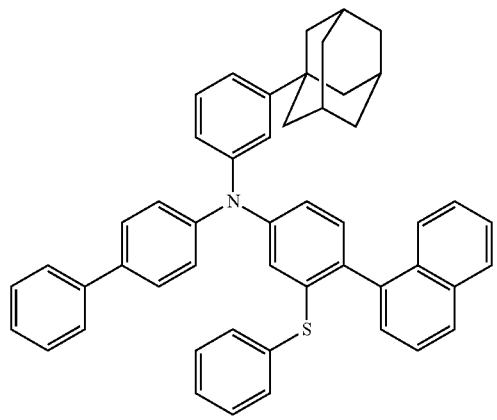
32
Compound Group 2
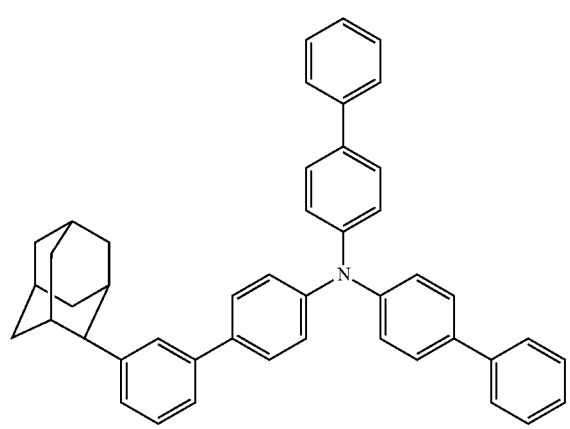
33
34
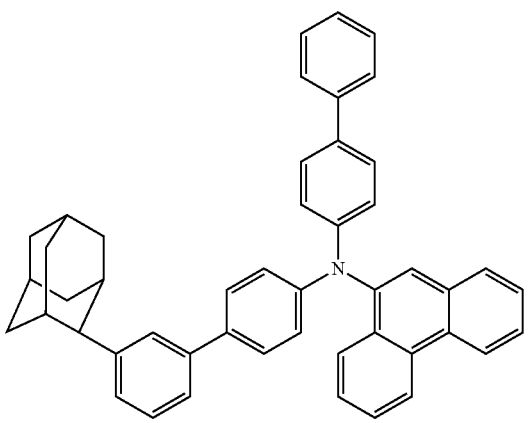
35
36
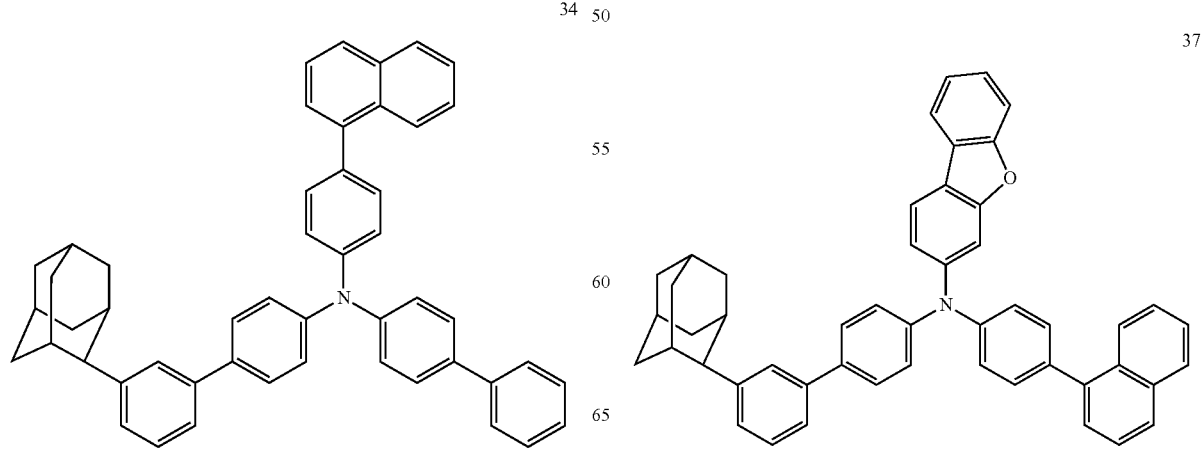
37

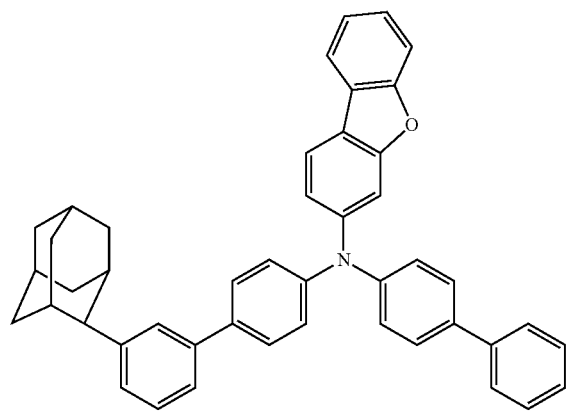
38
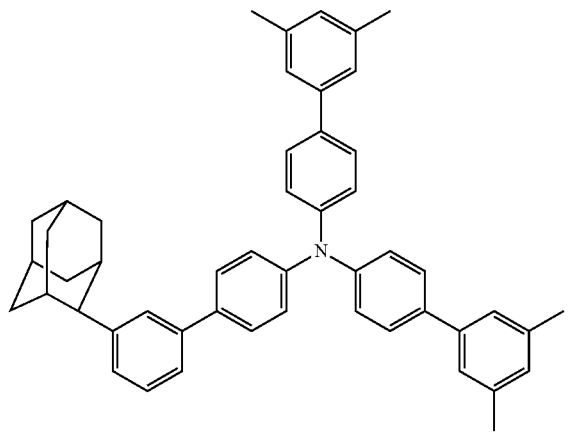
41
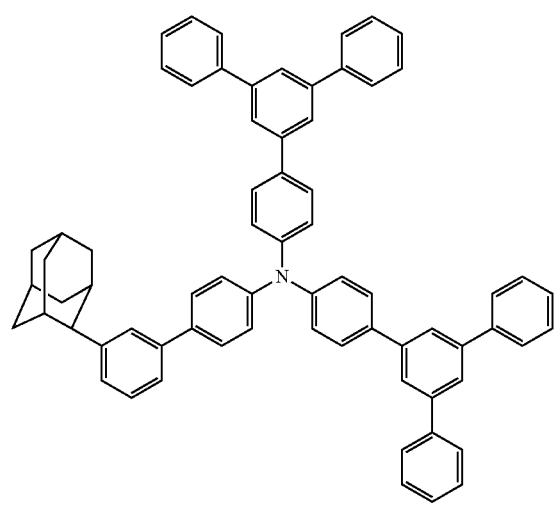
39
40
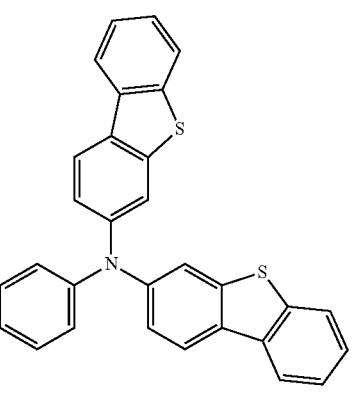
42
43

44
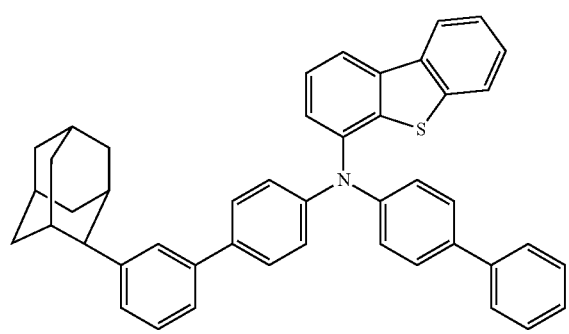
45
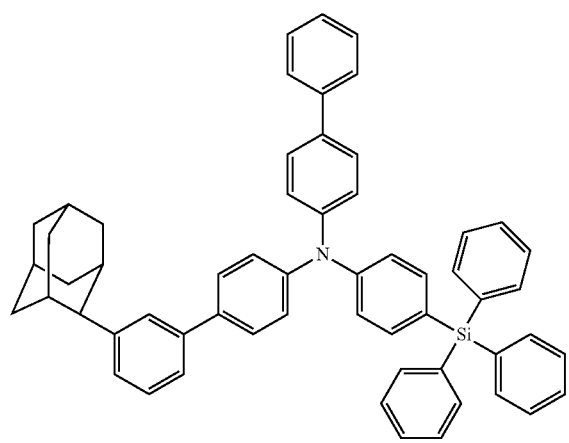
46
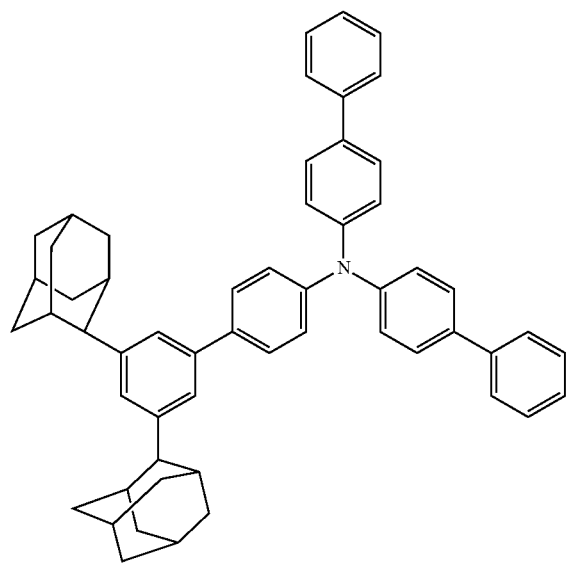
47
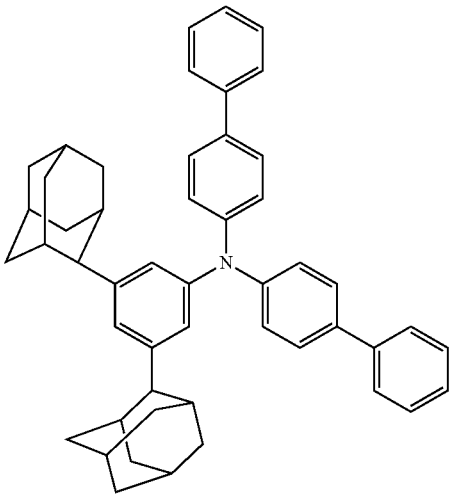
48
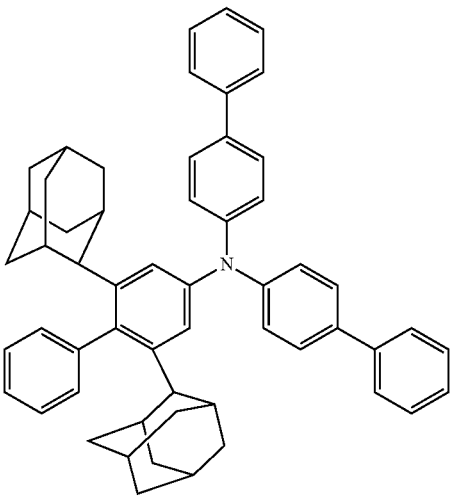
49
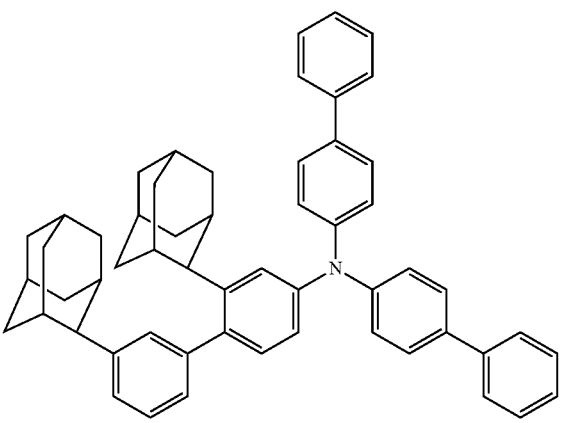

50
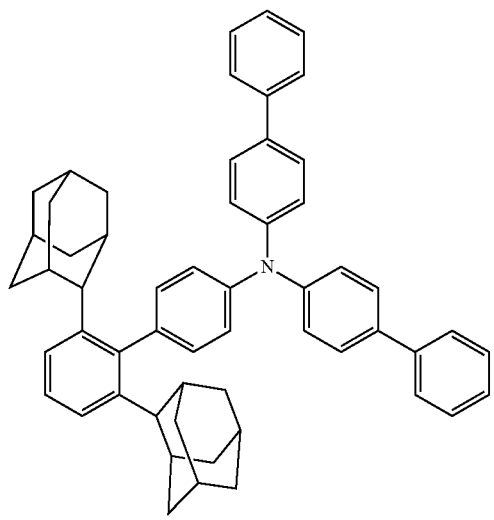
51
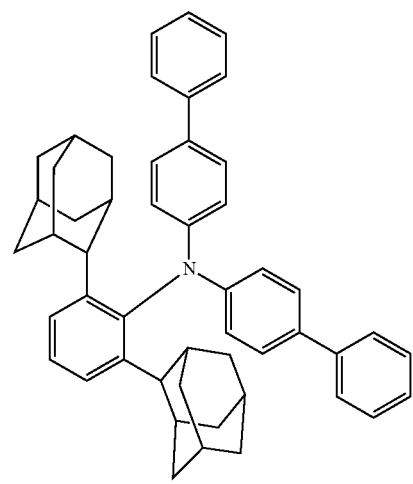
52
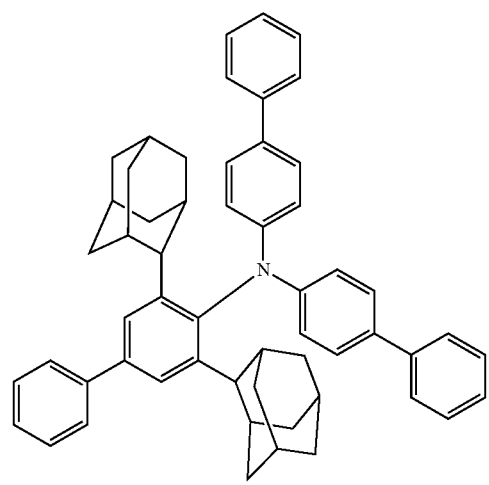
53
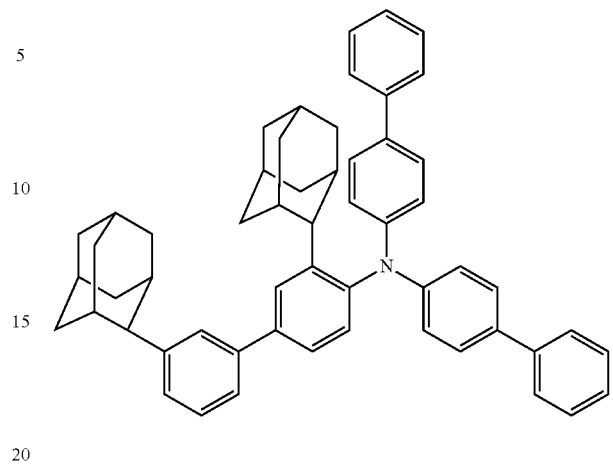
54
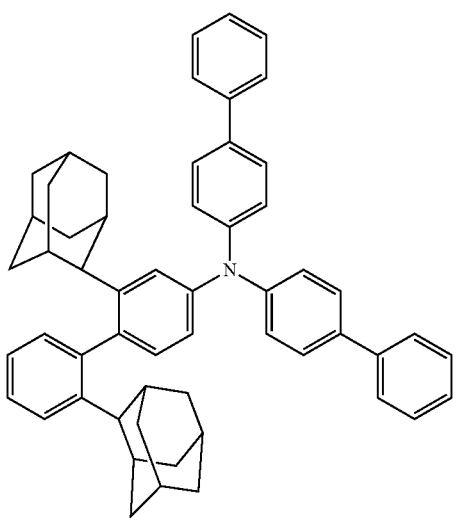
55
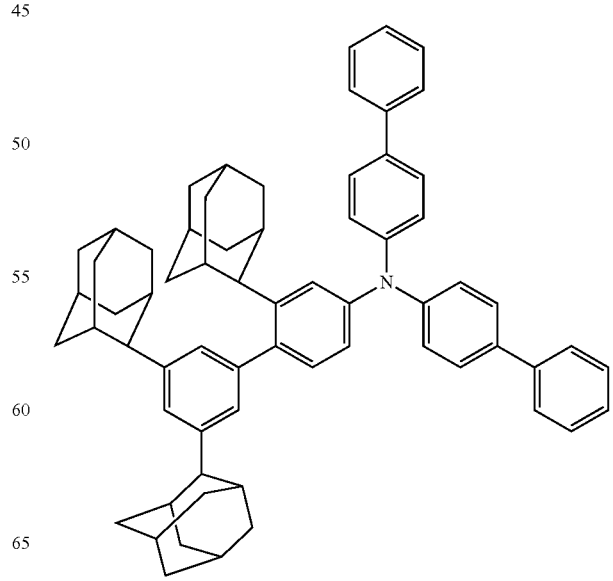

56
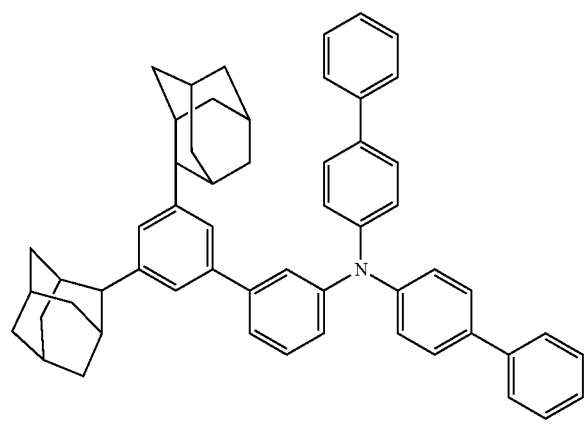
57
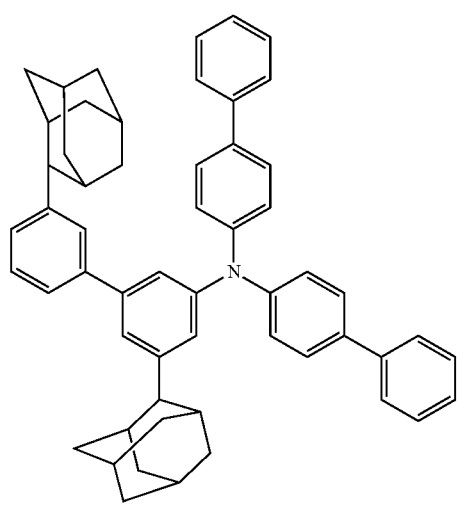
58
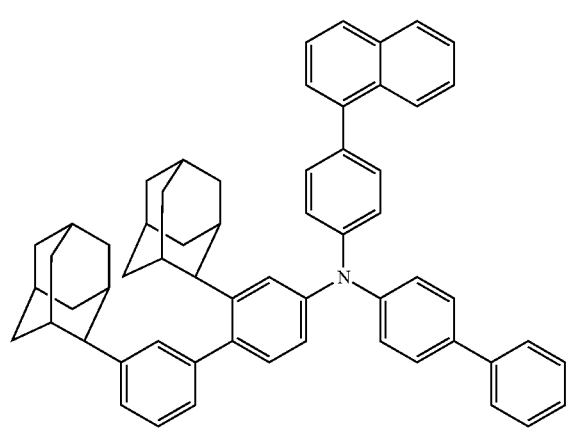
59
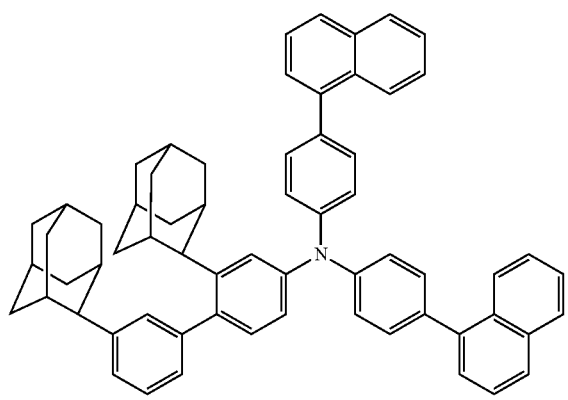
60
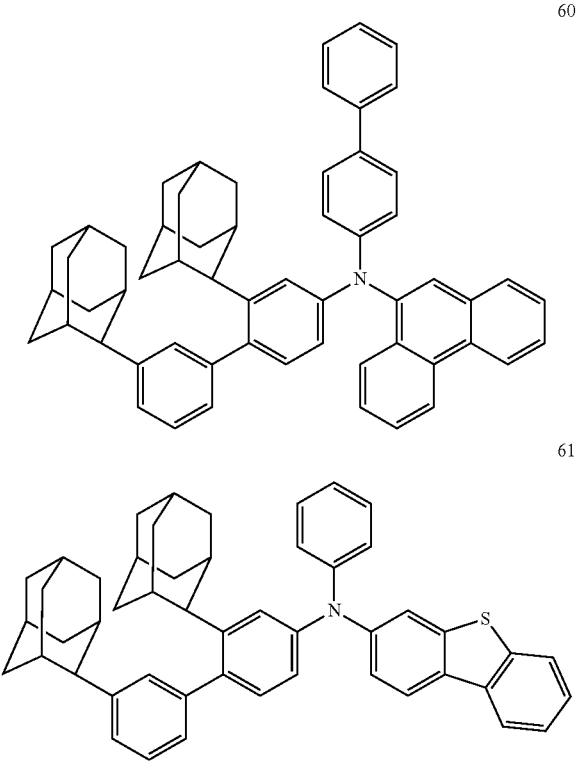
61
62
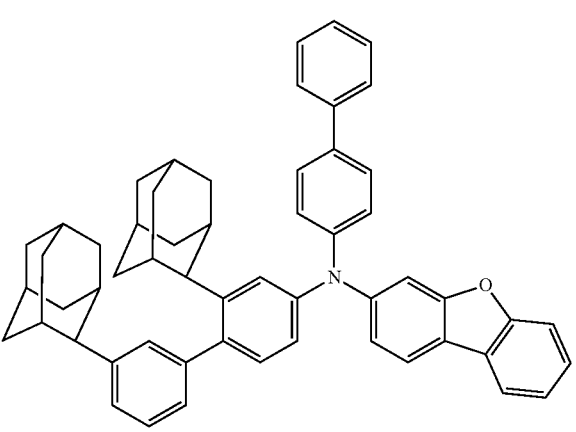

27
-continued
63
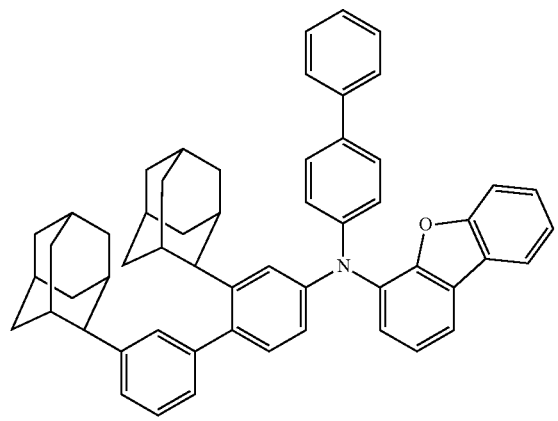
64
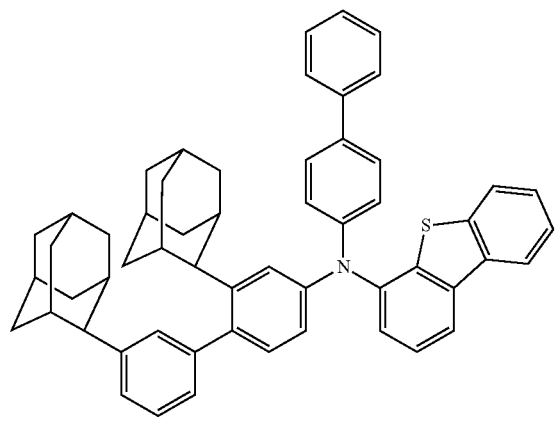
65
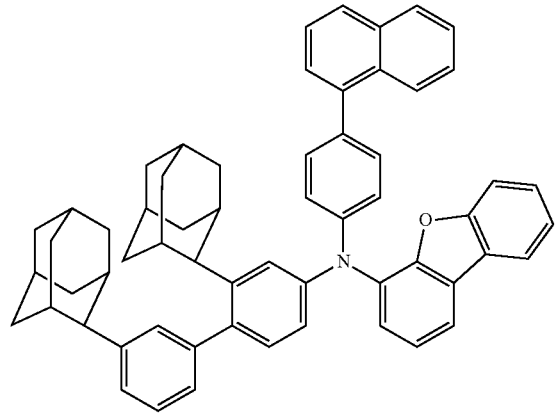
28
-continued
66
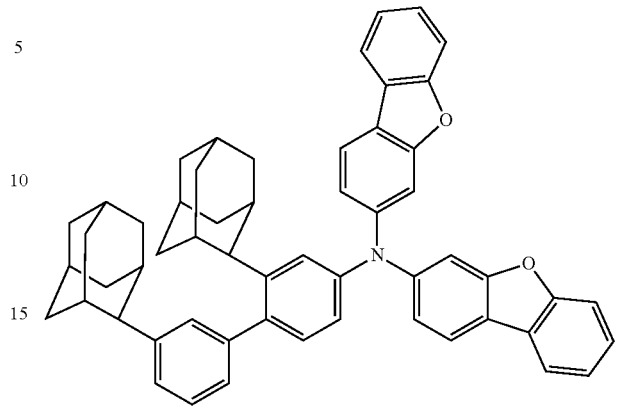
67
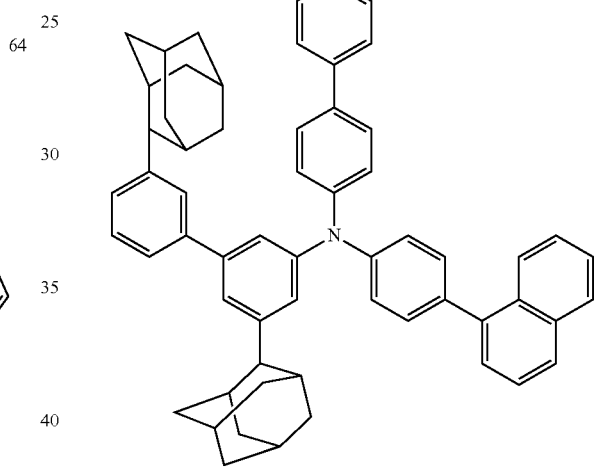
68
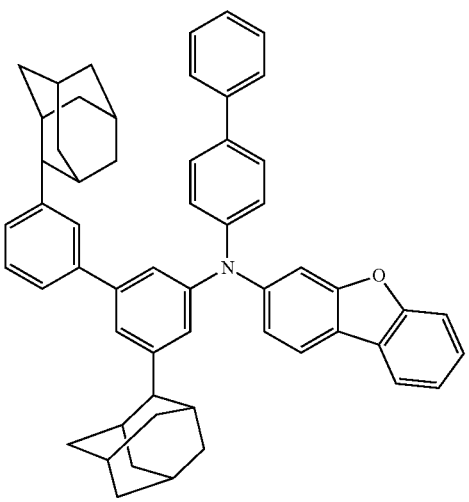

29
-continued
69
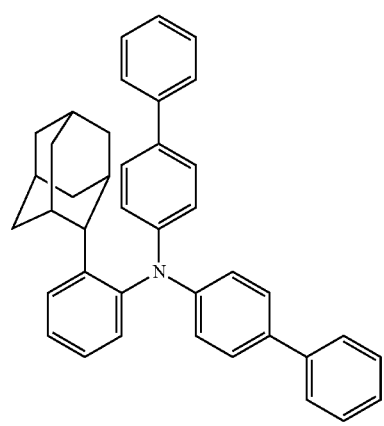
70
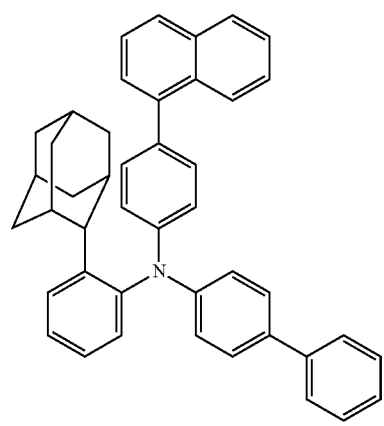
71
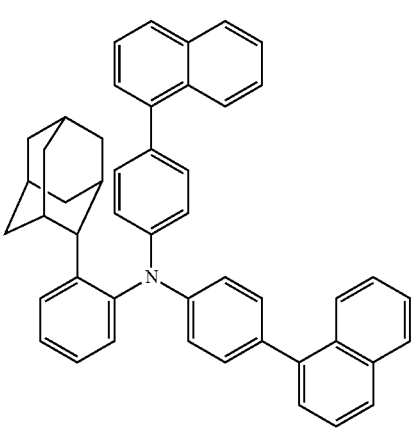
30
-continued
72
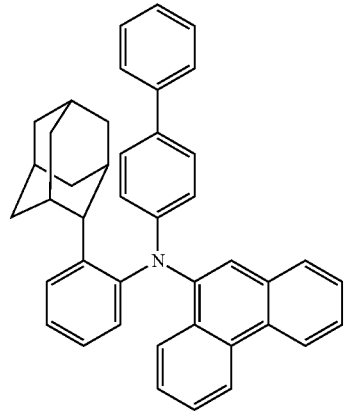
73
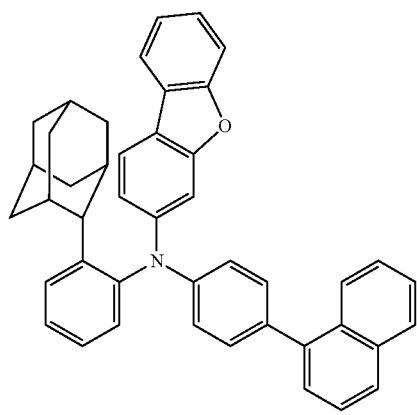
74
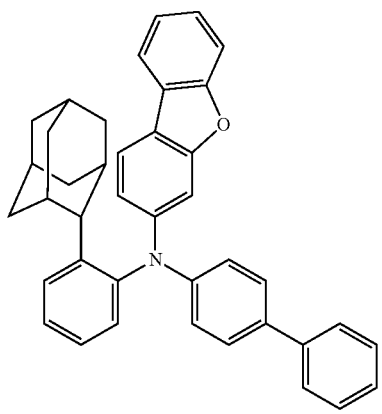
75
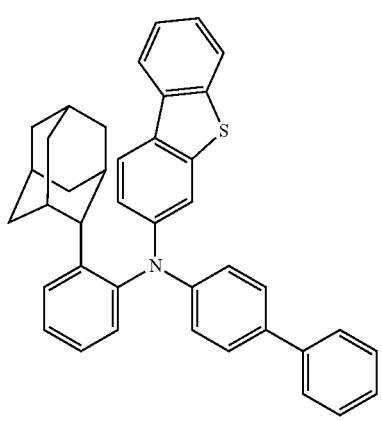

76
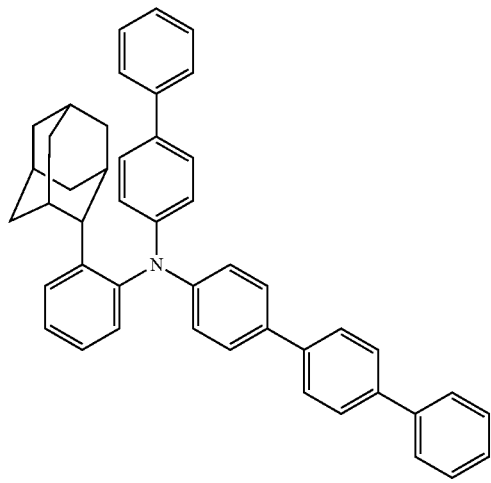
77
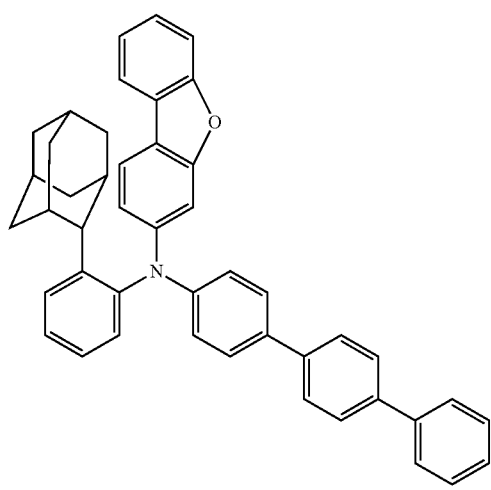
78
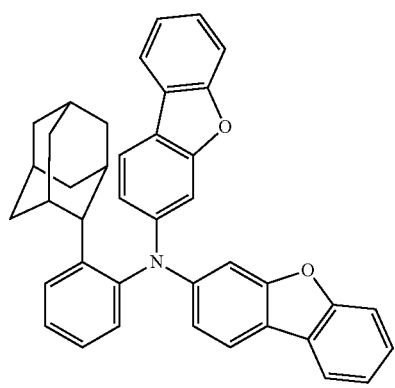
79
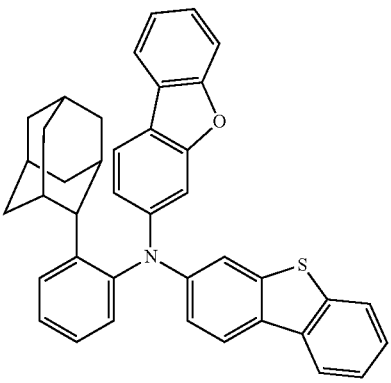
80
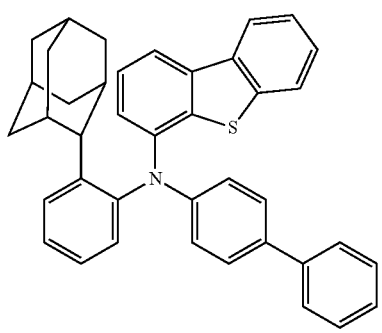
81
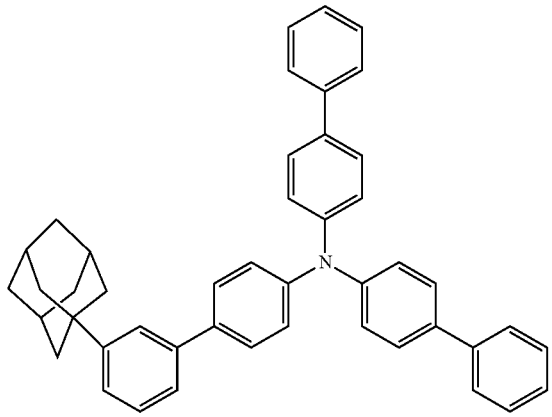
82
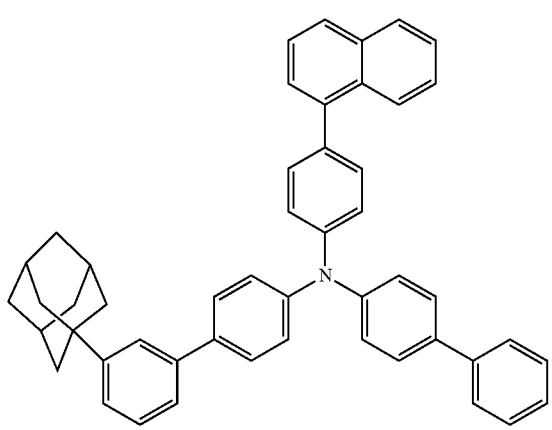

83
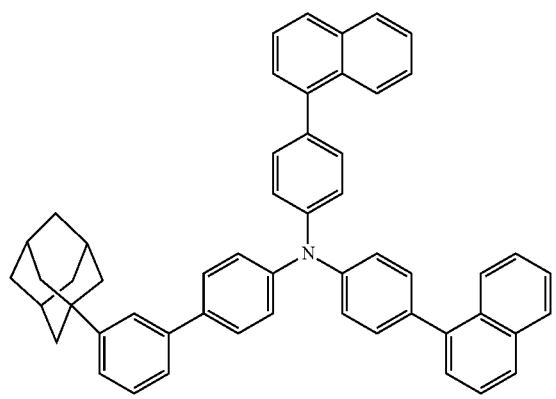
84
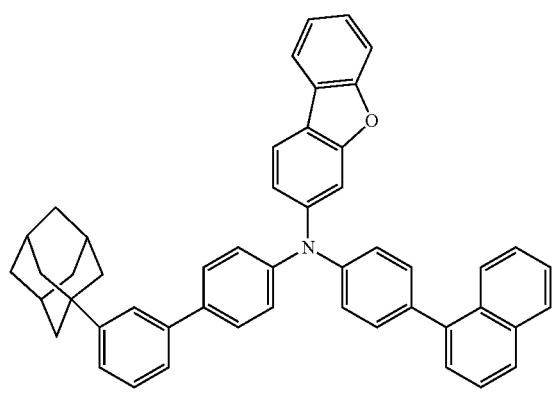
85
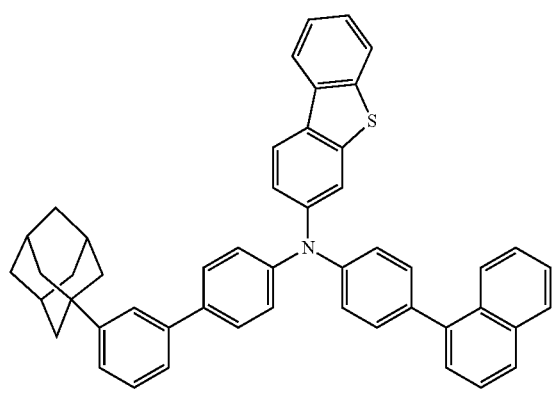
86
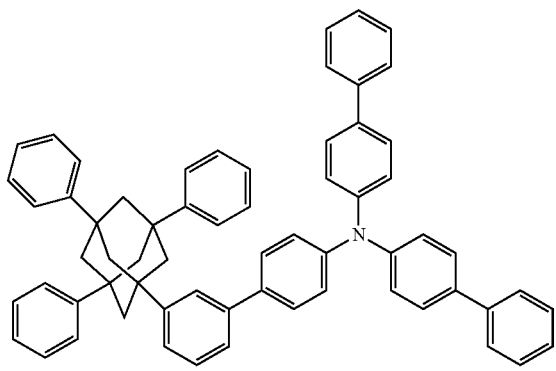
87
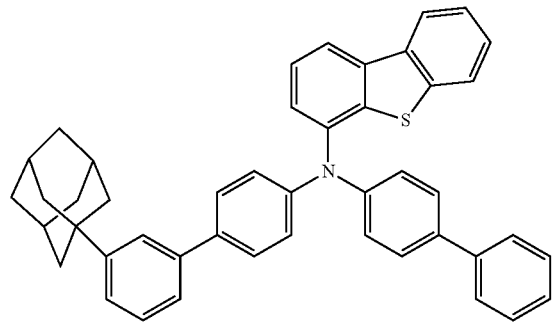
88
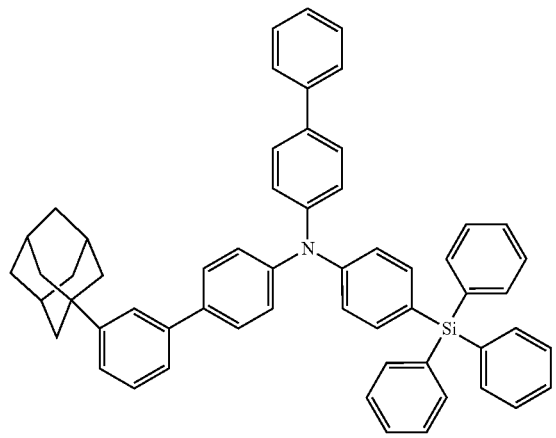
89
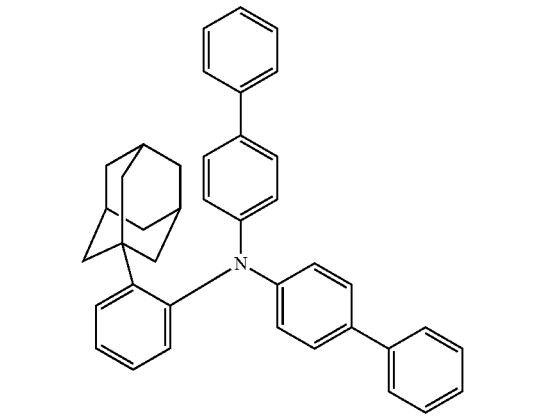
90
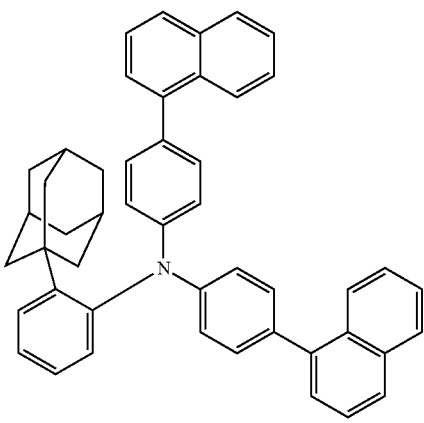

91
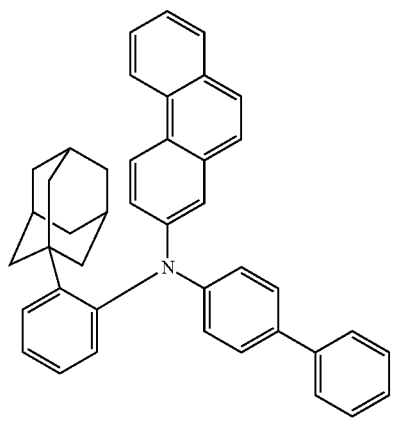

92
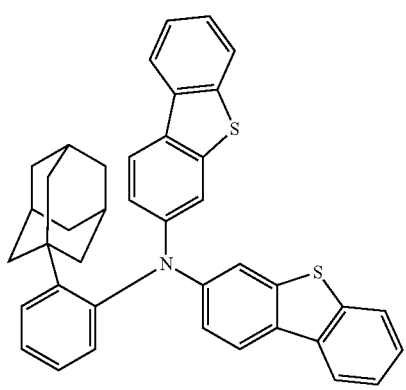

93
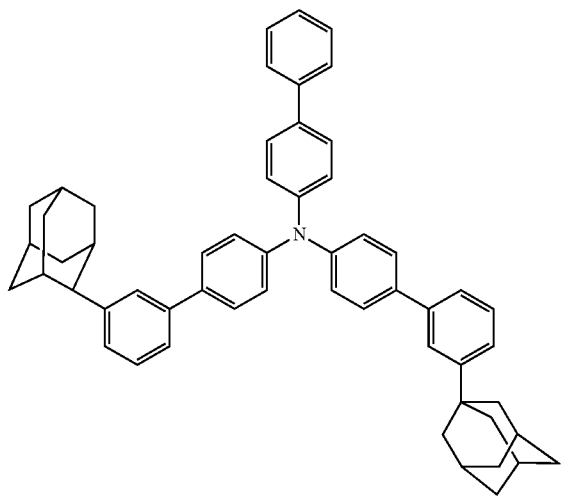

94
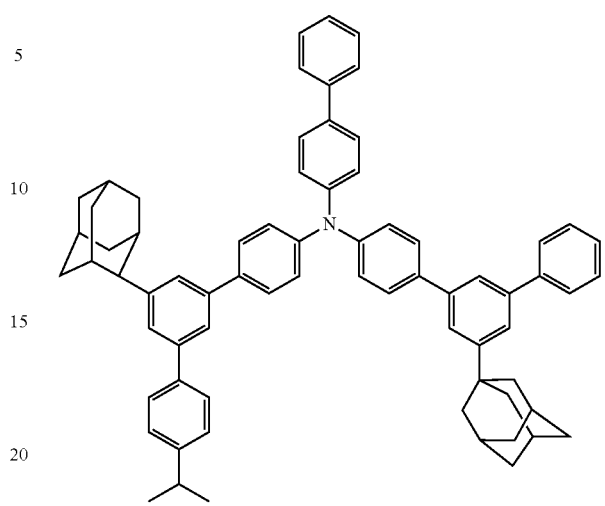

95
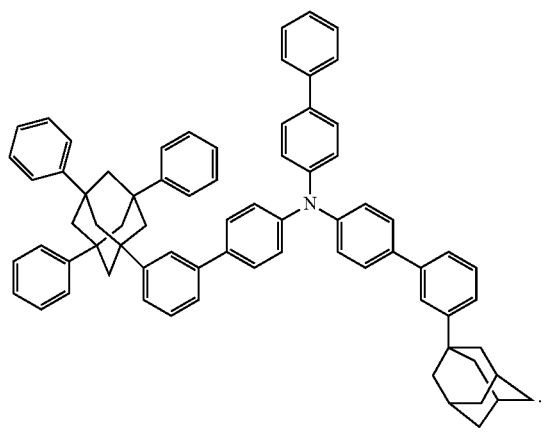

In an embodiment of the inventive concept, there is provided a monoamine compound represented by the following Formula 1:

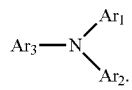

Formula 1

In Formula 1, at least one selected from $Ar_1$, $Ar_2$ and $Ar_3$ is represented by the following Formula 2, and the remaining ones of $Ar_1$, $Ar_2$ and $Ar_3$ are each independently a substituted or unsubstituted aryl group having 6 to 30 carbon atoms for forming a ring, or a substituted or unsubstituted heteroaryl group having 2 to 30 carbon atoms for forming a ring:

Formula 2

In Formula 2, $R_1$ to $R_3$ are each independently a hydrogen atom, a deuterium atom, a halogen atom, a cyano group, a substituted or unsubstituted silyl group, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring; "m" is 0 or 1; "a", "b", "x" and "y" are each independently an integer of 0 to 4, where if "m" is 0, "x" is an integer of 1 or more, and if "m" is 1, "x+y" is an integer of 1 or more; and "Ad" is represented by the following Formula 3:

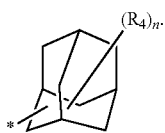

Formula 3

In Formula 3, $R_4$ is a hydrogen atom, a deuterium atom, a halogen atom, a cyano group, a substituted or unsubstituted silyl group, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, and "n" is an integer of 0 to 15.

In an embodiment, Formula 3 may be represented by the following Formula 3-1 or Formula 3-2:

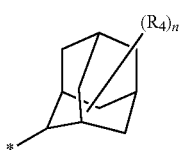

Formula 3-1

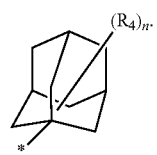

Formula 3-2

In Formula 3-1 and Formula 3-2, $R_4$ and "n" are the same as defined in Formula 3.

In an embodiment, Formula 1 may be represented by the following Formula 1-A or Formula 1-B:

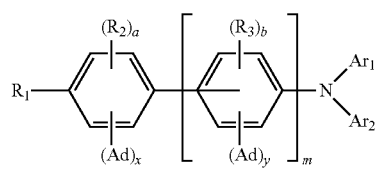

Formula 1-A

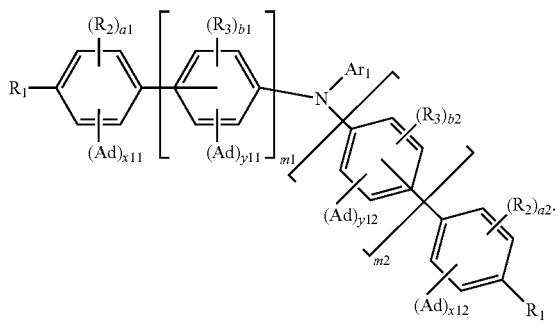

Formula 1-B

In Formula 1-B, "m1" and "m2" are each independently 0 or 1, and "a1", "a2", "b1", "b2", "x11", "x12", "y11", and "y12" are each independently an integer of 0 to 4, where if "m1" is 0, "x11" is an integer of 1 or more, if "m1" is 1, "x11+y11" is an integer of 1 or more, if "m2" is 0, "x12" is an integer of 1 or more, and if "m2" is 1, "x12+y12" is an integer of 1 or more.

In Formula 1-A and Formula 1-B, $Ar_1$ and $Ar_2$ are the same as defined in Formula 1, and $R_1$ to $R_3$, "a", "a", "b", "x", "y", and "Ad" are the same as defined in Formula 2.

In an embodiment, Formula 1-A may be represented by any one among the following Formula 1-1 to Formula 1-3:

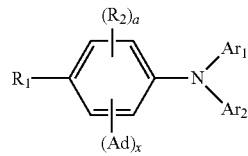

Formula 1-1

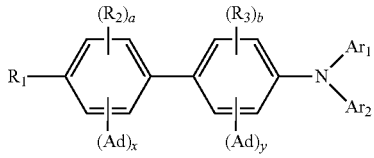

Formula 1-2

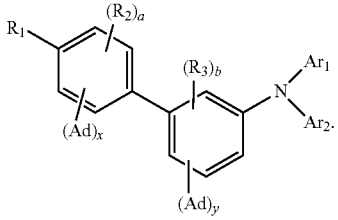

Formula 1-3

In Formula 1-1 to Formula 1-3, $Ar_1$ and $Ar_2$ are the same as defined in Formula 1, and $R_1$ to $R_3$, "a", "b", "b", "x", "y", and "Ad" are the same as defined in Formula 2.

In an embodiment, Formula 1-1 may be represented by any one among the following Formula 1-1a to Formula 1-1e:

Formula 1-1a
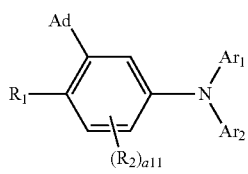

Formula 1-1b
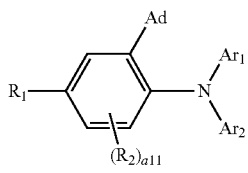

Formula 1-1c
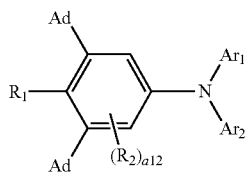

Formula 1-1d
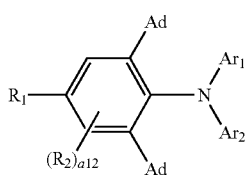

Formula 1-1e
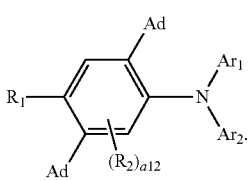

In Formula 1-1a and Formula 1-1 b, "a11" is an integer of 0 to 3; in Formula 1-1c, Formula 1-1d, and Formula 1-1e, "a12" is an integer of 0 to 2; and in Formula 1-1a to Formula 1-1e, $Ar_1$ and $Ar_2$ are the same as defined in Formula 1, and $R_1$, $R_2$, and "Ad" are the same as defined in Formula 2.

In an embodiment, Formula 1-2 may be represented by any one among the following Formula 1-2a to Formula 1-2c:

Formula 1-2a
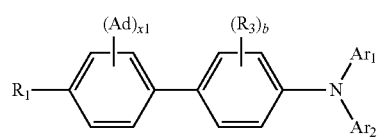

Formula 1-2b
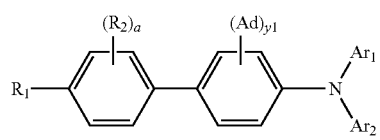

Formula 1-2c
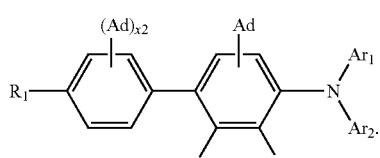

In Formula 1-2a, "x1" is 1 or 2; in Formula 1-2b, "y1" is 1 or 2; in Formula 1-2c, "x2" is 1 or 2, $R_{31}$ and $R_{32}$ are each independently a hydrogen atom, a deuterium atom, a halogen atom, a cyano group, a substituted or unsubstituted silyl group, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring. In Formula 1-2a to Formula 1-2c, $Ar_1$ and $Ar_2$ are the same as defined in Formula 1, "a", "b", $R_1$, $R_2$, $R_3$, and "Ad" are the same as defined in Formula 2.

In an embodiment, Formula 1-3 may be represented by any one among the following Formula 1-3a to Formula 1-3c:

Formula 1-3a
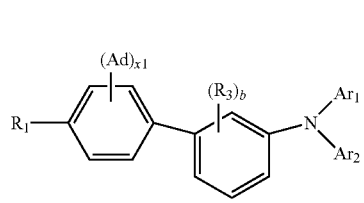

Formula 1-3b
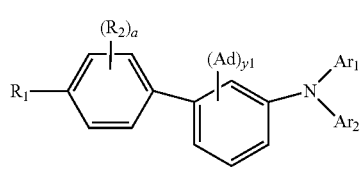

Formula 1-3c
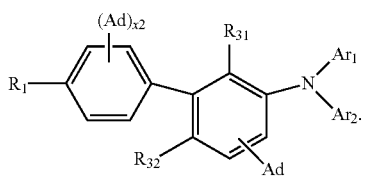

In Formula 1-3a, "x1" is 1 or 2; in Formula 1-3b, "y1" is 1 or 2; in Formula 1-3c, "x2" is 1 or 2, $R_{31}$ and $R_{32}$ are each independently a hydrogen atom, a deuterium atom, a halogen atom, a cyano group, a substituted or unsubstituted silyl group, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring. In Formula 1-3a to Formula 1-3c, $Ar_1$ and $Ar_2$ are the same as defined in Formula 1, "a", "b", $R_1$, $R_2$, $R_3$, and "Ad" are the same as defined in Formula 2.

In an embodiment, $Ar_1$ and $Ar_2$ may be each independently a substituted or unsubstituted phenyl group, a substituted or unsubstituted biphenyl group, a substituted or unsubstituted terphenyl group, a substituted or unsubstituted phenanthryl group, a substituted or unsubstituted dibenzofuran group, or a substituted or unsubstituted dibenzothiophene group.

In an embodiment, $Ar_1$ and $Ar_2$ may be each independently an aryl group having 6 to 30 carbon atoms for forming a ring, wherein the aryl group is an unsubstituted aryl group or an aryl group substituted with at least one selected from a halogen atom, a cyano group, an alkyl group having 1 to 20 carbon atoms, an alkoxy group having 1 to 10 carbon atoms, an aryloxy group having 1 to 20 carbon atoms, an alkylthio group having 1 to 10 carbon atoms, an arylthio group having 1 to 20 carbon atoms, a triarylsilyl group having 18 to 50 carbon atoms, and an adamantyl group.

In an embodiment, $Ar_1$ and $Ar_2$ may be each independently a heteroaryl group having 2 to 30 carbon atoms for forming a ring, wherein the heteroaryl group is an unsubstituted heteroaryl group or a heteroaryl group substituted with at least one selected from a halogen atom, a cyano group, an alkyl group having 1 to 20 carbon atoms, an alkoxy group having 1 to 10 carbon atoms, an aryloxy group having 1 to 20 carbon atoms, an alkylthio group having 1 to 10 carbon atoms, an arylthio group having 1 to 20 carbon atoms, a triarylsilyl group having 18 to 50 carbon atoms, and an adamantyl group.

In an embodiment, $Ar_1$ and $Ar_2$ may be each independently represented by any one among the following Formula A-1 to Formula A-20:

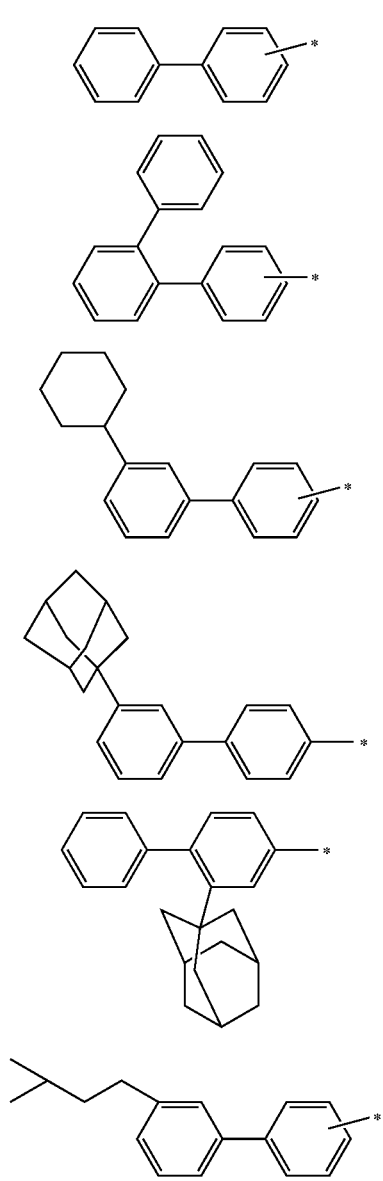

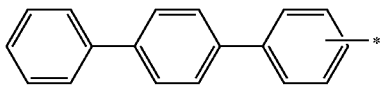
A-7

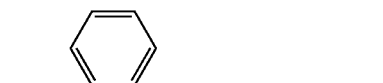
A-8

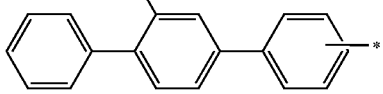
A-9

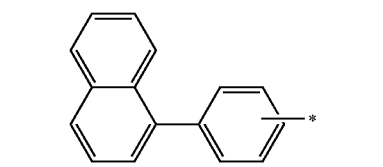
A-10

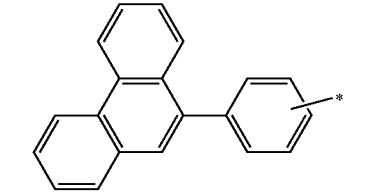
A-11

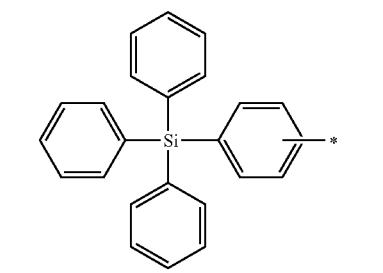
A-12

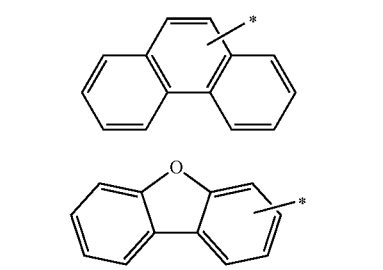
A-13

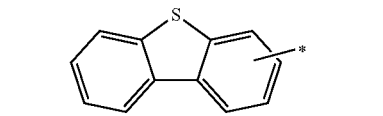
A-14

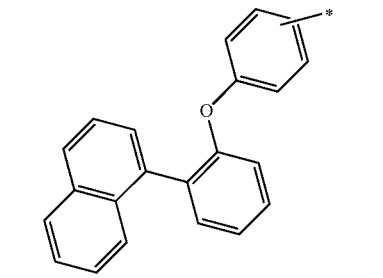
A-15

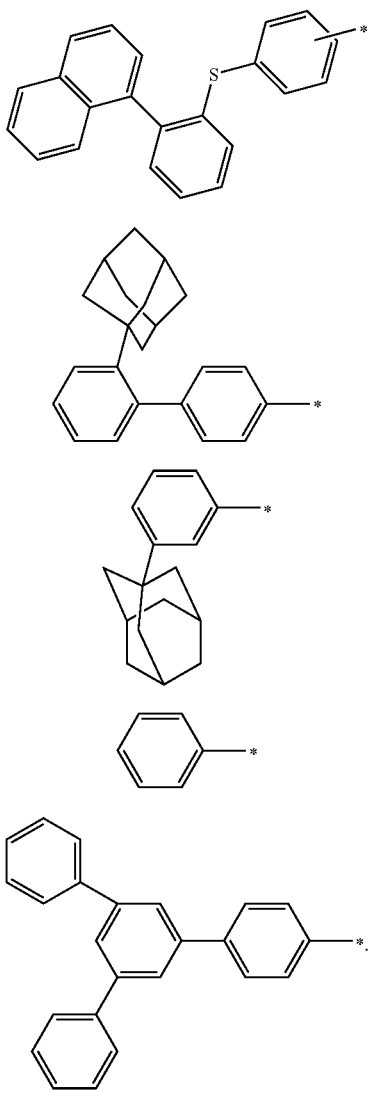

In an embodiment, R₁ may be a hydrogen atom or an unsubstituted phenyl group.

In an embodiment, the monoamine compound represented by Formula 1 may be represented by any one among the compounds in Compound Group 1 and Compound Group 2.

BRIEF DESCRIPTION OF THE FIGURES

The accompanying drawings are included to provide a further understanding of the inventive concept, and are incorporated in and constitute a part of this specification. The drawings illustrate example embodiments of the inventive concept and, together with the description, serve to explain principles of the inventive concept. In the drawings.

DETAILED DESCRIPTION

Figure 1:
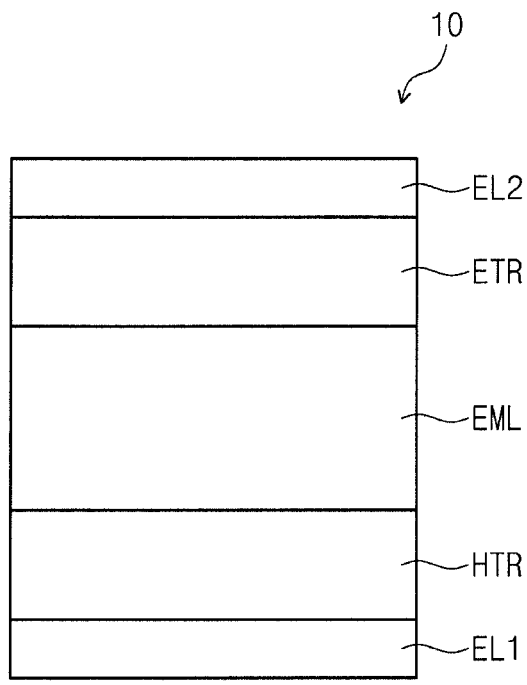
FIG. 1 is a cross-sectional view schematically illustrating an organic electroluminescence device according to an embodiment of the inventive concept.

The inventive concept may have various modifications and may be embodied in different forms, and example embodiments will be explained in detail with reference to the accompany drawings. The inventive concept may, however, be embodied in different forms and should not be construed as limited to the embodiments set forth herein. Rather, all modifications, equivalents, and substituents which are included in the spirit and technical scope of the inventive concept should be included in the inventive concept.

Like reference numerals refer to like elements throughout. In the drawings, the dimensions of structures are exaggerated for clarity of illustration. It will be understood that, although the terms "first," "second," etc. may be used herein to describe various elements, these elements should not be limited by these terms. These terms are only used to distinguish one element from another element. Thus, a first element could be termed a second element without departing from the teachings of the present invention. Similarly, a second element could be termed a first element. As used herein, the singular forms are intended to include the plural forms as well, unless the context clearly indicates otherwise.

It will be further understood that the terms "comprises" and/or "comprising," when used in this specification, specify the presence of stated features, numerals, steps, operations, elements, parts, or the combination thereof, but do not preclude the presence or addition of one or more other features, numerals, steps, operations, elements, parts, or the combination thereof. It will also be understood that when a layer, a film, a region, a plate, etc. is referred to as being "on" another part, it can be directly on the other part, or intervening elements may also be present.

Expressions such as "at least one of," "one of," and "selected from," when preceding a list of elements, modify the entire list of elements and do not modify the individual elements of the list. Further, the use of "may" when describing embodiments of the present invention refers to "one or more embodiments of the present invention."

In the description, ——— * refers to a connecting position (e.g., a binding site).

In the description, the term "substituted" when used in connection with a functional group may refer to the functional group being substituted with at least one substituent selected from a deuterium atom, a halogen atom, a cyano group, a nitro group, an amino group, a silyl group, a boron group, a phosphine oxide group, a phosphine sulfide group, an alkyl group, an alkenyl group, an alkoxy group, an aryloxy group, an alkylthio group, an arylthio group, a hydrocarbon ring group, an aryl group, and a heteroaryl group. In addition, each of the above-mentioned substituents may be substituted or unsubstituted. For example, a biphenyl group may be described as an aryl group or as a phenyl group substituted with a phenyl group.

In the present description, the halogen atom may include a fluorine atom, a chlorine atom, a bromine atom, and an iodine atom, without limitation.

In the present description, the alkyl may be a linear, branched or cyclic alkyl group. The carbon number of the alkyl may be from 1 to 50, from 1 to 30, from 1 to 20, from 1 to 10, or from 1 to 6. The alkyl may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldocecyl, 2-octyldodecyl, n-tridecyl, n-tetradecyl, c-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-henicosyl, n-docosyl, n-tricosyl, n-tetracosyl, n-pentacosyl, n-hexacosyl, n-heptacosyl, n-octacosyl, n-nonacosyl, n-triacontyl, and/or the like, without limitation.

In the present description, the hydrocarbon ring group may refer to a functional group or a substituent derived from an aliphatic hydrocarbon ring. The hydrocarbon ring group may be a saturated hydrocarbon ring group having 5 to 20 carbon atoms for forming a ring.

In the present description, the aryl group may refer to a functional group or a substituent derived from an aromatic hydrocarbon ring. The aryl group may be a monocyclic aryl group or a polycyclic aryl group. The carbon number for forming a ring in the aryl group may be 6 to 30, 6 to 20, or 6 to 15. Examples of the aryl group may include phenyl, naphthyl, fluorenyl, anthracenyl, phenanthryl, biphenyl, terphenyl, quaterphenyl, quinqphenyl, sexiphenyl, triphenylenyl, pyrenyl, benzofluoranthenyl, chrysenyl, and the like, without limitation.

In the present description, the fluorenyl group may be substituted, and two substituents may be combined with each other to form a spiro structure.

In the present description, the heteroaryl group may refer to a functional group or a substituent derived from an aromatic ring including at least one of O, N, P, Si or S as a ring-forming heteroatom. The carbon number for forming a ring of the heteroaryl group may be 2 to 30, or 2 to 20. The heteroaryl group may be monocyclic heteroaryl group or polycyclic heteroaryl group. Examples of the polycyclic heteroaryl group may have dicyclic or tricyclic structure. Examples of the heteroaryl group may include thiophene, furan, pyrrole, imidazole, thiazole, oxazole, oxadiazole, triazole, pyridine, bipyridine, pyrimidine, triazine, triazole, acridine, pyridazine, pyrazinel, quinoline, quinazoline, quinoxaline, phenoxazine, phthalazine, pyrido pyrimidine, pyrido pyrazine, pyrazino pyrazine, isoquinoline, indole, carbazole, N-arylcarbazole, N-heteroarylcarbazole, N-alkylcarbazole, benzoxazole, benzoimidazole, benzothiazole, benzocarbazole, benzothiophene, dibenzothiophene, thienothiophene, benzofuran, phenanthroline, thiazole, isooxazole, oxadiazole, thiadiazole, phenothiazine, dibenzosilole, dibenzofuran, and the like, without limitation.

In the present description, the silyl group may include an alkylsilyl group and/or an arylsilyl group. Examples of the silyl group may include trimethylsilyl, triethylsilyl, t-butyldimethylsilyl, vinyldimethylsilyl, propyldimethylsilyl, triphenylsilyl, diphenylsilyl, phenylsilyl, and the like. However, an embodiment of the inventive concept is not limited thereto.

In the present description, the thio group may include an alkylthio group and/or an arylthio group. Examples of the alkyl group in the alkylthio group are the same as the alkyl groups exemplified above, and examples of the aryl group in the arylthio group are the same as the aryl groups exemplified above. The carbon number of the alkylthio group is not specifically limited but, for example, may be 1 to 20, or 1 to 10. The carbon number of the arylthio group is not specifically limited but, for example, may be 1 to 20, or 1 to 10.

In the present description, the oxy group may include an alkoxy group and/or an aryloxy group. The alkoxy group may be a linear, branched or cyclic chain. The carbon number of the alkoxy group is not specifically limited but, for example, may be 1 to 20, or 1 to 10. Examples of the oxy group include methoxy, ethoxy, n-propoxy, isopropoxy, butoxy, pentyloxy, hexyloxy, octyloxy, nonyloxy, decyloxy, benzyloxy groups, and the like, without limitation.

Hereinafter, an organic electroluminescence device according to an embodiment of the inventive concept and a monoamine compound of an embodiment included therein will be explained.

Figure 2:
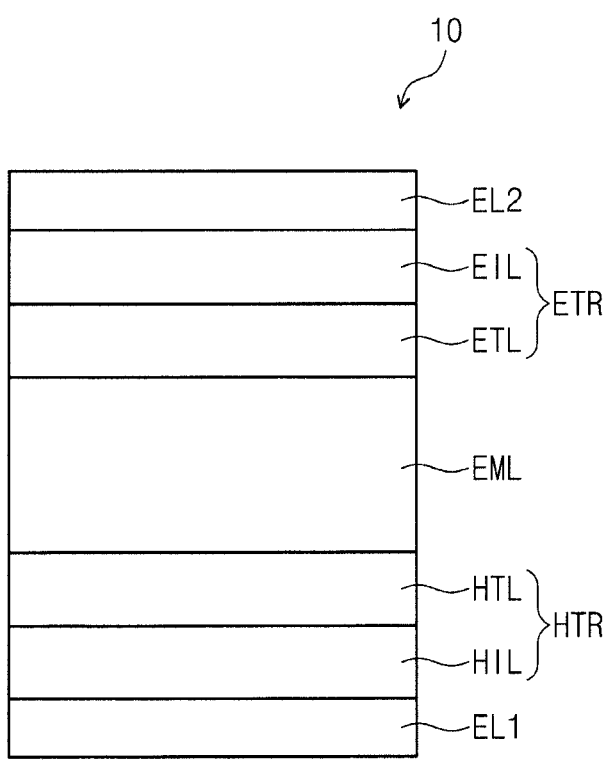
FIG. 2 is a cross-sectional view schematically illustrating an organic electroluminescence device according to an embodiment of the inventive concept.
Figure 3:
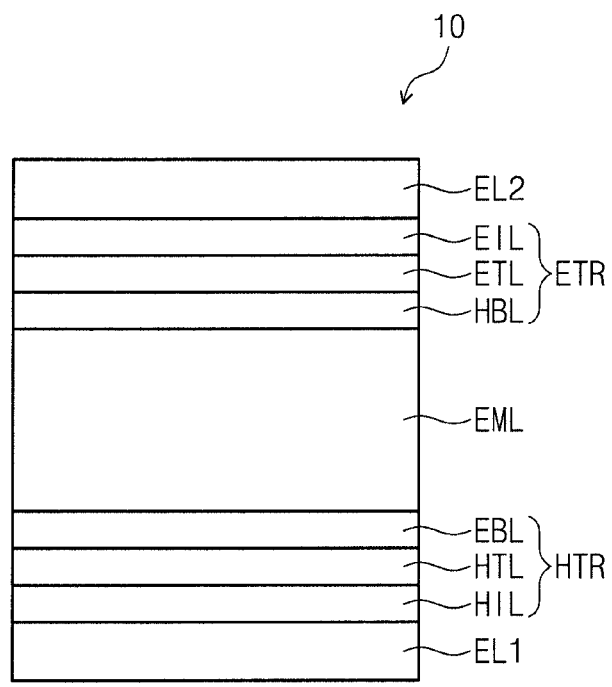
FIG. 3 is a cross-sectional view schematically illustrating an organic electroluminescence device according to an embodiment of the inventive concept.

FIG. 1 to FIG. 3 are cross-sectional views schematically illustrating organic electroluminescence devices according to example embodiments. Referring to FIG. 1 to FIG. 3, an organic electroluminescence device 10 according to an embodiment may include a first electrode EL1, a hole transport region HTR, an emission layer EML, an electron transport region ETR, and a second electrode EL2 laminated in order.

The first electrode EL1 and the second electrode EL2 are disposed (e.g., positioned) oppositely to (e.g., facing) each other, and a plurality of organic layers may be disposed between the first electrode EL1 and the second electrode EL2. The plurality of the organic layers may include a hole transport region HTR, an emission layer EML, and an electron transport region ETR.

The organic electroluminescence device 10 of an embodiment may include a monoamine compound of an embodiment of the present disclosure in at least one organic layer among the plurality of organic layers disposed between the first electrode EL1 and the second electrode EL2. For example, the monoamine compound of an embodiment may be included in a hole transport region HTR.

When compared with FIG. 1, FIG. 2 shows a cross-sectional view of the organic electroluminescence device 10 of an embodiment, wherein the hole transport region HTR includes a hole injection layer HIL and a hole transport layer HTL, and the electron transport region ETR includes an electron injection layer EIL and an electron transport layer ETL. In addition, when compared with FIG. 1, FIG. 3 shows a cross-sectional view of the organic electroluminescence device 10 of an embodiment, wherein the hole transport region HTR includes a hole injection layer HIL, a hole transport layer HTL, and an electron blocking layer EBL, and the electron transport region ETR includes an electron injection layer EIL, an electron transport layer ETL, and a hole blocking layer HBL. In the organic electroluminescence device 10 of an embodiment, the hole transport layer HTL may include the monoamine compound of an embodiment.

A hole transport layer HTL may include a plurality of sub hole transport layers in the organic electroluminescence device 10 of an embodiment, and the monoamine compound of an embodiment may be included in the sub hole transport layer that is adjacent to an emission layer EML.

The first electrode EL1 may have conductivity. For example, the first electrode EL1 may be formed using a metal alloy or a conductive compound. The first electrode EL1 may be an anode. In an embodiment, the first electrode EL1 may be a pixel electrode. The first electrode EL1 may be a transmissive electrode, a transflective electrode, or a reflective electrode. If the first electrode EL1 is the transmissive electrode, the first electrode EL1 may be formed using a transparent metal oxide such as indium tin oxide (ITO), indium zinc oxide (IZO), zinc oxide (ZnO), and/or indium tin zinc oxide (ITZO). If the first electrode EL1 is the transflective electrode or the reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). Also, the first electrode EL1 may have a structure of a plurality of layers including a reflective layer or a transflective layer formed using any of the above materials, and a transmissive conductive layer formed using ITO, IZO, ZnO, and/or ITZO. For example, the first electrode EL1 may have a structure of ITO/Ag/ITO, without limitation. The thickness of the first electrode EL1 may be from about 1,000 Å to about 10,000 Å, for example, from about 1,000 Å to about 3,000 Å.

The hole transport region HTR is provided on the first electrode EL1. The hole transport region HTR may include at least one of a hole injection layer HIL, a hole transport layer HTL, a hole buffer layer, or an electron blocking layer EBL.

The hole transport region HTR may have a single layer formed using a single material, a single layer formed using a plurality of different materials, or a multilayer structure including a plurality of layers formed using a plurality of different materials.

For example, the hole transport region HTR may have the structure of a single layer such as a hole injection layer HIL, or a hole transport layer HTL, and/or may have a structure of a single layer formed using a hole injection material and a hole transport material. In some embodiments, the hole transport region HTR may have a structure of a single layer formed using a plurality of different materials, or a structure laminated from the first electrode EL1 of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer EBL, without limitation.

The hole transport region HTR may be formed using one or more suitable methods, such as a vacuum deposition method, a spin coating method, a cast method, a Langmuir-Blodgett (LB) method, an inkjet printing method, a laser printing method, and/or a laser induced thermal imaging (LITI) method, without limitation.

In the organic electroluminescence device 10 of an embodiment, at least one organic layer among the plurality of organic layers between the first electrode EL1 and the second electrode EL2 may include the monoamine compound represented by Formula 1. For example, in the organic electroluminescence device 10 of an embodiment, a hole transport region HTR may include the monoamine compound represented by Formula 1:

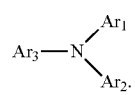

Formula 1

In Formula 1, at least one selected from $Ar_1$, $Ar_2$ and $Ar_3$ is represented by the following Formula 2:

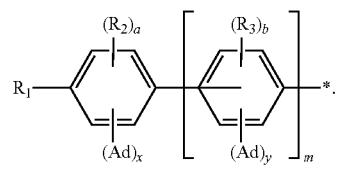

Formula 2

In Formula 1, at least one selected from $Ar_1$, $Ar_2$ and $Ar_3$ may be represented by Formula 2 and the remaining ones of $Ar_1$, $Ar_2$ and $Ar_3$ may be each independently a substituted or unsubstituted aryl group having 6 to 30 carbon atoms for forming a ring, or a substituted or unsubstituted heteroaryl group having 2 to 30 carbon atoms for forming a ring. For example, any one or two selected from among $Ar_1$, $Ar_2$ and $Ar_3$ may be represented by Formula 2, and the remaining ones may be substituted or unsubstituted aryl groups having 6 to 30 carbon atoms for forming a ring, or substituted or unsubstituted heteroaryl groups having 2 to 30 carbon atoms for forming a ring.

For example, any one selected from among $Ar_1$, $Ar_2$ and $Ar_3$ may be represented by Formula 2, and the remaining two from among $Ar_1$, $Ar_2$ and $Ar_3$ may be each independently a substituted or unsubstituted aryl group having 6 to 30 carbon atoms for forming a ring, or a substituted or unsubstituted heteroaryl group having 2 to 30 carbon atoms for forming a ring. In some embodiments, two selected from among $Ar_1$, $Ar_2$ and $Ar_3$ may be represented by Formula 2, and the remaining one from among $Ar_1$, $Ar_2$ and $Ar_3$ may be a substituted or unsubstituted aryl group having 6 to 30 carbon atoms for forming a ring, or a substituted or unsubstituted heteroaryl group having 2 to 30 carbon atoms for forming a ring.

In Formula 2, $R_1$ to $R_3$ may be each independently a hydrogen atom, a deuterium atom, a halogen atom, a cyano group, a substituted or unsubstituted silyl group, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring.

In Formula 2, "m" may be 0 or 1, "a", "b", "x" and "y" may be each independently an integer of 0 to 4.

In Formula 2, if "a", "b", "x" and "y" are integers of 2 or more, a respective plurality of $R_1$, $R_2$, $R_3$, and "Ad" groups may be the same, or at least one among the respective plurality may be different. For example, in one monoamine compound unit, each of the $R_1$ to $R_3$ and "Ad" groups may be present in plural and the plurality of each of the $R_1$, $R_2$, $R_3$, and "Ad" may be the same or different from each other.

In Formula 2, if "m" is 0, "x" may be an integer of 1 or more, and if "m" is 1, "x+y" may be an integer of 1 or more.

In Formula 2, "Ad" may be represented by the following Formula 3:

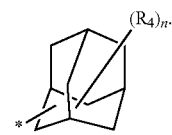

Formula 3

In Formula 3, $R_4$ may be a hydrogen atom, a deuterium atom, a halogen atom, a cyano group, a substituted or unsubstituted silyl group, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring; and "n" may be an integer of 0 to 15.

In the monoamine compound of an embodiment, at least one selected from $Ar_1$, $Ar_2$, and $Ar_3$ may include an adamantane moiety

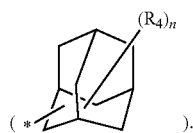

In addition, the monoamine compound of an embodiment may include both an arylamine moiety

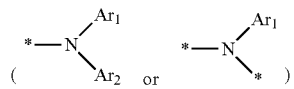

and an adamantane moiety

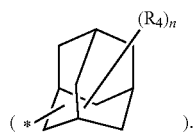

When the monoamine compound of an embodiment includes an arylamine moiety and an adamantane moiety, and is used as a material for the organic layer of an organic electroluminescence device, the balance of holes and electrons in a device may be kept appropriately.

In the monoamine compound of an embodiment, the arylamine moiety may play the role of transporting holes, and the adamantane moiety may play the role of inhibiting (or reducing) the transport of electrons. That is, by controlling the bonding position of the arylamine moiety and the adamantane moiety in the monoamine compound of an embodiment as shown in Formula 1, the balance of holes and electrons may be maintained in an organic electroluminescence device, and the concentration of excitons in an emission layer may increase to improve light emission efficiency.

In the monoamine compound of an embodiment, represented by Formula 1, $Ar_1$, $Ar_2$, and $Ar_3$ that are not represented by Formula 2 may be the same or different from each other. When $Ar_1$, $Ar_2$, and $Ar_3$ are each independently selected from a substituted or unsubstituted aryl group having 6 to 30 carbon atoms for forming a ring and a substituted or unsubstituted heteroaryl group having 2 to 30 carbon atoms for forming a ring, the substituent of substituted aryl and heteroaryl groups may be a halogen atom, a cyano group, an alkyl group having 1 to 20 carbon atoms, an alkoxy group having 1 to 10 carbon atoms, an aryloxy group having 1 to 20 carbon atoms, an alkylthio group having 1 to 10 carbon atoms, an arylthio group having 1 to 20 carbon atoms, a triarylsilyl group having 18 to 50 carbon atoms, or an adamantyl group.

In the monoamine compound of an embodiment, "m" in Formula 2 may be 0 or 1. If "m" is 0, a phenyl group substituted with at least one adamantly group may bond directly to the nitrogen atom of an arylamine moiety.

That is, in Formula 2, if "m" is 0, "x" may be an integer of 1 or more. For example, if "m" is 0, "x" may be 1 or 2, and in this case, "Ad" in Formula 2 may be bonded to the phenyl group so as to achieve ortho or meta position with respect to the nitrogen atom of the arylamine moiety.

In Formula 2, if "m" is 1, "x+y" may be an integer of 1 or more. In the monoamine compound of an embodiment, "x+y" may be an integer of 1 to 3.

For example, if "m" is 1 and "x+y" is 1, "x" may be 1 and "y" may be 0, or "x" may be 0 and "y" may be 1. If "m" is 1 and "x+y" is 2, both "x" and "y" may be 1, "x" may be 2 and "y" may be 0, or "x" may be 0 and "y" may be 2. If "m" is 1 and "x+y" is 3, "x" may be 2 and "y" may be 1, or "x" may be 1 and "y" may be 2.

In case where "m" is 1, "Ad" represented by Formula 3 may be bonded to a phenyl group or a biphenyl group to achieve ortho or meta position with respect to the nitrogen atom of the arylamine moiety. In the monoamine compound of an embodiment, $R_1$ may be a hydrogen atom or an unsubstituted phenyl group.

In the monoamine compound of an embodiment, $R_2$ and $R_3$ may each independently be an alkyl group having 1 to 10 carbon atoms or a hydrogen atom. For example, both $R_2$ and $R_3$ may be hydrogen atoms.

In Formula 3, $R_4$ may be a hydrogen atom, a deuterium atom, a halogen atom, a cyano group, a substituted or unsubstituted silyl group, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring. If "n" is an integer of 2 or more in Formula 3, a plurality of $R_4$ groups may be the same, or at least one $R_4$ group may be different. For example, $R_4$ may be a hydrogen atom. That is, the substituent represented by Formula 3 may be an unsubstituted adamantyl group.

In the monoamine compound of an embodiment, "Ad" represented by Formula 3 may be represented by the following Formula 3-1 or Formula 3-2:

Formula 3-1

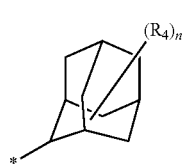

Formula 3-2

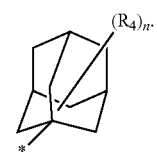

In Formula 3-1 and Formula 3-2, $R_4$ and "n" are the same as defined in Formula 3. For example, $R_4$ may be a hydrogen atom.

The monoamine compound of an embodiment may have at least one adamantyl group. That is, the monoamine compound of an embodiment may include at least one adamantyl group that is bonded to the nitrogen atom of an amine group in ortho or meta position on a phenylene group or a divalent biphenyl group.

Formula 1 may be represented by the following Formula 1-A or Formula 1-B:

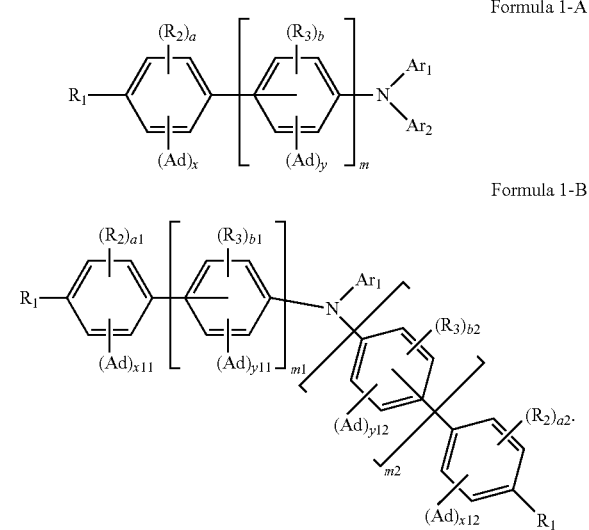

In Formula 1-B, "m1" and "m2" are each independently 0 or 1, and "a1", "a2", "b1", "b2", "x11", "x12", "y11", and "y12" are each independently an integer of 0 to 4. In Formula 1-B, if "m1" is 0, "x11" is an integer of 1 or more, if "m1" is 1, "x11+y11" is an integer of 1 or more, if "m2" is 0, "x12" is an integer of 1 or more, and if "m2" is 1, "x12+y12" is an integer of 1 or more.

In the monoamine compound of an embodiment, represented by Formula 1-A or Formula 1-B, $Ar_1$ and $Ar_2$ may be the same or different. When $Ar_1$, $Ar_2$, and $Ar_3$ are each independently selected from a substituted or unsubstituted aryl group having 6 to 30 carbon atoms for forming a ring, or a substituted or unsubstituted heteroaryl group having 2 to 30 carbon atoms for forming a ring, the substituent of the substituted aryl and heteroaryl groups may be a halogen atom, a cyano group, an alkyl group having 1 to 20 carbon atoms, an alkoxy group having 1 to 10 carbon atoms, an aryloxy group having 1 to 20 carbon atoms, an alkylthio group having 1 to 10 carbon atoms, an arylthio group having 1 to 20 carbon atoms, a triarylsilyl group having 18 to 50 carbon atoms, or an adamantyl group.

For example, those from among $Ar_1$, $Ar_2$, and $Ar_3$ that are not represented by Formula 2, may be each independently an aryl group having 6 to 30 carbon atoms for forming a ring, wherein the aryl group is unsubstituted or substituted with at least one selected from a halogen atom, a cyano group, an alkyl group having 1 to 20 carbon atoms, an alkoxy group having 1 to 10 carbon atoms, an aryloxy group having 1 to 20 carbon atoms, an alkylthio group having 1 to 10 carbon atoms, an arylthio group having 1 to 20 carbon atoms, a triarylsilyl group having 18 to 50 carbon atoms, and an adamantyl group.

In some embodiments, those from among $Ar_1$, $Ar_2$, and $Ar_3$ that are not represented by Formula 2, may be each independently a heteroaryl group having 2 to 30 carbon atoms for forming a ring, wherein the heteroaryl group is unsubstituted or substituted with at least one selected from a halogen atom, a cyano group, an alkyl group having 1 to 20 carbon atoms, an alkoxy group having 1 to 10 carbon atoms, an aryloxy group having 1 to 20 carbon atoms, an alkylthio group having 1 to 10 carbon atoms, an arylthio group having 1 to 20 carbon atoms, a triarylsilyl group having 18 to 50 carbon atoms, and an adamantyl group.

Those from among $Ar_1$, $Ar_2$, and $Ar_3$ that are not represented by Formula 2 may be each independently a substituted or unsubstituted phenyl group, a substituted or unsubstituted biphenyl group, a substituted or unsubstituted terphenyl group, a substituted or unsubstituted phenanthryl group, a substituted or unsubstituted dibenzofuran group, or a substituted or unsubstituted dibenzothiophene group.

When $Ar_1$, $Ar_2$, and $Ar_3$ (which are not represented by Formula 2) are each independently a substituted or unsubstituted aryl group having 6 to 30 carbon atoms for forming a ring or a substituted or unsubstituted heteroaryl group having 2 to 30 carbon atoms for forming a ring, the substituent of the aryl group and/or the heteroaryl group may be a substituted or unsubstituted alkyl group having 1 to 10 carbon atoms, an unsubstituted phenyl group, an unsubstituted naphthyl group, an unsubstituted biphenyl group, an unsubstituted terphenyl group, an unsubstituted cyclohexyl group, an unsubstituted adamantyl group, a triphenylsilyl group, or a trimethylsilyl group.

For example, $Ar_1$, $Ar_2$, and $Ar_3$ (which are not represented by Formula 2) may be each independently a substituted or unsubstituted phenyl group, provided that the monoamine compound of an embodiment does not include a case where any one from among $Ar_1$, $Ar_2$, and $Ar_3$ is represented by Formula 2 and the remaining two are unsubstituted phenyl groups. In case where $Ar_1$, $Ar_2$, and $Ar_3$ (which are not represented by Formula 2) are each independently a substituted or unsubstituted phenyl group, the substituent may be an unsubstituted phenyl group, an unsubstituted naphthyl group, an unsubstituted biphenyl group, an unsubstituted terphenyl group, an unsubstituted adamantyl group, a triphenylsilyl group, or a trimethylsilyl group.

In addition, in Formula 1-A or Formula 1-B, $Ar_1$ and $Ar_2$ may be each independently a substituted or unsubstituted biphenyl group. For example, in case where $Ar_1$ and $Ar_2$ are each independently a substituted or unsubstituted biphenyl group, the substituent may be a substituted or unsubstituted alkyl group having 1 to 20 carbon atoms, an unsubstituted phenyl group, an unsubstituted naphthyl group, an unsubstituted cyclohexyl group, or an unsubstituted adamantyl group.

In the monoamine compound represented by Formula 1-A or Formula 1-B, $Ar_1$ and $Ar_2$ may be each independently represented by any one from among the following Formula A-1 to Formula A-20:

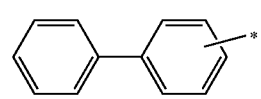

A-1

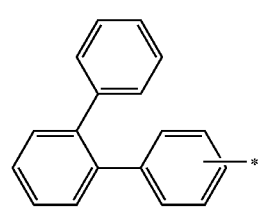

A-2

-continued
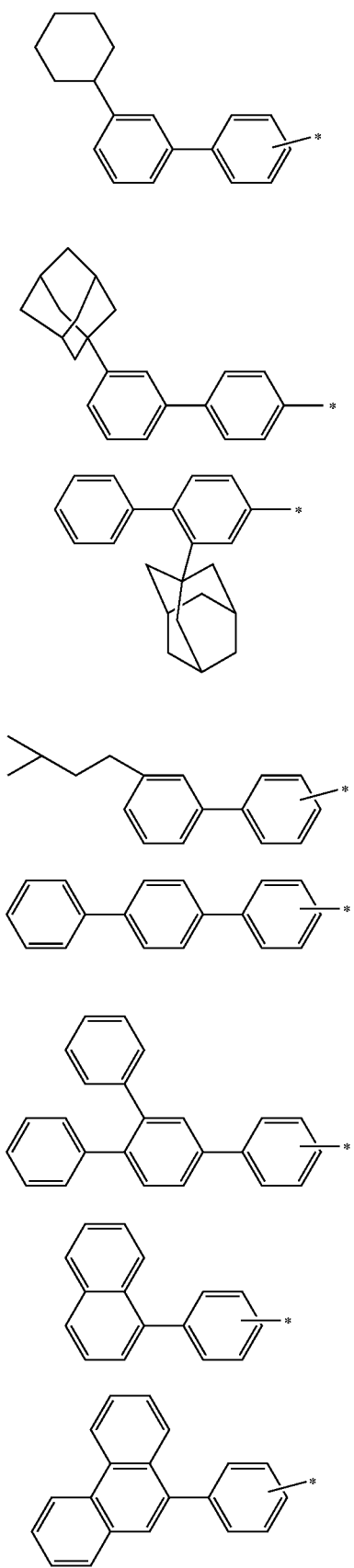
A-3
A-4
A-5
A-6
A-7
A-8
A-9
A-10
-continued
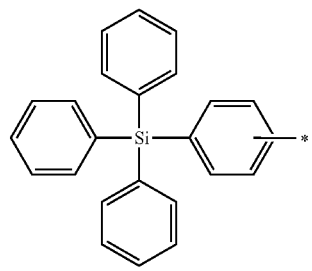
A-11
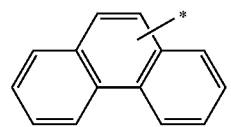
A-12
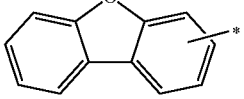
A-13
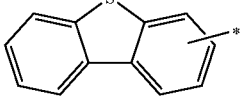
A-14
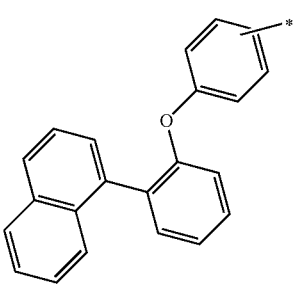
A-15
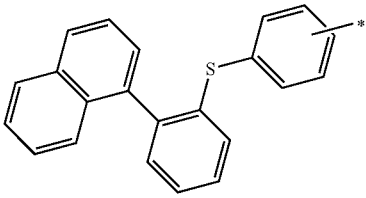
A-16
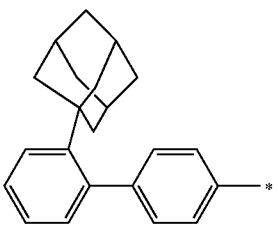
A-17
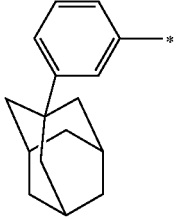
A-18

A-19

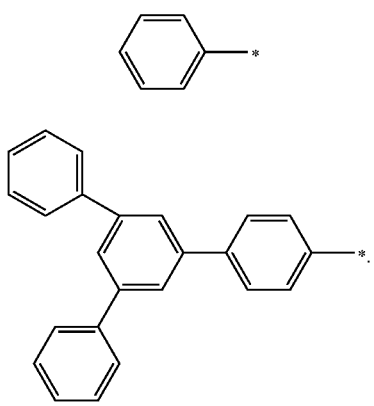

A-20

The monoamine compound of an embodiment, represented by Formula 1-A, may be represented by any one from among the following Formula 1-1 to Formula 1-3:

Formula 1-1

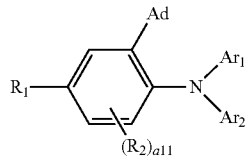

Formula 1-2

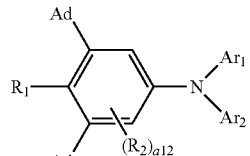

Formula 1-3

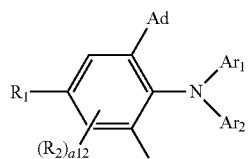

Formula 1-1 represents Formula 1-A where "m" is 0, and Formula 1-2 and Formula 1-3 represent Formula 1 where "m" is 1. In Formula 1-1 to Formula 1-3, $R_1$ to $R_3$, "a", "b", "x", "y", $Ar_1$, $Ar_2$, and "Ad" may be the same as described in Formulae 1 to 3.

Formula 1-1 may be represented by any one from among the following Formula 1-1a to Formula 1-1e:

Formula 1-1a

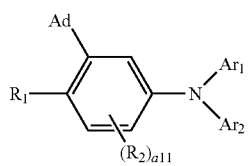

Formula 1-1b

Formula 1-1c

Formula 1-1d

Formula 1-1e

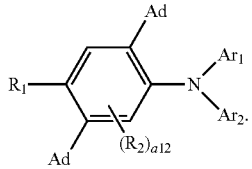

In Formula 1-1a and Formula 1-1b, "a11" is an integer of 0 to 3, in Formula 1-1c, Formula 1-1d, and Formula 1-1e, "a12" is an integer of 0 to 2. If "a11" or "a12" is an integer of 2 or more, a plurality of corresponding $R_2$ groups may be the same, or at least one among them may be different.

In Formula 1-1a to Formula 1-1e, $R_1$, $R_2$, $Ar_1$, $Ar_2$, and "Ad" may be the same as described in connection with Formulae 1 to 3.

The monoamine compounds of Formula 1-1a and Formula 1-1b represent cases where one adamantyl group represented by Formula 3 is substituted on a phenyl group. Formula 1-1c, Formula 1-1d, and Formula 1-1e represent cases where two adamantyl groups represented by Formula 3 are substituted on a phenyl group.

In addition, Formula 1-1a and Formula 1-1c represent cases where an adamantyl group represented by Formula 3 and the nitrogen atom of an arylamine group are bonded in meta position (e.g., configuration), and Formula 1-1b and Formula 1-1d represent cases where an adamantyl group represented by Formula 3 and the nitrogen atom of an arylamine group are bonded in ortho position. Formula 1-1e represents a case where two adamantyl groups represented by Formula 3 and the nitrogen atom of an arylamine group are respectively bonded in ortho position and meta position.

In the monoamine compound of an embodiment, represented by Formula 1-1c and Formula 1-1d, two adamantyl groups represented by Formula 3 may be substituted in symmetrical positions on a phenyl group.

The monoamine compound of an embodiment, represented by Formula 1-2 may be represented by any one among the following Formula 1-2a to Formula 1-2c:

Formula 1-2a

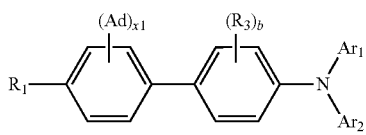

Formula 1-2b

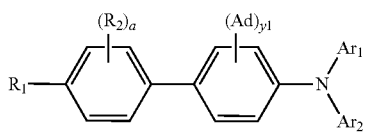

Formula 1-2c

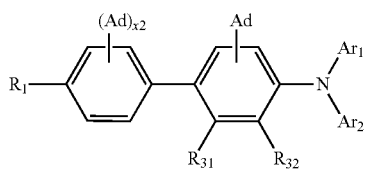

In Formula 1-2a, "x1" is 1 or 2; in Formula 1-2b, "y1" is 1 or 2; and in Formula 1-2c, "x2" is 1 or 2.

Formula 1-2a represents a case where "Ad" represented by Formula 3 is substituted on a phenyl group which is separated from (e.g., is indirectly bonded to) the arylamine moiety in Formula 1-2, and Formula 1-2b represents a case where "Ad" represented by Formula 3 is substituted on a phenyl group which is adjacent to (e.g., is directly bonded to) the arylamine moiety in Formula 1-2. Formula 1-2c represents a case where "Ad" represented by Formula 3 is substituted on each of the two phenyl groups of a biphenyl group bonded to the arylamine moiety in Formula 1-2.

In Formula 1-2a to Formula 1-2c, "a", "b", $R_1$, $R_2$, $R_3$, $Ar_1$, $Ar_2$, and "Ad" may be the same as described in connection with Formulae 1 to 3.

In Formula 1-2c, $R_{31}$ and $R_{32}$ may each independently be a hydrogen atom, a deuterium atom, a halogen atom, a cyano group, a substituted or unsubstituted silyl group, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring. For example, $R_{31}$ and $R_{32}$ may be hydrogen atoms.

The monoamine compound of an embodiment, represented by Formula 1-3 may be represented by any one among the following Formula 1-3a to Formula 1-3c:

Formula 1-3a

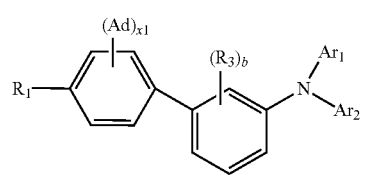

Formula 1-3b

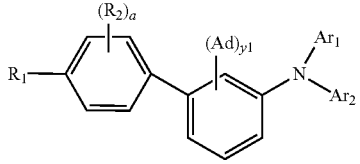

Formula 1-3c

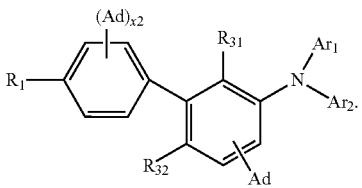

In Formula 1-3a, "x1" is 1 or 2; in Formula 1-3b, "y1" is 1 or 2; and in Formula 1-3c, "x2" is 1 or 2.

Formula 1-3a represents a case where "Ad" represented by Formula 3 is substituted on a phenyl group which is separated from (e.g., is indirectly bonded to) the arylamine moiety in Formula 1-3, and Formula 1-3b represents a case where "Ad" represented by Formula 3 is substituted on a phenyl group which is adjacent to (e.g., is directly bonded to) the arylamine moiety in Formula 1-3. Formula 1-3c represents a case where "Ad" represented by Formula 3 is substituted on each of the two phenyl groups of a biphenyl group bonded to the arylamine moiety in Formula 1-3.

In Formula 1-3a to Formula 1-3c, "a", "b", $R_1$, $R_2$, $R_3$, $Ar_1$, $Ar_2$, and "Ad" are the same as described in connection with Formulae 1 to 3.

In Formula 1-3c, $R_{31}$ and $R_{32}$ may each independently be a hydrogen atom, a deuterium atom, a halogen atom, a cyano group, a substituted or unsubstituted silyl group, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring. For example, $R_{31}$ and $R_{32}$ may be hydrogen atoms.

The monoamine compound of an embodiment represented by Formula 1 may be represented by any one among the compounds in Compound Group 1 and Compound Group 2:

Compound Group 1

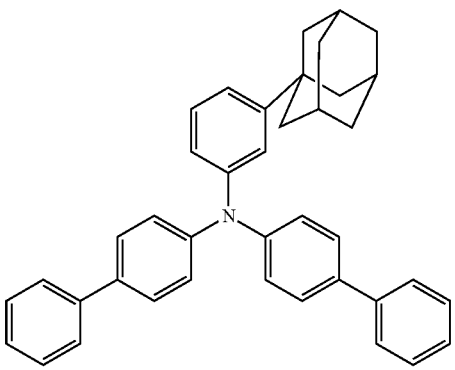

1

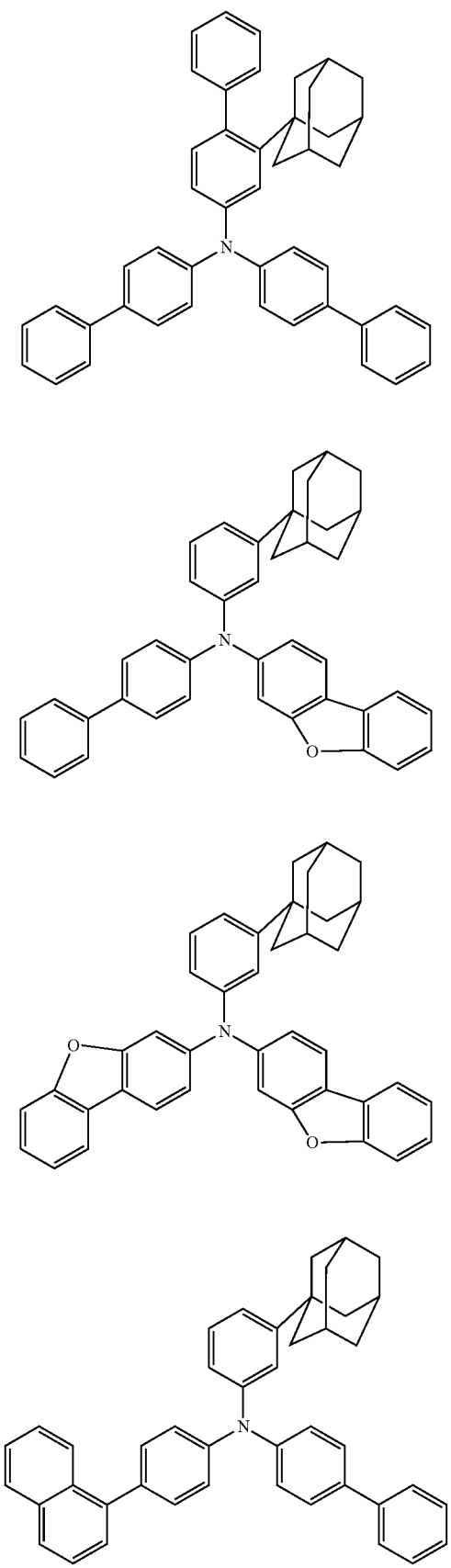
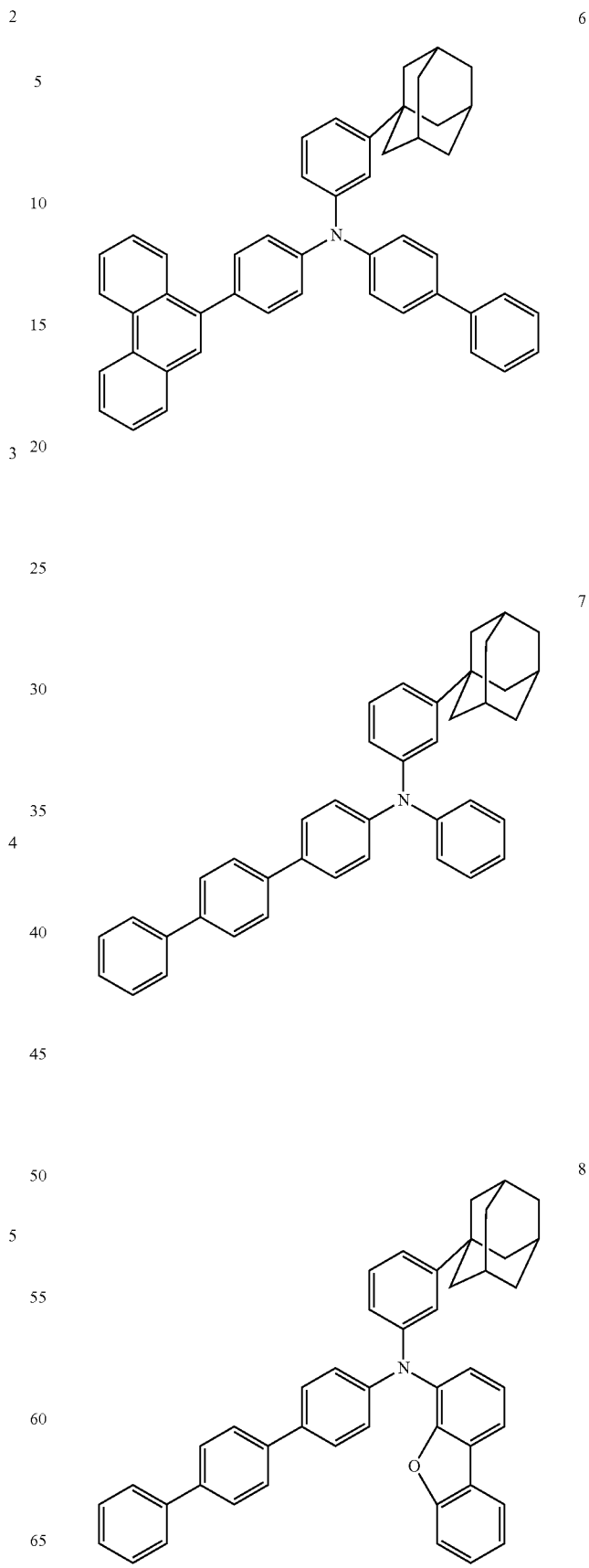

9
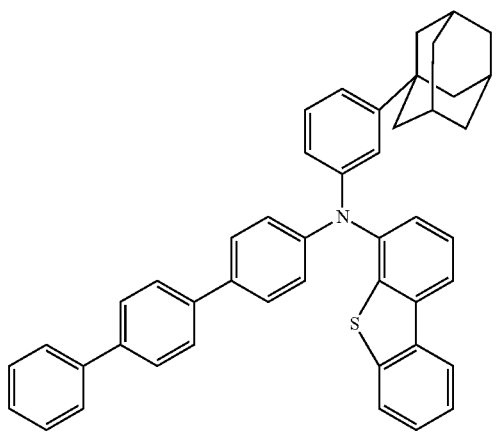
10
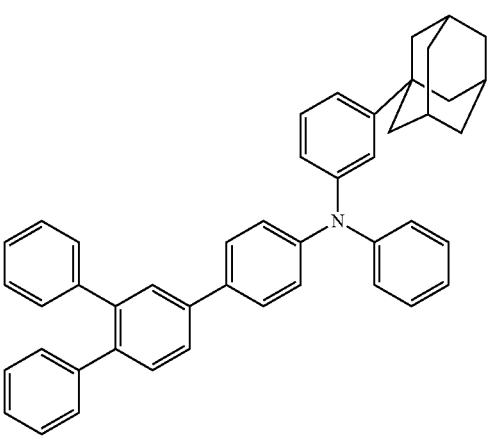
11
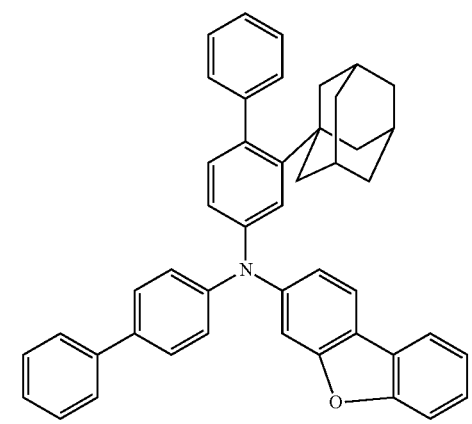
12
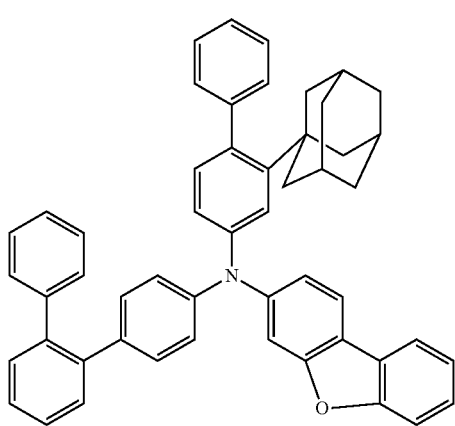
13
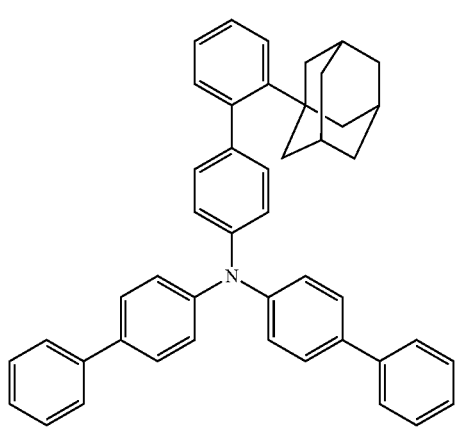
14
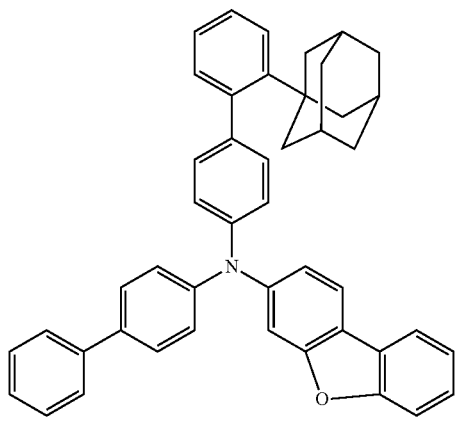

15
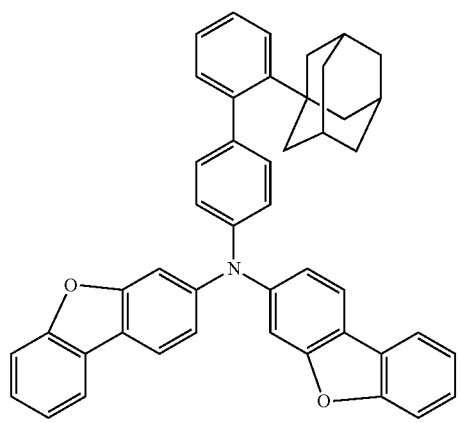
16
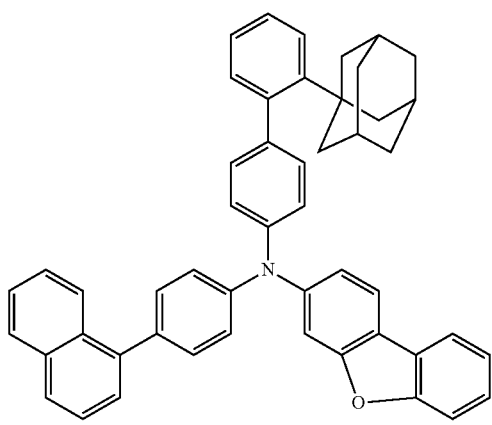
17
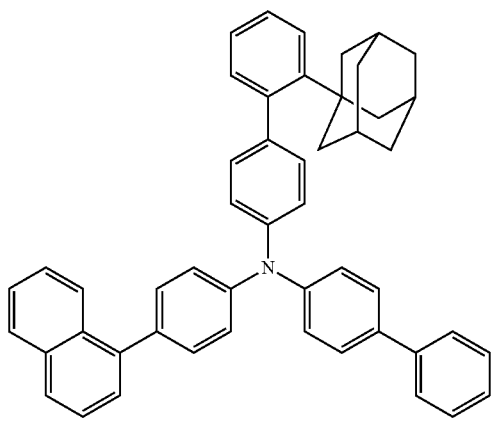
18
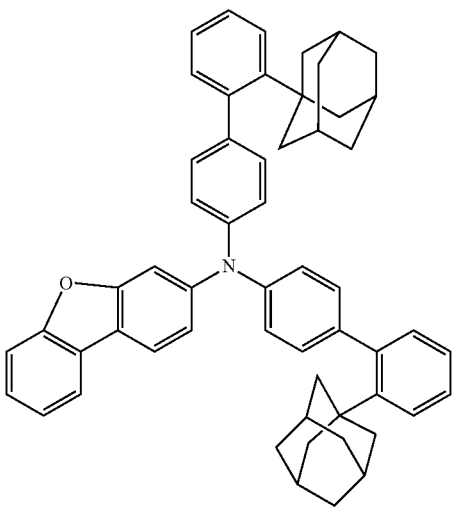
19
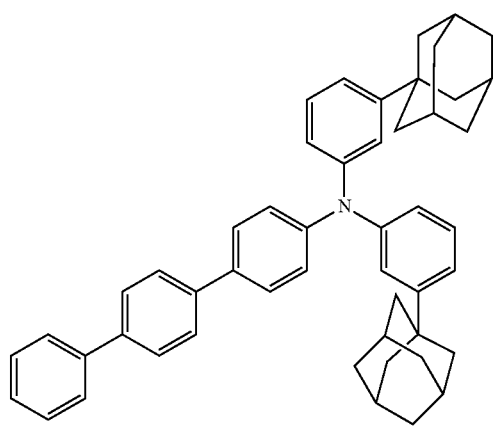
20
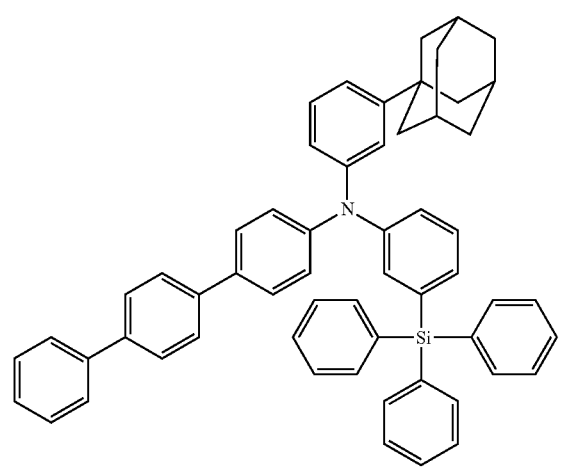

21
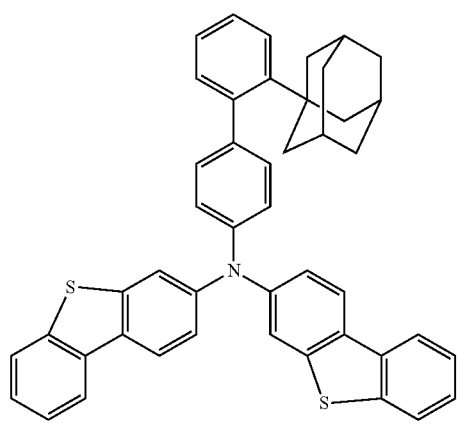
22
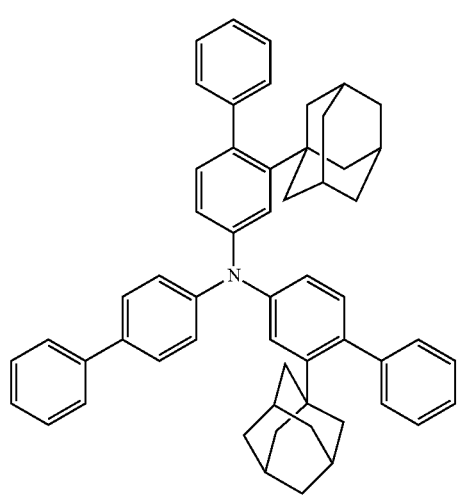
23
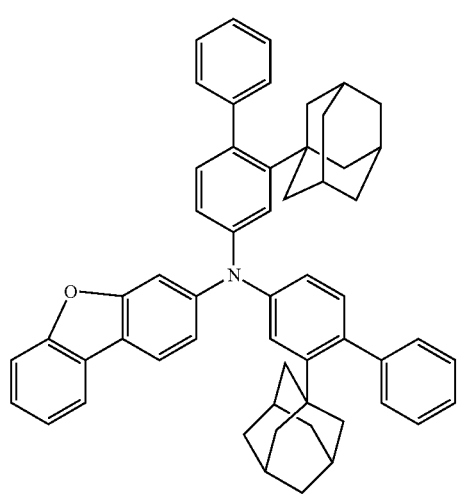
24
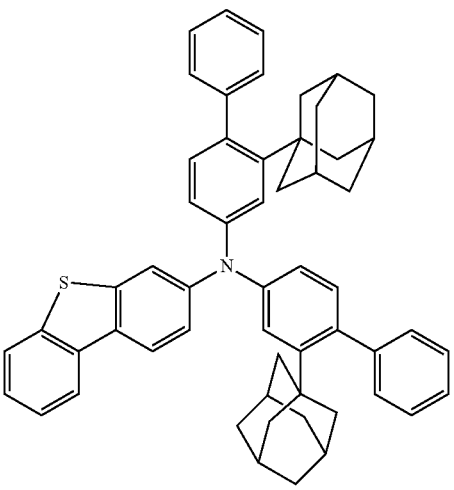
25
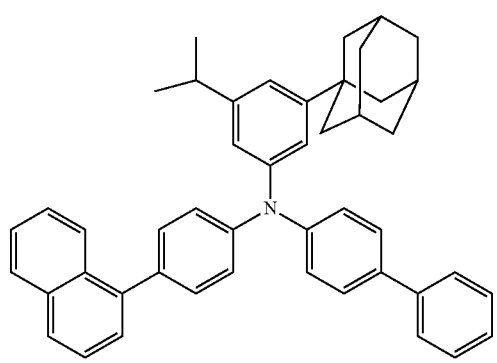
26
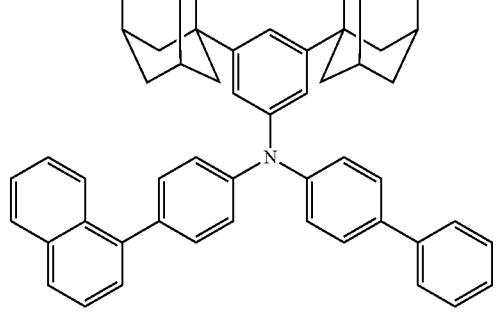
27
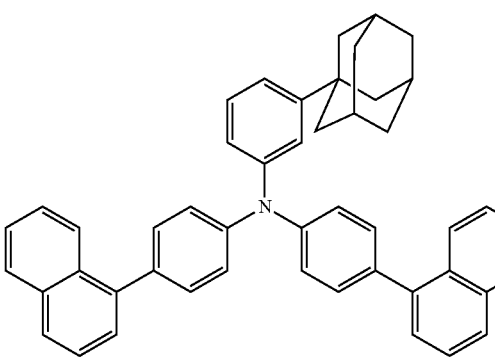

28
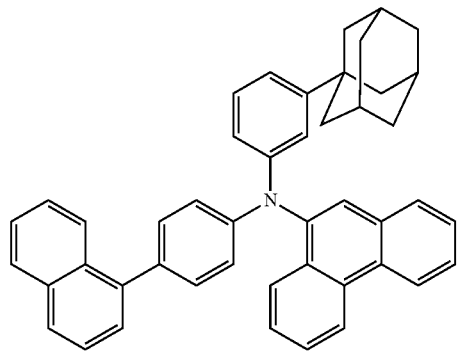
29
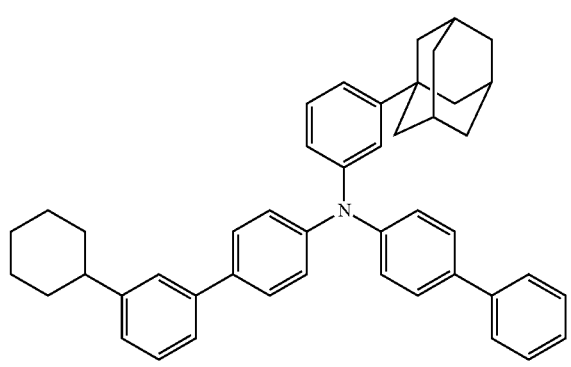
30
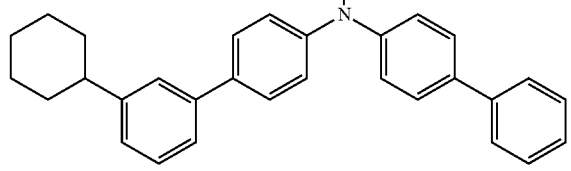
31
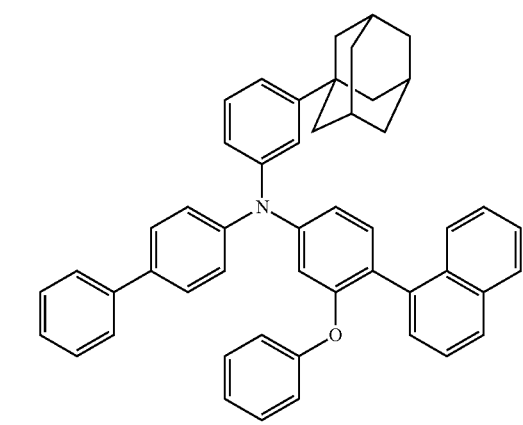
32
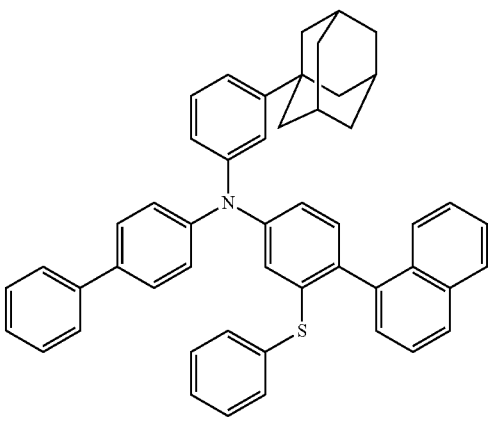
Compound Group 2
33
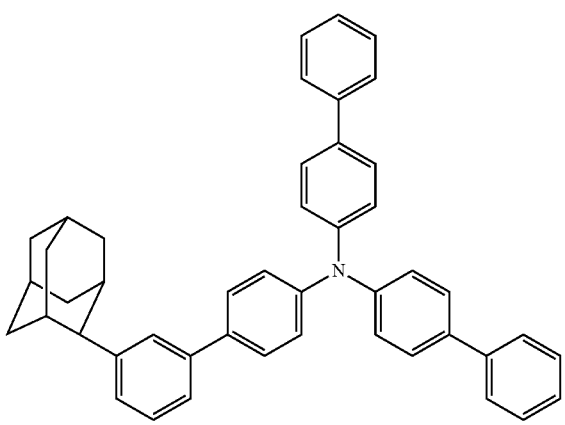
34
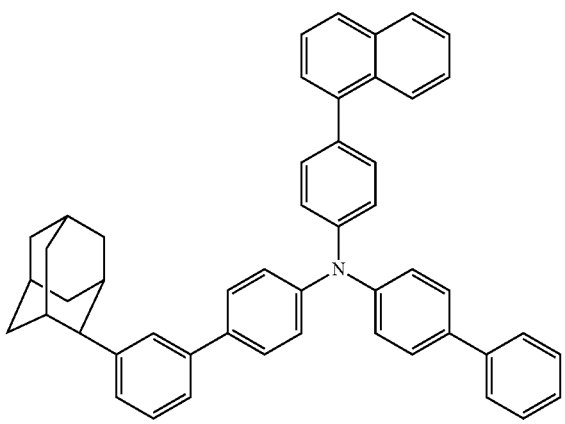

35
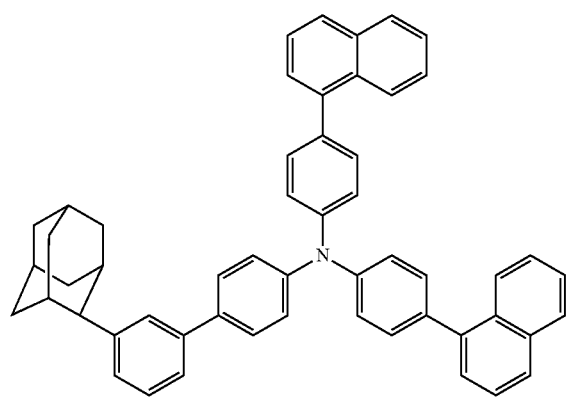
36
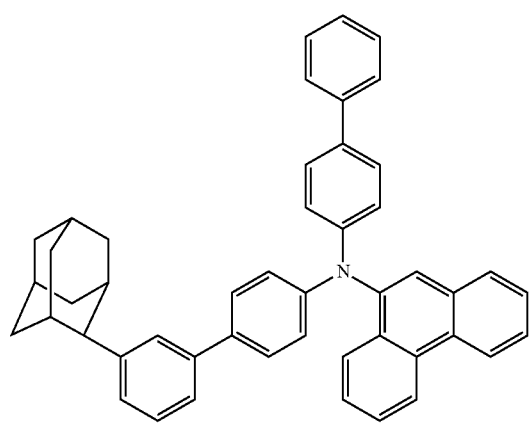
37
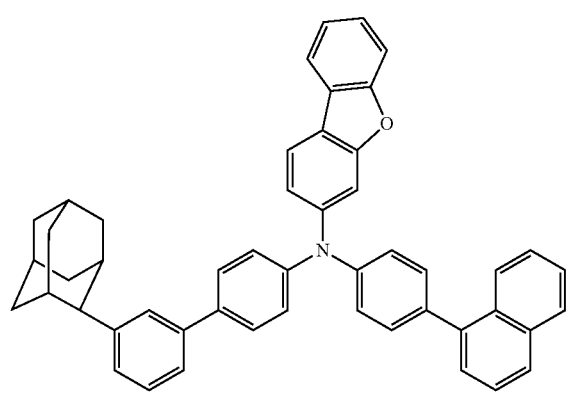
38
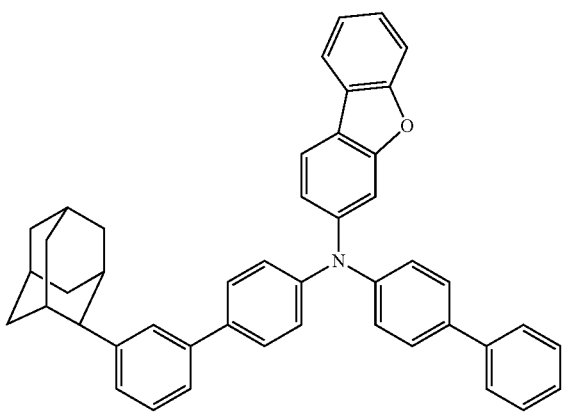
39
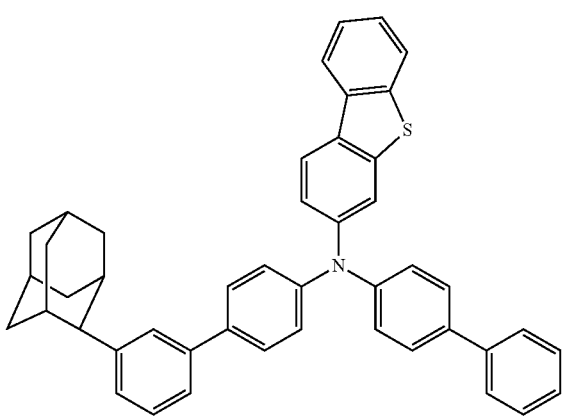
40
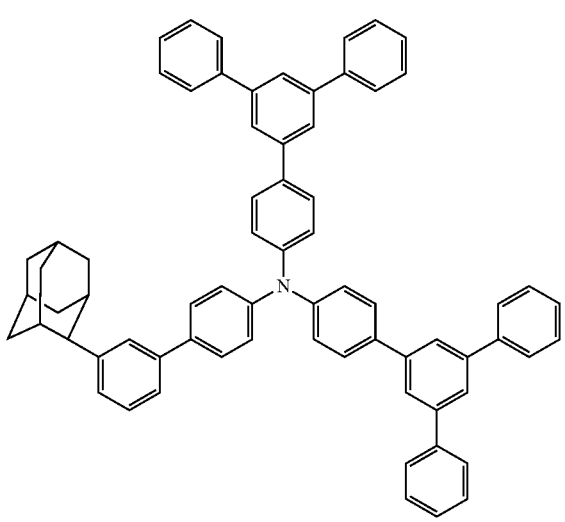

41
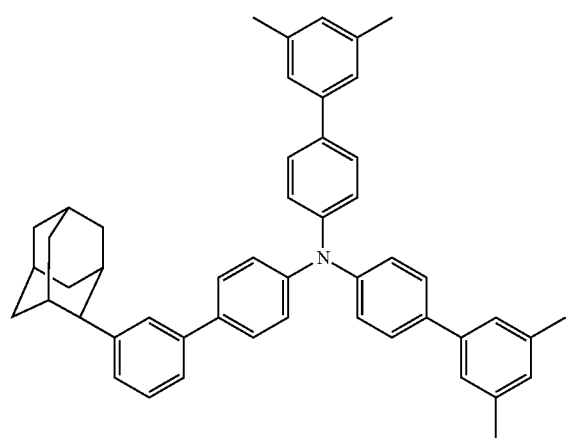
42
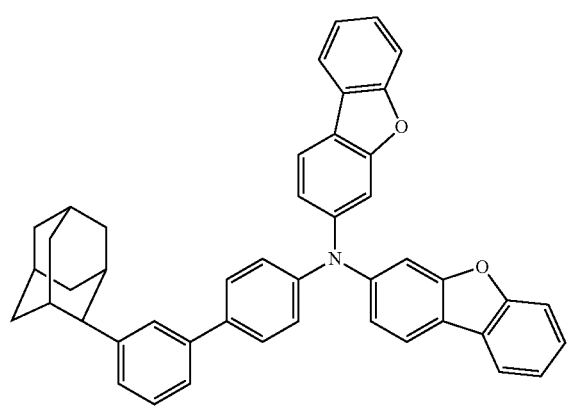
43
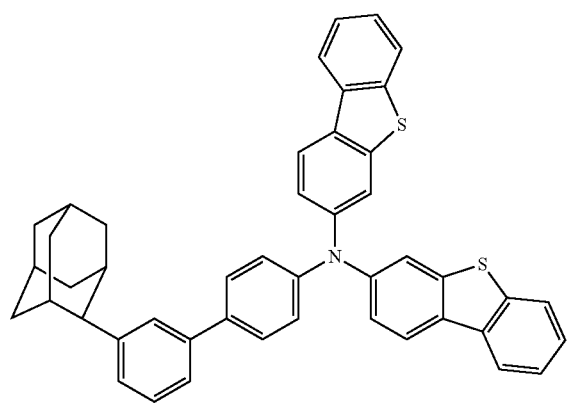
44
45
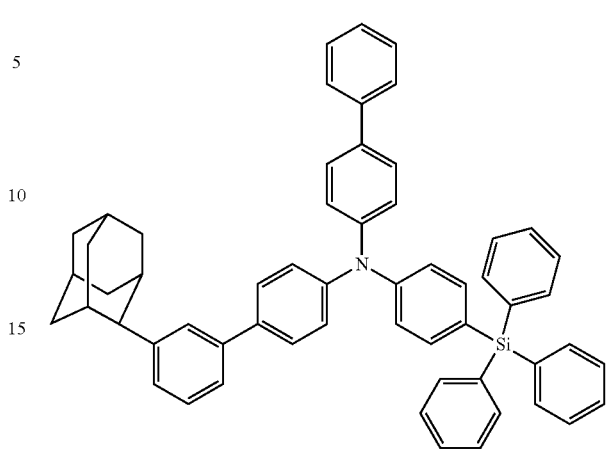
46
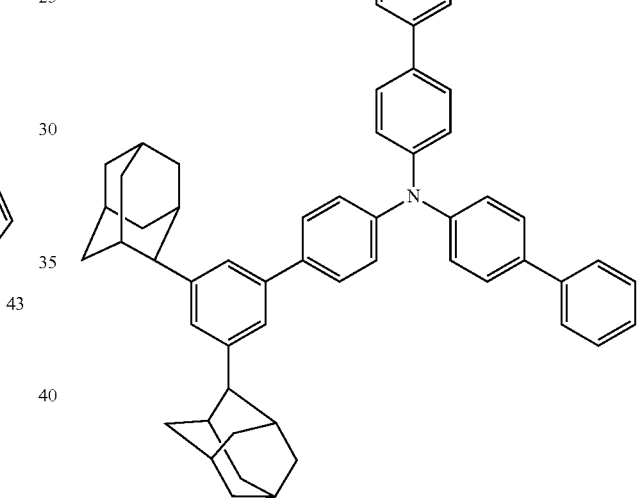
47
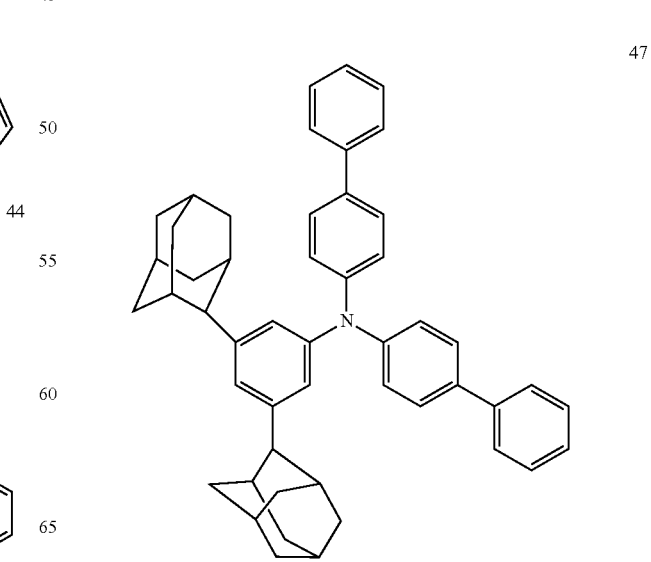

48
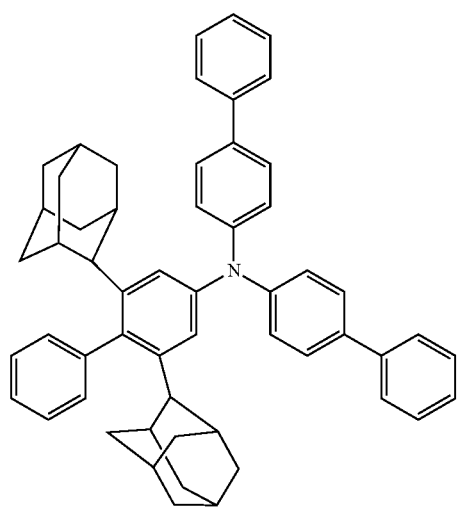
49
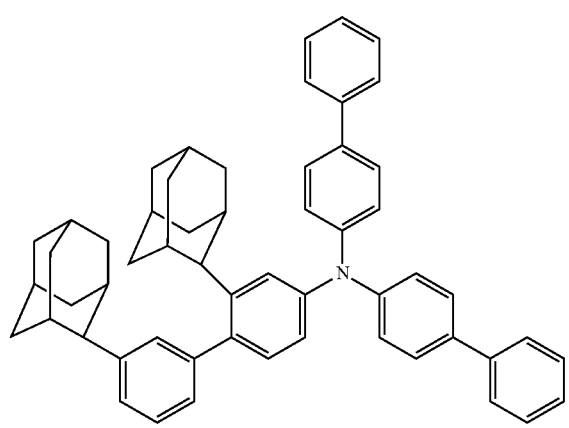
50
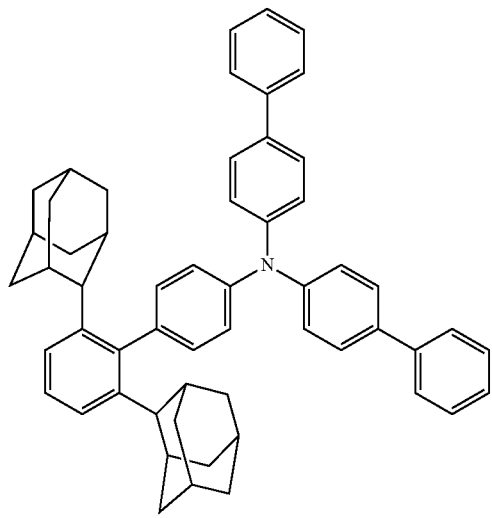
51
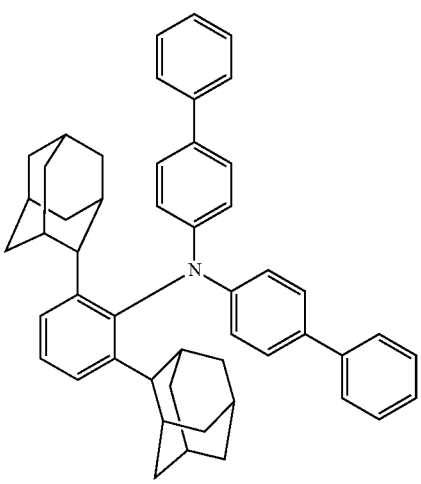
52
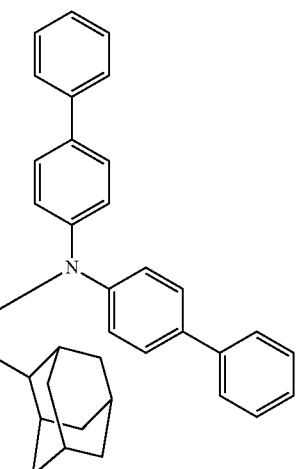
53
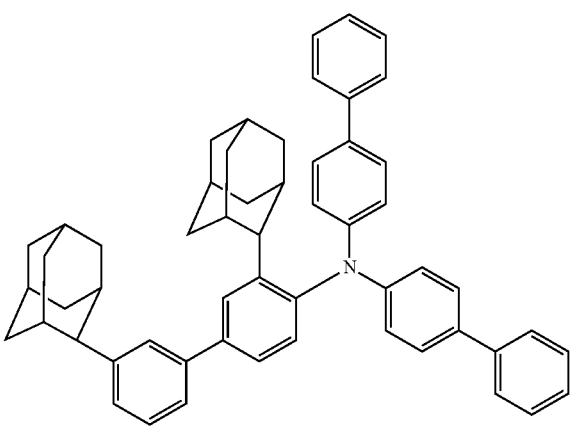

54
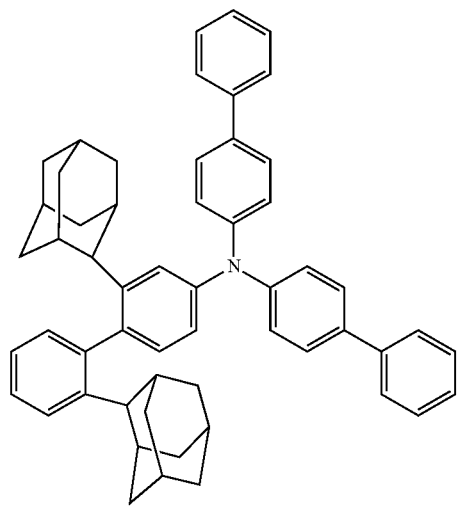
55
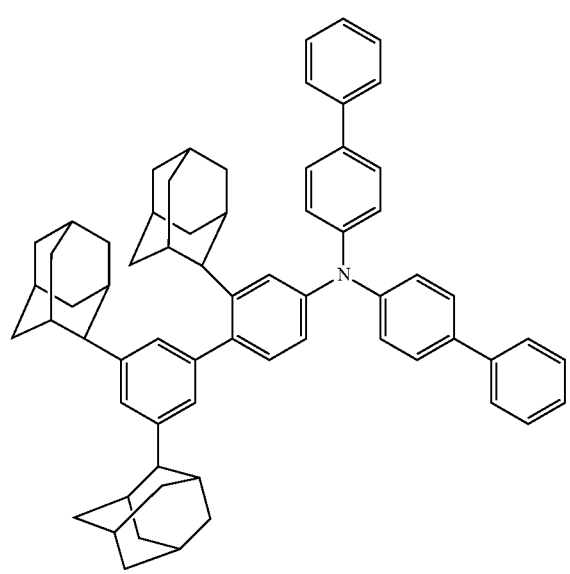
56
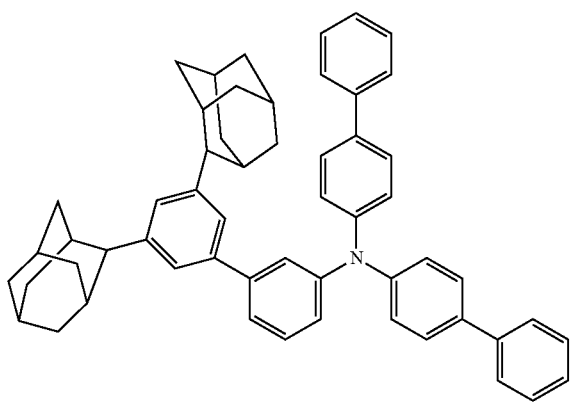
57
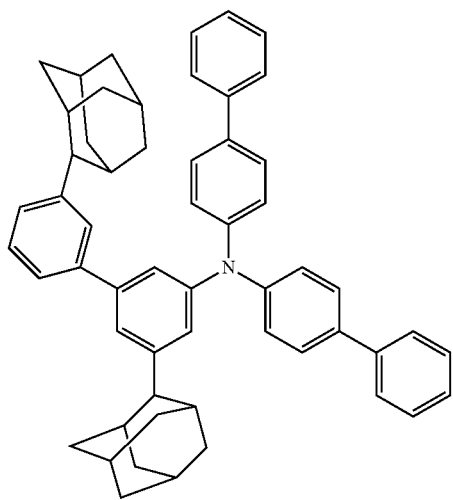
58
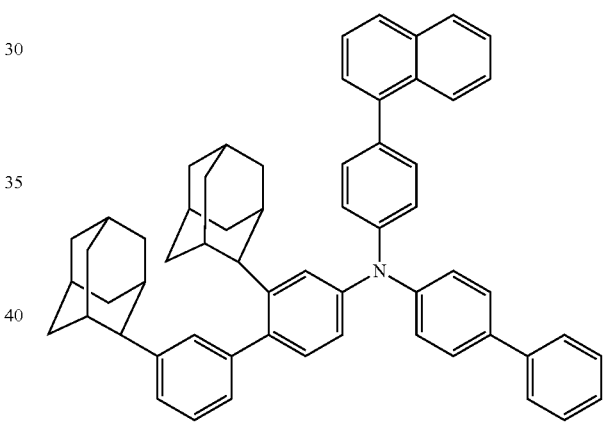
59
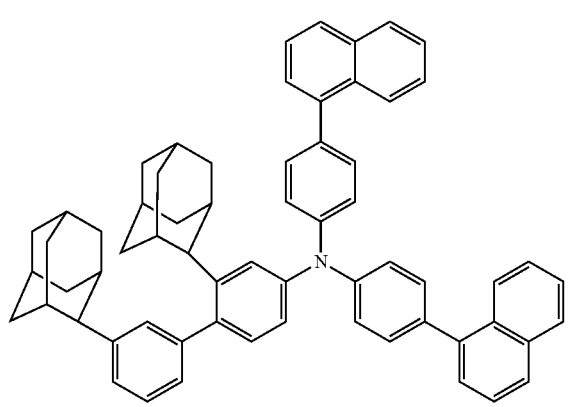

77
-continued
60
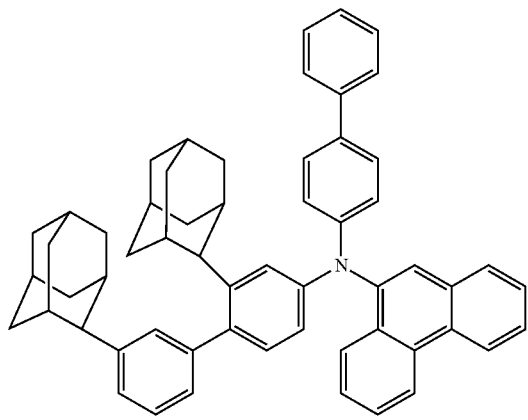
61
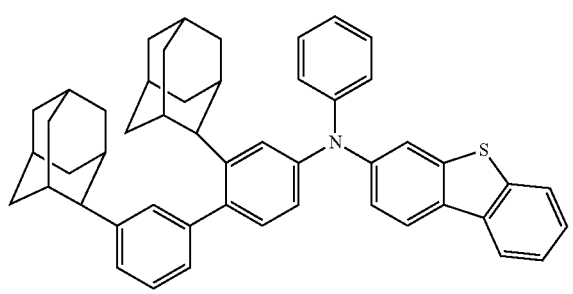
62
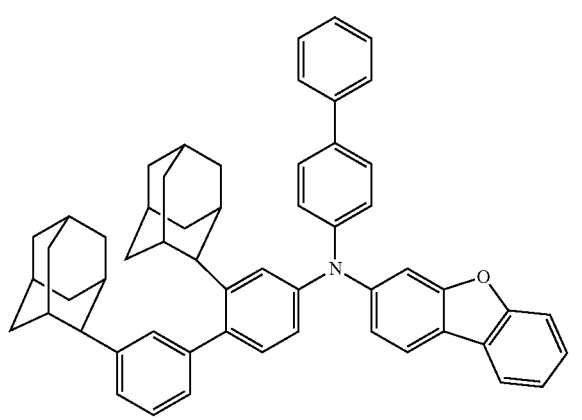
63
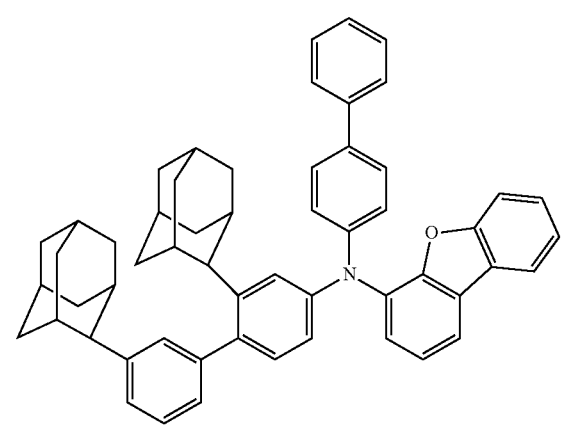
78
-continued
64
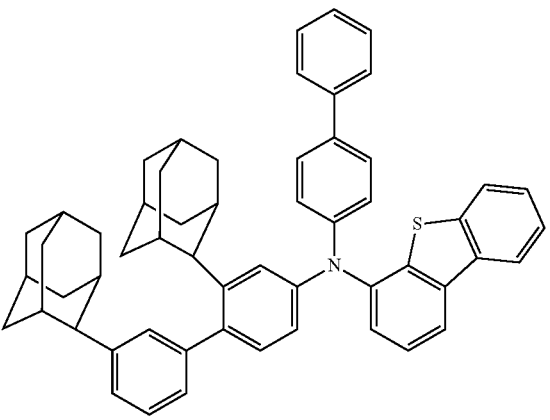
65
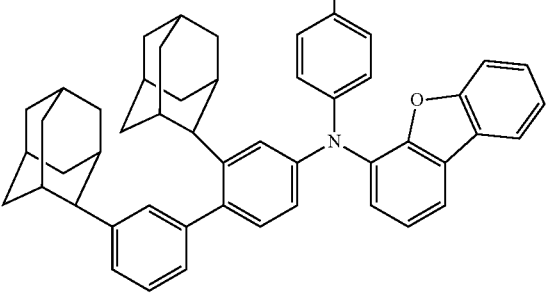
66
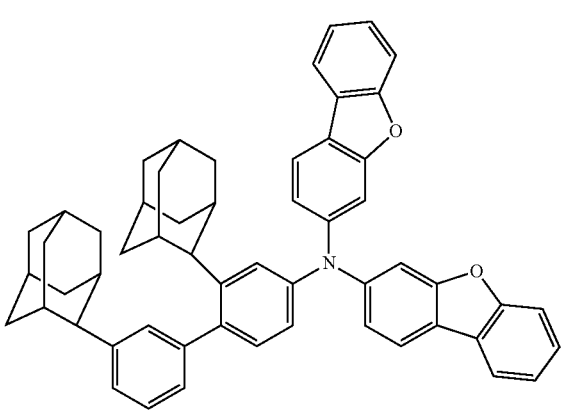

79
-continued
67
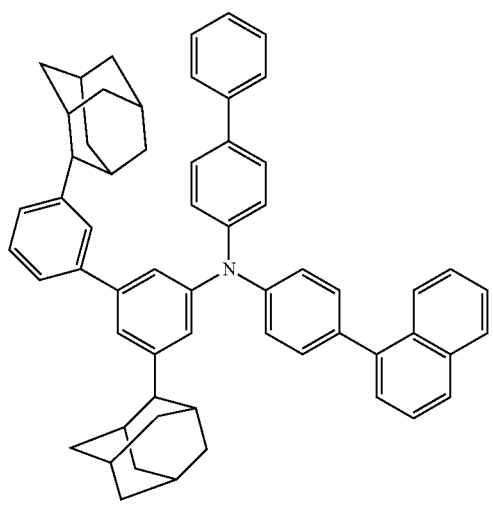
68
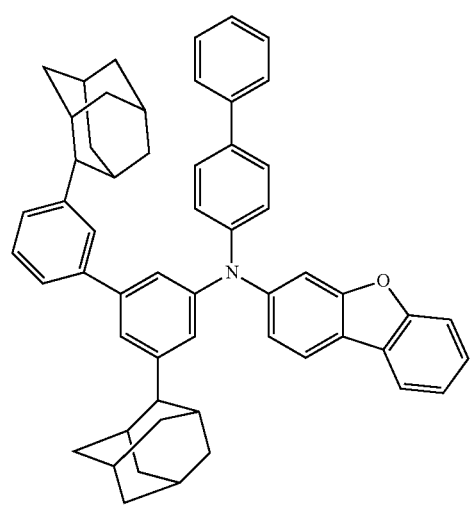
69
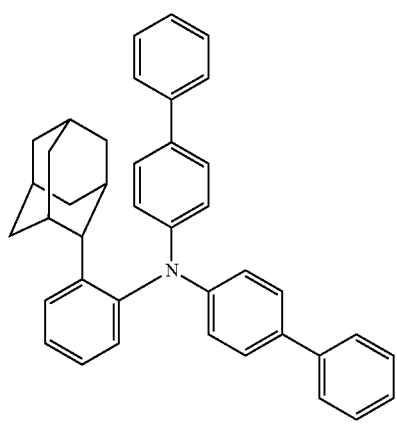
80
-continued
70
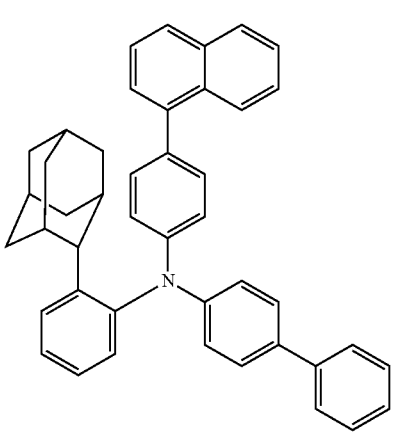
71
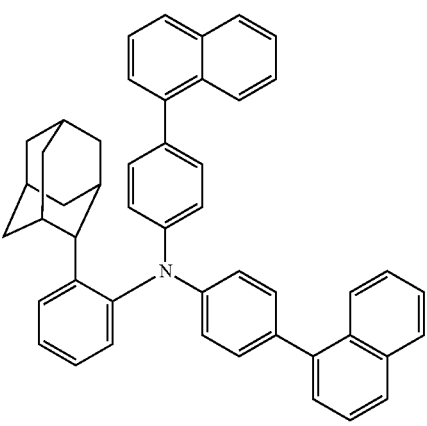
72
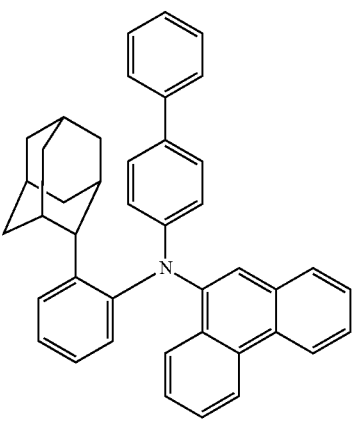

73
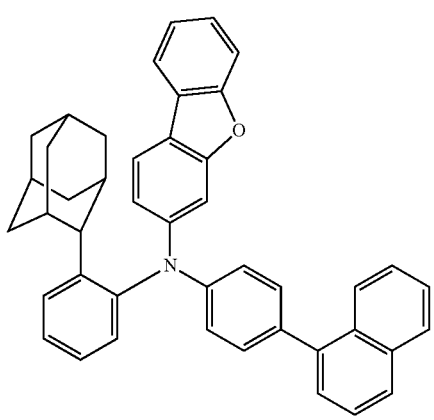
74
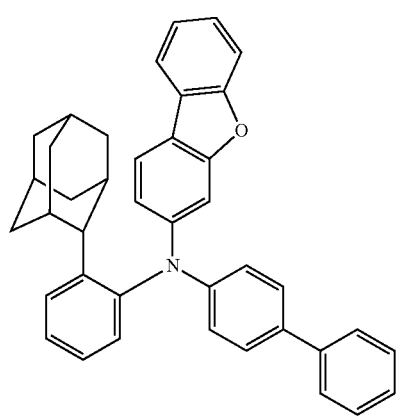
75
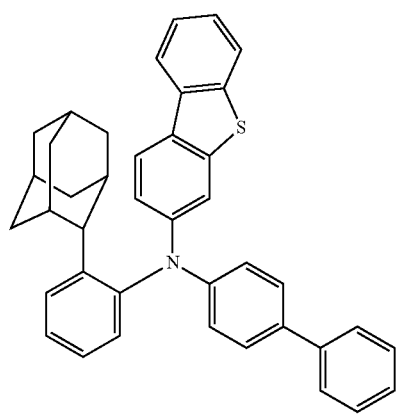
76
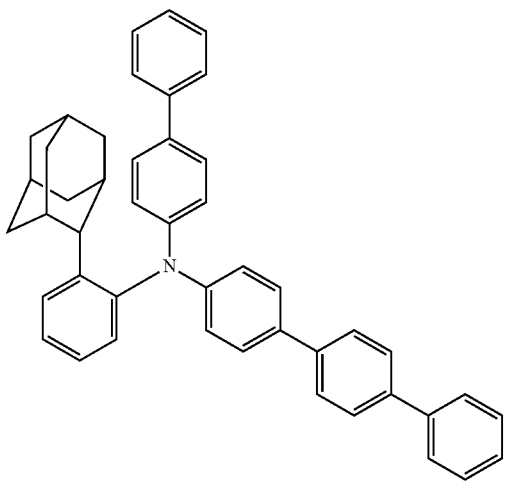
77
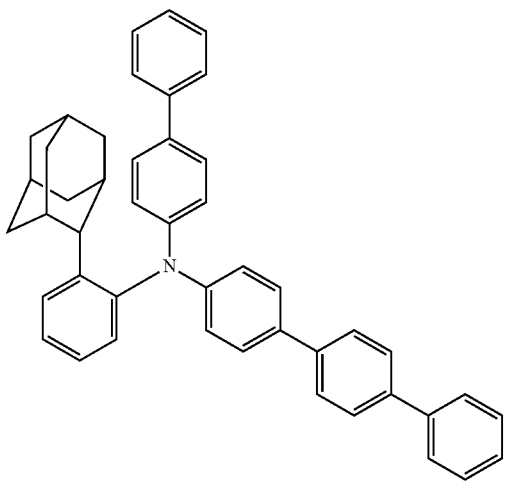
78
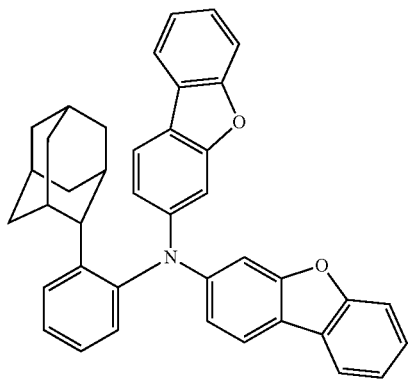

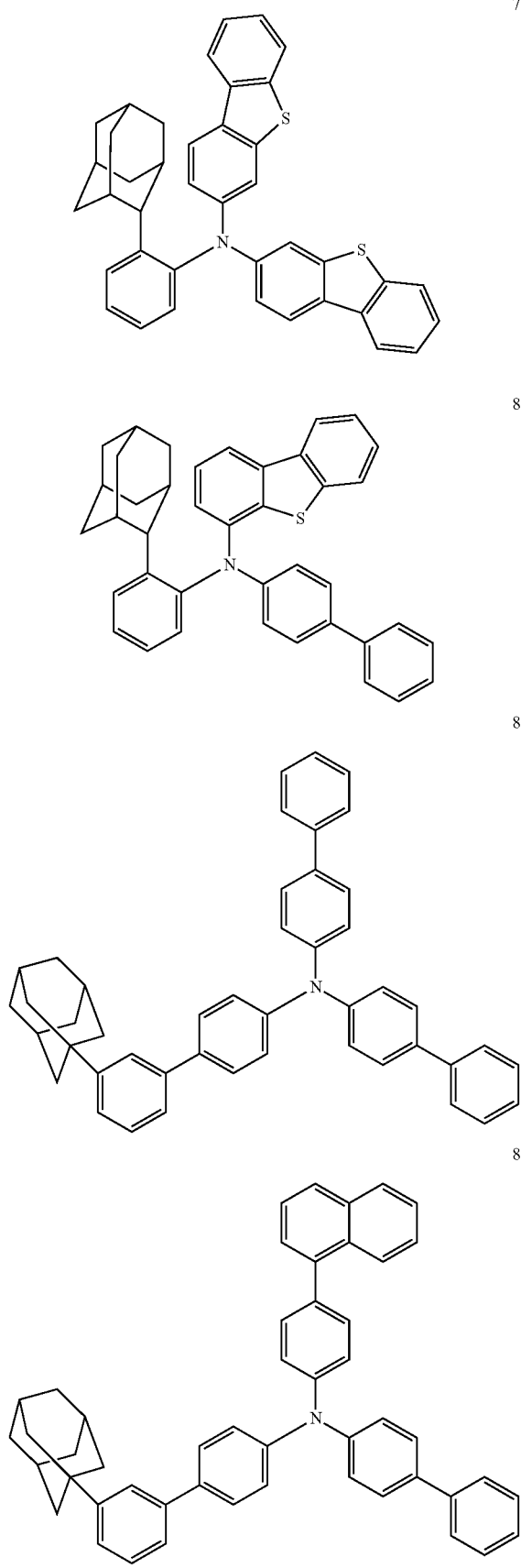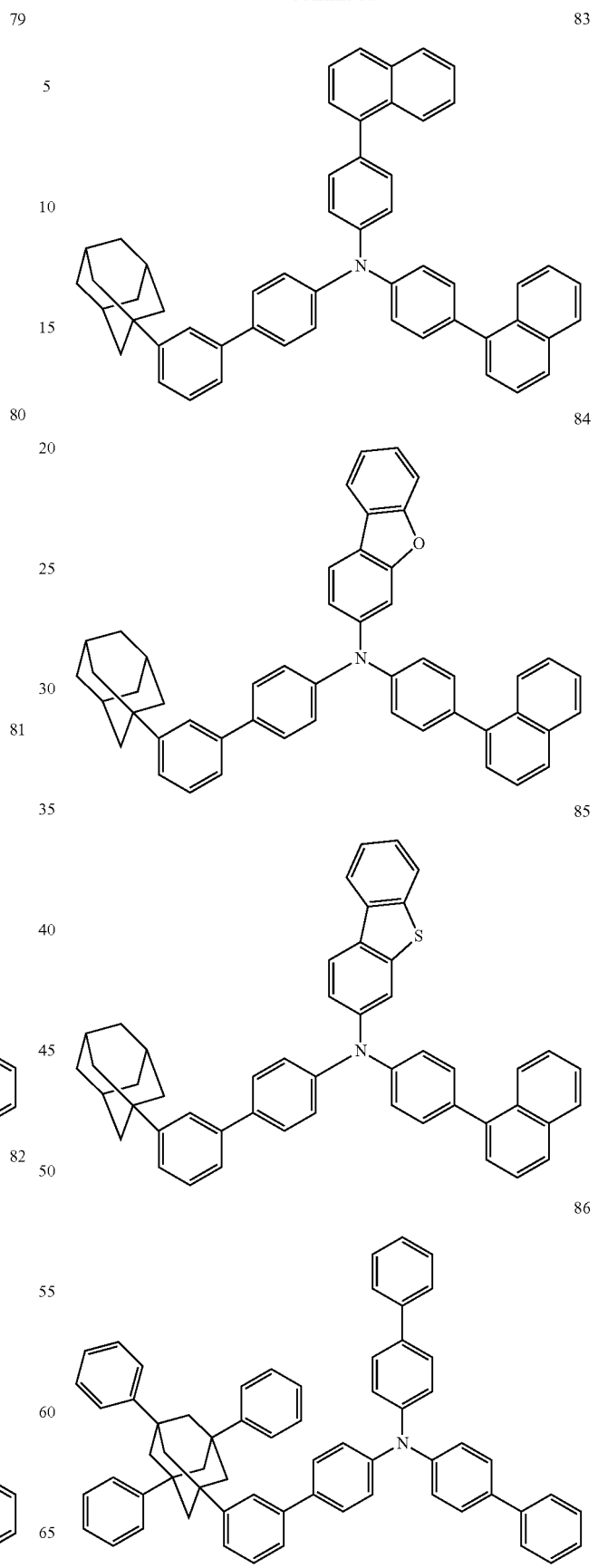

87
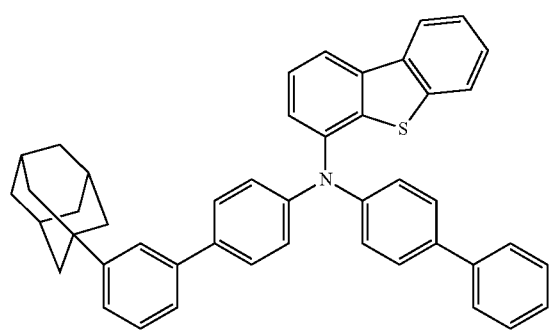
88
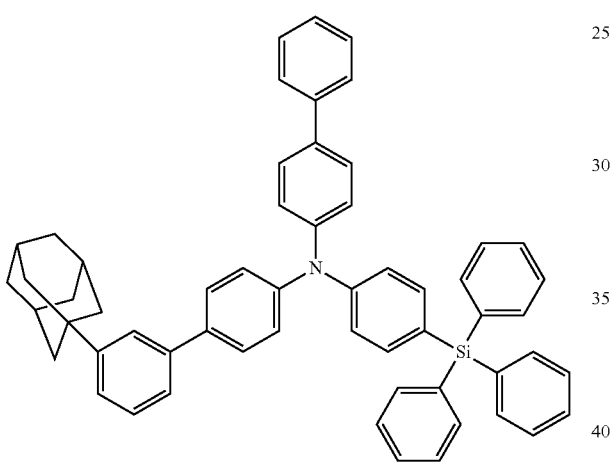
89
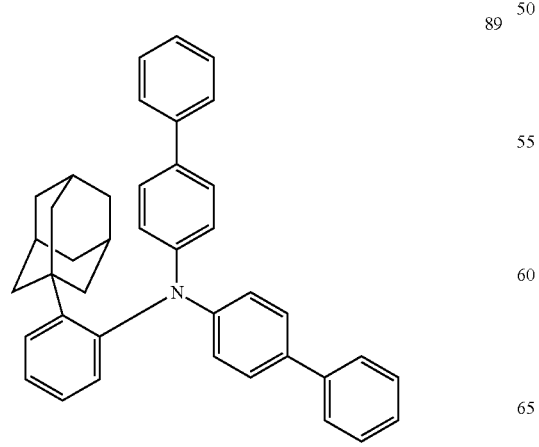
90
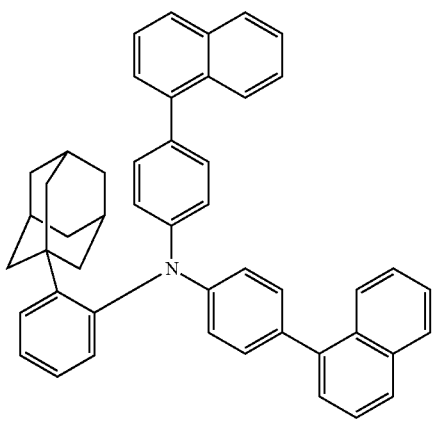
91
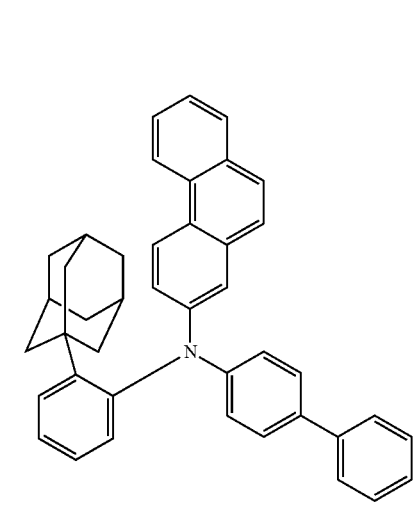
92
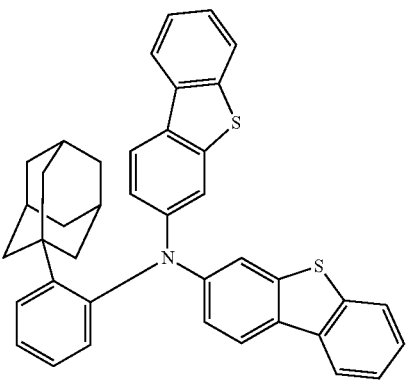

-continued

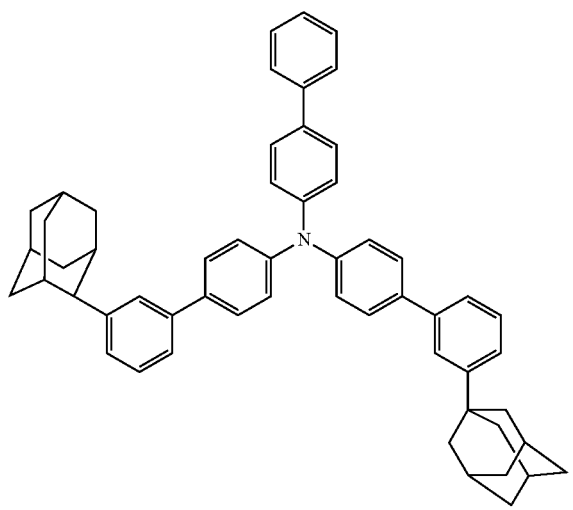

93

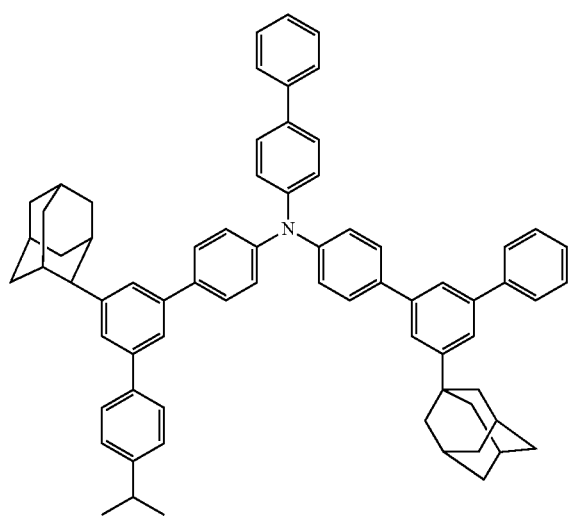

94

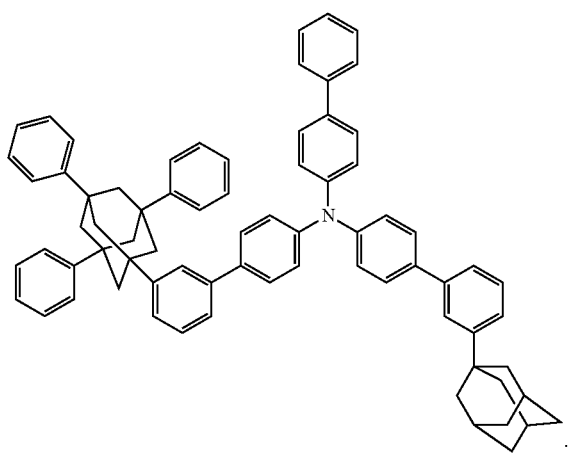

95

The above-described monoamine compound of an embodiment includes at least one adamantyl group as a substituent and may be used as a material for an organic electroluminescence device to facilitate good heat resistance and excellent (or suitable) light emission efficiency. In the monoamine compound of an embodiment, an adamantyl group is bonded at ortho or meta position with respect to the nitrogen atom of an arylamine group, and excellent (or suitable) heat resistance may be achieved while maintaining excellent (or suitable) hole transport capacity. In addition, the monoamine compound of an embodiment has excellent (or suitable) hole transport capacity and may play the role of blocking (or reducing) electrons, and thus, if used in an organic electroluminescence device, may improve the light emission efficiency of the organic electroluminescence device even further.

In the organic electroluminescence device 10 of an embodiment as shown in FIGS. 1 to 3, a hole transport region HTR may include one or two or more monoamine compounds represented in Compound Group 1 and Compound Group 2. In addition, the hole transport region HTR may further include any suitable materials, in addition to the monoamine compound represented in Compound Group 1 and/or Compound Group 2.

The hole transport region HTR of the organic electroluminescence device 10 of an embodiment may include the monoamine compound of an embodiment. If the hole transport region HTR is formed of a plurality of organic layers, the monoamine compound of an embodiment may be included in an organic layer which is adjacent to an emission layer EML.

For example, the monoamine compound of an embodiment may be included in a hole transport layer HTL of the hole transport region HTR. If the hole transport layer HTL includes a plurality of organic layers, the monoamine compound of an embodiment may be included in a layer that is adjacent to the emission layer EML among the plurality of organic layers.

If the hole transport region HTR of the organic electroluminescence device 10 of an embodiment includes a hole injection layer HIL and a hole transport layer HTL, the monoamine compound of an embodiment may be included in the hole transport layer HTL, and if the hole transport region HTR of the organic electroluminescence device of an embodiment includes a hole injection layer HIL, a hole transport layer HTL, and an electron blocking layer EBL, the monoamine compound of an embodiment may be included in the electron blocking layer EBL.

In the organic electroluminescence device 10 of an embodiment, if the hole transport layer HTL includes the monoamine compound of an embodiment, the hole injection layer HIL may include a hole injection material. For example, the hole injection layer HIL may include triphenylamine-containing polyetherketone (TPAPEK), 4-isopropyl-4'-methyldiphenyliodoniumtetrakis(pentafluorophenyl)borate (PPBI), N,N'-diphenyl-N,N'-bis-[4-(phenyl-m-tolyl-amino)-phenyl]-phenyl-4,4'-diamine (DNTPD), a phthalocyanine compound such as copper phthalocyanine, 4,4',4"-tris(3-methyl phenyl phenylamino)triphenylamine (m-MTDATA), N,N'-di(1-naphthyl)-N,N'-diphenylbenzidine (NPB), N,N'-bis(1-naphthyl)-N,N'-diphenyl-4,4'-diamine (a-NPD), 4,4',4"-tris(N,N-diphenylamino)triphenylamine (TDATA), 4,4',4"-tris(N,N-2-naphthyl phenylamino)triphenylamine (2-TNATA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate) (PANI/PSS), or dipyrazino[2,3-f:2',3'-h]quinoxaline-2,3,6,7,10,11-hexacarbonitrile (HAT-CN). However, an embodiment of the inventive concept is not limited thereto.

The hole transport layer HTL of the organic electroluminescence device 10 of an embodiment may further include any suitable hole transport material, in addition to the monoamine compound of an embodiment. For example, the hole transport layer HTL may further include 1,1-bis[(di-4-trileamino)phenyl]cyclohexane (TAPC), carbazole derivatives (such as N-phenyl carbazole and/or polyvinyl carbazole), fluorine derivatives, N,N'-bis(3-methylphenyl)-N,N'-diphenyl-[1,1-biphenyl]-4,4'-diamine (TPD), triphenylamine derivatives (such as 4,4',4"-tris(N-carbazolyl)triphenylamine (TCTA)), N,N'-di(1-naphtalene-1-yl)-N,N'-diphenyl-benzidine (NPB), 4,4'-cyclohexylidene bis[N,N-bis(4-methylphenyl]benzenamine] (TAPC), 4,4'-bis[N,N'-(3-tolyl)amino]-3,3'-dimethylbiphenyl (HMTPD), 1,3-bis(N-carbazolyl)benzene (mCP), and/or the like. However, an embodiment of the inventive concept is not limited thereto.

As described above, in the organic electroluminescence device 10 of an embodiment, the hole transport region HTR may further include at least one of a hole buffer layer or an electron blocking layer EBL, in addition to the hole injection layer HIL and the hole transport layer HTL. The hole buffer layer may compensate an optical resonance distance according to the wavelength of light emitted from an emission layer EML and may increase light emission efficiency. Any of the materials which may be included in a hole transport region HTR may be used as materials which may be included in a hole buffer layer.

When the hole transport region HTR further includes an electron blocking layer EBL disposed (e.g., positioned) between a hole transport layer HTL and an emission layer EML, the electron blocking layer EBL may play the role of preventing (or reducing) electron injection from the electron transport region ETR to the hole transport region HTR.

In the organic electroluminescence device 10 of an embodiment, when the hole transport region HTR includes an electron blocking layer EBL, the electron blocking layer EBL may include the monoamine compound of an embodiment. In some embodiments, the electron blocking layer EBL may include any suitable material in addition to the monoamine compound of an embodiment. The electron blocking layer EBL may include, for example, carbazole derivatives (such as N-phenylcarbazole and/or polyvinyl carbazole), fluorine-based derivatives, N,N'-bis(3-methylphenyl)-N,N'-diphenyl-[1,1-biphenyl]-4,4'-diamine (TPD), triphenylamine-based derivatives (such as 4,4',4"-tris(N-carbazolyl)triphenylamine (TCTA)), N,N'-di(naphthalene-1-yl)-N,N'-diphenyl-benzidine (NPD), 4,4'-cyclohexylidene bis[N,N-bis(4-methylphenyl)benzenamine] (TAPC), 4,4'-bis[N,N'-(3-tolyl)amino]-3,3'-dimethylbiphenyl (HMTPD), mCP, and/or the like.

In the organic electroluminescence device 10 of an embodiment, if the hole transport region HTR is a single layer, the hole transport region HTR may include the monoamine compound of an embodiment. In this case, the hole transport region HTR may further include any suitable hole injection material and/or any suitable hole transport material.

In addition, in the organic electroluminescence device 10 of an embodiment, if the hole transport region HTR includes a plurality of layers, at least one layer among the plurality of layers included in the hole transport region HTR may include the monoamine compound of an embodiment. For example, a layer adjacent to an emission layer EML among the plurality of layers included in the hole transport region HTR may include the monoamine compound of an embodiment. Meanwhile, the layers not including the monoamine compound of an embodiment among the plurality of layers, may include any suitable hole injection material, and/or any suitable hole transport material. In addition, the layer including the monoamine compound of an embodiment may further include any suitable hole injection material, and/or any suitable hole transport material.

The thickness of the hole transport region HTR may be from about 100 Å to about 10,000 Å, for example, from about 100 Å to about 5,000 Å. The thickness of the hole injection layer HIL may be, for example, from about 30 Å to about 1,000 Å, and the thickness of the hole transport layer HTL may be from about 30 Å to about 1,000 Å. For example, the thickness of the electron blocking layer EBL may be from about 10 Å to about 1,000 Å. If the thicknesses of the hole transport region HTR, the hole injection layer HIL, the hole transport layer HTL and the electron blocking layer EBL satisfy the above-described ranges, satisfactory (or suitable) hole transport properties may be achieved without substantial increase of a driving voltage.

The hole transport region HTR may further include a charge generating material, in addition to the above-described materials, to increase conductivity. The charge generating material may be dispersed uniformly or non-uniformly in the hole transport region HTR. The charge generating material may be, for example, a p-dopant. The p-dopant may be selected from quinone derivatives, metal oxides, and cyano group-containing compounds, without limitation. Non-limiting examples of the p-dopant may include quinone derivatives (such as tetracyanoquinodimethane (TCNQ) and/or 2,3,5,6-tetrafluoro-7,7,8,8-tetracyanoquinodimethane (F4-TCNQ)), and metal oxides (such as tungsten oxide and/or molybdenum oxide).

The emission layer EML is provided on the hole transport region HTR. The thickness of the emission layer EML may be, for example, from about 100 Å to about 300 Å. The emission layer EML may have a single layer formed using a single material, a single layer formed using a plurality of different materials, or a multilayer structure having a plurality of layers formed using a plurality of different materials.

The emission layer EML may emit one of red, green, blue, white, yellow or cyan light. The emission layer EML may include a fluorescence-emitting material and/or a phosphorescence-emitting material.

In some embodiments, in the organic electroluminescence device 10 of an embodiment, the emission layer EML may include a host and a dopant.

In the organic electroluminescence device of an embodiment, the emission layer EML may include, as a host, tris(8-hydroxyquinolino)aluminum ($Alq_3$), 3,3'-bis(N-carbazolyl)-1,1'-biphenyl (mCBP), poly(N-vinylcarbazole) (PVK), 9,10-di(naphthalene-2-yl)anthracene (ADN), 3-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), hexaphenyl cyclotriphosphazene (CPI), 1,4-bis(triphenylsilyl)benzene (UGH2), hexaphenylcyclotrisiloxane ($DPSiO_3$), octaphenylcyclotetrasiloxane ($DPSiO_4$), and/or the like, without limitation.

In an embodiment, the emission layer EML may include, as a dopant, styryl derivatives (for example, 1,4-bis[2-(3-N-ethylcarbazoryl)vinyl]benzene (BCzVB), 4-(di-p-tolylamino)-4'-[(di-p-tolylamino)styryl]stilbene (DPAVB) and/or N-(4-((E)-2-(6-((E)-4-(diphenylamino)styryl)naphthalen-2-yl)vinyl)phenyl)-N-phenylbenzenamine (N-BDAVBi)), perylene and the derivatives thereof (for example, 2,5,8,11-tetra-t-butylperylene (TBP)), pyrene and the derivatives thereof (for example, 1,1-dipyrene, 1,4-dipyrenylbenzene, and/or 1,4-bis(N,N-diphenylamino)pyrene), and/or the like, without limitation.

If the emission layer EML emits red light, the emission layer EML may further include a fluorescence material including tris(dibenzoylmethanato)phenanthroline europium (PBD:Eu(DBM)3(Phen)) or perylene. If the emission layer EML emits red color, the dopant included in the emission layer EML may be selected from, for example, a metal complex or an organometallic complex, such as bis (1-phenylisoquinoline)acetylacetonate iridium (PIQIr (acac)), bis(1-phenylquinoline)acetylacetonate iridium (PQIr(acac)), tris(1-phenylquinoline)iridium (PQIr) and octaethylporphyrin platinum (PtOEP), rubrene and the derivatives thereof, and/or 4-dicyanomethylene-2-(p-dimethylaminostyryl)-6-methyl-4H-pyrane (DCM) and the derivatives thereof.

If the emission layer EML emits green light, the emission layer EML may further include a fluorescence material including tris(8-hydroxyquinolino)aluminum (Alq3). If the emission layer EML emits green light, the dopant included in the emission layer EML may be selected from, for example, a metal complex or an organometallic complex, such as fac-tris(2-phenylpyridine)iridium (Ir(ppy)3), and/or coumarin and the derivatives thereof.

If the emission layer EML emits blue light, the emission layer EML may further include a fluorescence material including, for example, any one selected from spiro-DPVBi, spiro-6P, distyryl-benzene (DSB), distyryl-arylene (DSA), a polyfluorene (PFO)-based polymer and a poly(p-phenylene vinylene (PPV)-based polymer. If the emission layer EML emits blue light, the dopant included in the emission layer EML may be selected from, for example, a metal complex or an organometallic complex, such as (4,6-F2ppy)2Irpic, and/or perylene and the derivatives thereof.

In some embodiments, the emission layer EML of the organic electroluminescence device 10 of an embodiment may emit blue light. For example, the emission layer EML may emit light in a wavelength region of about 450 nm to about 490 nm.

In the organic electroluminescence device 10 of an embodiment, the electron transport region ETR is provided on the emission layer EML. The electron transport region ETR may include at least one of a hole blocking layer HBL, an electron transport layer ETL or an electron injection layer EIL. However, an embodiment of the inventive concept is not limited thereto.

The electron transport region ETR may have a single layer formed using a single material, a single layer formed using a plurality of different materials, or a multilayer structure having a plurality of layers formed using a plurality of different materials.

For example, the electron transport region ETR may have a single layer structure of an electron injection layer EIL or an electron transport layer ETL, or a single layer structure formed using an electron injection material and an electron transport material. In some embodiments, the electron transport region ETR may have a single layer structure having a plurality of different materials, or a structure laminated from the emission layer EML of electron transport layer ETL/ electron injection layer EIL, or hole blocking layer HBL/ electron transport layer ETL/electron injection layer EIL, without limitation. The thickness of the electron transport region ETR may be, for example, from about 100 Å to about 1,500 Å.

The electron transport region ETR may be formed using one or more suitable methods, such as a vacuum deposition method, a spin coating method, a cast method, a Langmuir-Blodgett (LB) method, an inkjet printing method, a laser printing method, and/or a laser induced thermal imaging (LITI) method, without limitation.

If the electron transport region ETR includes an electron transport layer ETL, the electron transport region ETR may include, for example, tris(8-hydroxyquinolinato)aluminum (Alq3), 1,3,5-tri[(3-pyridyl)-phen-3-yl]benzene, 2,4,6-tris (3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri(1-phenyl-1H-benzo[d]imidazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)- (1,1'-biphenyl-4-olato)aluminum (BAlq), berylliumbis(benzoquinolin-10-olate (Bebq2), 9,10-di(naphthalene-2-yl) anthracene (ADN), or a mixture thereof, without limitation.

If the electron transport region ETR includes the electron transport layer ETL, the thickness of the electron transport layer ETL may be from about 100 Å to about 1,000 Å and may be, for example, from about 150 Å to about 500 Å. If the thickness of the electron transport layer ETL satisfies the above-described range, satisfactory (or suitable) electron transport properties may be obtained without a substantial increase of a driving voltage.

If the electron transport region ETR includes the electron injection layer EIL, the electron transport region ETR may include, for example, LiF, 8-hydroxyquinolinnolata-lithium (LiQ), $Li_2O$, BaO, NaCl, CsF, a metal in lanthanoides (such as Yb), and/or a metal halide such as RbCl, RbI and/or KI. However, an embodiment of the inventive concept is not limited thereto. The electron injection layer EIL also may be formed using a mixture material of an electron transport material and an insulating organo metal salt. The organo metal salt may be a material having an energy band gap of about 4 eV or more. In some embodiments, the organo metal salt may include, for example, metal acetates, metal benzoates, metal acetoacetates, metal acetylacetonates, and/or metal stearates, without limitation.

If the electron transport region ETR includes the electron injection layer EIL, the thickness of the electron injection layer EIL may be from about 1 Å to about 100 Å, for example, from about 3 Å to about 90 Å. If the thickness of the electron injection layer EIL satisfies the above described range, satisfactory (or suitable) electron injection properties may be obtained without a substantial increase of a driving voltage.

The electron transport region ETR may include a hole blocking layer HBL as described above. The hole blocking layer HBL may include, for example, at least one selected from 2,9-dimethyl-4,7-diphenyl-1,10-phenanthroline (BCP) and 4,7-diphenyl-1,10-phenanthroline (Bphen). However, an embodiment of the inventive concept is not limited thereto.

The second electrode EL2 is provided on the electron transport region ETR. The second electrode EL2 has conductivity. The second electrode EL2 may be formed using a metal alloy or a conductive compound. The second electrode EL2 may be a cathode. The second electrode EL2 may be a transmissive electrode, a transflective electrode or a reflective electrode. If the second electrode EL2 is the transmissive electrode, the second electrode EL2 may include a transparent metal oxide, for example, ITO, IZO, ZnO, ITZO, and/or the like.

If the second electrode EL2 is the transflective electrode or the reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). The second electrode EL2 may have a multilayered structure including a reflective layer or a transflective layer formed using any of the above-described materials and a transparent conductive layer formed using ITO, IZO, ZnO, ITZO, and/or the like.

The second electrode EL2 may be connected (e.g., coupled) with an auxiliary electrode. If the second electrode EL2 is connected with the auxiliary electrode, the resistance of the second electrode EL2 may decrease.

In the organic electroluminescence device 10, according to the application of a voltage to each of the first electrode EL1 and second electrode EL2, holes injected from the first electrode EL1 may move via the hole transport region HTR to the emission layer EML, and electrons injected from the second electrode EL2 may move via the electron transport region ETR to the emission layer EML. The electrons and the holes are recombined in the emission layer EML to produce excitons, and the excitons may emit light via transition from an excited state to a ground state.

If the organic electroluminescence device 10 is a top emission device, the first electrode EL1 may be a reflective electrode and the second electrode EL2 may be a transmissive electrode or a transflective electrode. If the organic electroluminescence device 10 is a bottom emission device, the first electrode EL1 may be a transmissive electrode or a transflective electrode and the second electrode EL2 may be a reflective electrode.

The monoamine compound of an embodiment may be included as a material for an organic electroluminescence device 10 of an embodiment. The organic electroluminescence device 10 according to an embodiment of the inventive concept may include the monoamine compound in at least one organic layer selected from the organic layers disposed between the first electrode EL1 and the second electrode EL2, and a capping layer disposed on the second electrode EL2.

When the monoamine compound is included in at least one organic layer disposed between the first electrode EL1 and the second electrode EL2 in the organic electroluminescence device 10 according to an embodiment of the inventive concept, excellent (or suitable) light emission efficiency and high reliability may be achieved. For example, by including the monoamine compound in a hole transport region HTR in the organic electroluminescence device 10 according to an embodiment of the inventive concept, excellent (or suitable) light emission efficiency and improved life characteristics may be achieved.

When the organic electroluminescence device of an embodiment includes the monoamine compound of an embodiment in an organic layer which is adjacent to an emission layer among the plurality of organic layers in a hole transport region, the hole transport region can maintain relatively high hole transport capacity and may restrain (or reduce) the movement of electrons, thereby showing improved light emission efficiency.

The monoamine compound of an embodiment, in which an adamantyl group is substituted so as to be bonded at ortho or meta position with respect to the nitrogen atom of an arylamine moiety, may have high heat resistance, and thus, an organic electroluminescence device including the monoamine compound in, for example, a hole transport region may show excellent (e.g., improved) life characteristics. In addition, when the monoamine compound of an embodiment, in which an adamantyl group is substituted so as to be bonded at ortho or meta position with respect to the nitrogen atom of an arylamine moiety, is included in a layer of the hole transport region that is adjacent to an emission layer, the loss of excitation energy generated in the emission layer may be restrained (or reduced) and the charge balance of a light-emitting device may be maintained, and thus, the organic electroluminescence device may achieve relatively high light emission efficiency.

Hereinafter, the monoamine compound according to an embodiment of the inventive concept and an organic electroluminescence device including the monoamine compound of an embodiment will be explained in more detail with reference to examples and comparative examples. However, the following embodiments are only illustrations to assist the understanding of the inventive concept, and the scope of the inventive concept is not limited thereto.

EXAMPLES

1. Synthesis of Monoamine Compound

First, the synthetic method (the method of synthesizing) of the monoamine compound according to an embodiment of the inventive concept will be explained by referring to the synthetic methods of Compound 1, Compound 4, Compound 13 and Compound 19 in Compound Group 1, and Compound 34, Compound 39, Compound 42, Compound 53, and Compound 77 in Compound Group 2. It should be understood, however, that the synthetic methods of the monoamine compounds explained below are only example embodiments, and the synthetic method of the monoamine compound according to an embodiment of the inventive concept is not limited thereto.

Synthesis of Compound 1

A monoamine compound according to an embodiment, Compound 1, may be synthesized, for example, by the following Reaction 1:

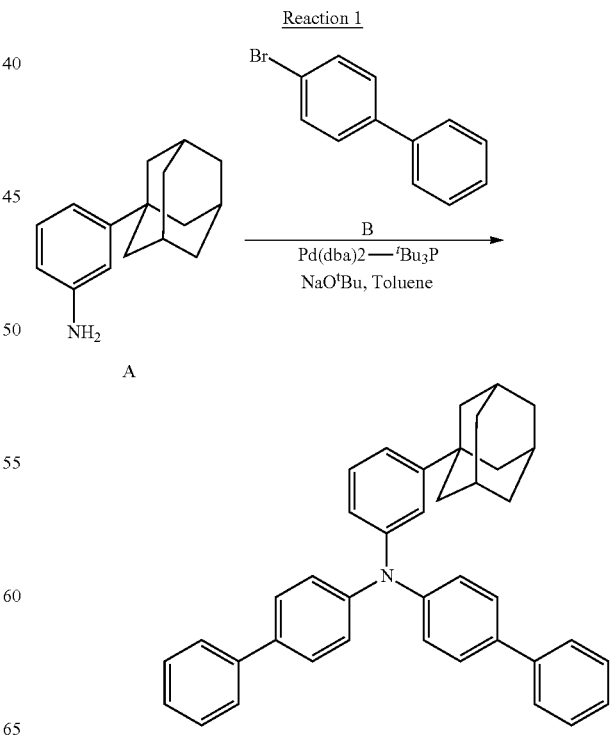

According to the process of Reaction 1, Compound 1 was synthesized. Referring to Reaction 1, under an argon (Ar) atmosphere, 4.51 g (19.8 mmol) of Compound A, 9.24 g (39.7 mmol) of Compound B, 0.57 g (0.991 mmol) of Pd(dba)$_2$, 1.24 ml (1.6 M solution, 1.98 mmol) of tri(tert-butylphosphine), and 5.72 g (59.5 mmol) of NaOt-Bu were added, and the mixture was heated and refluxed in 150 ml of a toluene solvent at about 110° C. for about 5 hours. After cooling in the air, the crude product thus obtained was separated by silica gel chromatography and recrystallized to obtain 8.75 g (16.5 mmol, yield 83%) of a target material, Compound 1. A molecular ion peak of m/z=541 was verified by measuring Fast Atom Bombardment-Mass Spectroscopy (FAB-MS), and from the result, the product was identified as the target material, Compound 1.

Synthesis of Compound 4

A monoamine compound according to an embodiment, Compound 4, may be synthesized, for example, by the following Reaction 2:

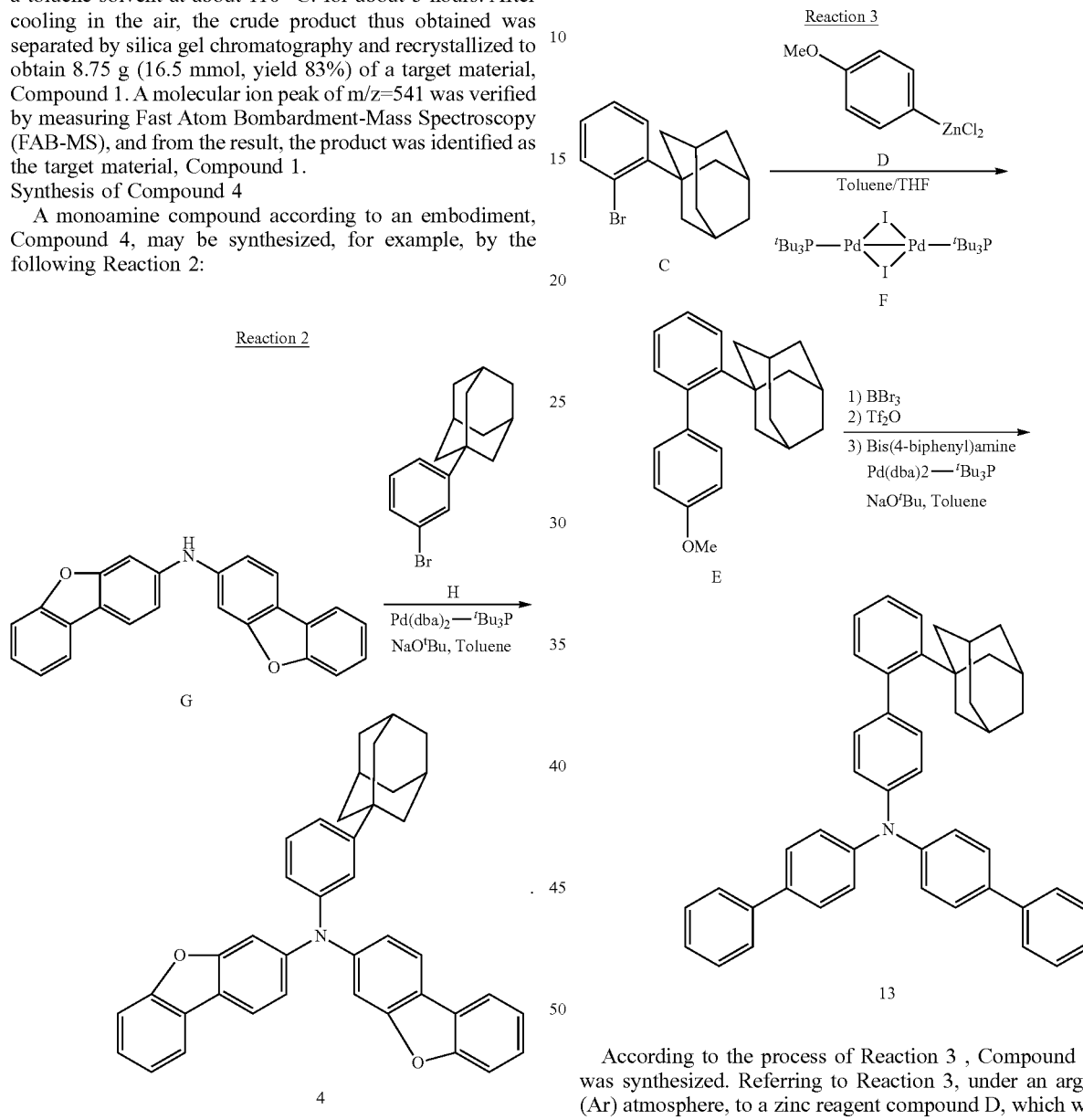

According to the process of Reaction 2, Compound 4 was synthesized. Referring to Reaction 2, under an argon (Ar) atmosphere, a toluene suspension (200 ml) of Compound G (5.56 g, 15.9 mmol), Compound H (4.63 g, 15.9 mmol), bis(dibenzilideneacetone)palladium (457 mg, 0.795 mmol), tri(tert-butylphosphine (1.6 M solution, 0.994 ml, 1.59 mmol), and sodium t-butoxide (4.59 g, 47.7 mmol) was deaerated, and heated at about 110° C. for about 6 hours. After cooling in the air, the reaction product was filtered and concentrated, and the residue thus obtained was separated by column chromatography to obtain Compound 4 (6.94 g, 12.4 mmol, yield 78%). A molecular ion peak of m/z=559 was verified by measuring FAB-MS, and from the result, the product was identified as the target material.

Synthesis of Compound 13

A monoamine compound according to an embodiment, Compound 13, may be synthesized, for example, by the following Reaction 3:

According to the process of Reaction 3, Compound 13 was synthesized. Referring to Reaction 3, under an argon (Ar) atmosphere, to a zinc reagent compound D, which was separately adjusted, in a Grignard reagent which was prepared using 3.54 g (24.8 mmol) of 4-chloroanisole, 100 ml of a toluene solution including 4.82 g (16.6 mmol) of a THF solution of compound C, which was obtained via treatment with zinc chloride according to the method of P. Knochel, and 0.433 g (0.497 mmol) of a Pd catalyst of Compound F were added, followed by stirring at room temperature for about 3 hours. To the stirred reaction solution, acetonitrile was added, and precipitates obtained therefrom were removed. A filtrate was concentrated and separated by silica gel chromatography to obtain 4.80 g (15.1 mmol, yield 61%) of Compound E. The intermediate thus obtained, Compound E, was dissolved in 100 mw of dichloromethane and was treated with borontrifuloride dissolved in 30 ml of dichloromethane (1 M) at ROC. Then, water was added to the reaction mixture and an organic layer was concentrated.

The residue thus concentrated was dissolved in 50 ml of pyridine, and 6.38 g (22.6 mmol) of trifluoromethanesulfonic anhydride was added thereto dropwisely at about 0° C., and stirred at about 0° C. for about 3 hours. The reaction product was concentrated, dissolved in 100 ml of dichloromethane, washed with water and concentrated.

Then, to the residue thus concentrated, 4.84 g (15.1 mmol) of bis(4-biphenylyl)amine, 0.433 g (0.753 mmol) of bis(dibenzylideneacetone)palladium(0), 4.34 g (45.2 mmol) of sodium t-butoxide, and 200 mol of toluene were added and stirred under an argon atmosphere for about 8 hours.

The reaction product was filtered, and the residue thus obtained was separated by column chromatography to obtain 7.14 g (11.8 mmol, yield 78%) of Compound 13. A molecular ion peak of m/z=607 was verified by measuring FAB-MS, and from the result, the product was identified as the target material.

Synthesis of Compound 19

A monoamine compound according to an embodiment, Compound 19, may be synthesized, for example, by the following Reaction 4:

mmol), bis(dibenzilideneacetone)palladium (440 mg, 0.765 mmol), tri(tert-butylphosphine (1.6 M solution, 0.956 ml, 1.53 mmol), and sodium-t-butoxide (7.53 g, 76.5 mmol) was deaerated, and heated at about 110° C. for about 7 hours. After cooling in the air, the reaction product was filtered and concentrated, and the residue thus obtained was separated by column chromatography to obtain Compound 19 (6.25 g, 11.2 mmol, yield 73%). A molecular ion peak of m/z=665 was secured by measuring FAB-MS, and from the result, the product was identified as the target material.

Synthesis of Compound 34

A monoamine compound according to an embodiment, Compound 34, may be synthesized, for example, by the following Reaction 5:

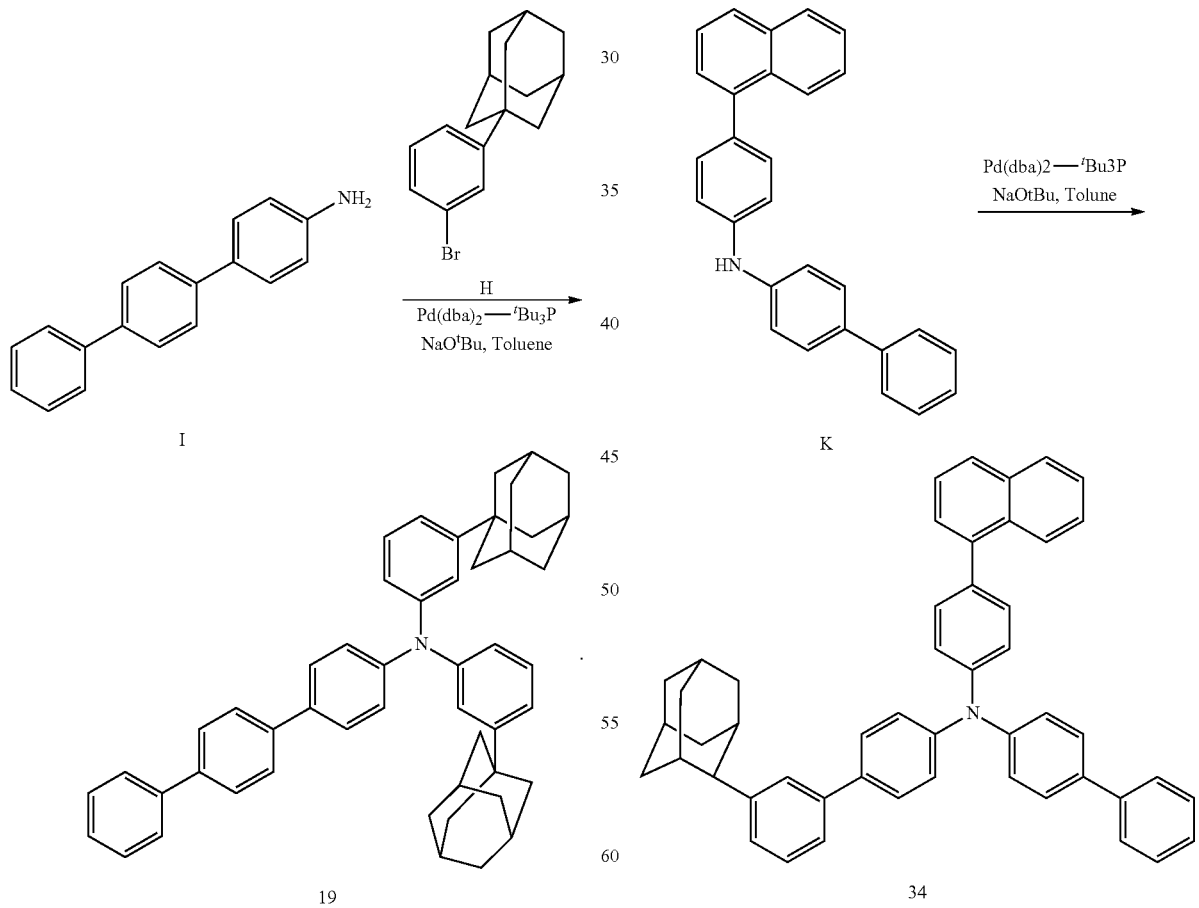

According to the process of Reaction 4, Compound 19 was synthesized. Referring to Reaction 4, under an argon (Ar) atmosphere, a toluene suspension (200 ml) of Compound I (4.00 g, 15.3 mmol), Compound H (8.91 g, 30.6

According to the process of Reaction 5, Compound 34 was synthesized. Referring to Reaction 5, under an argon (Ar) atmosphere, 3.00 g (8.17 mmol) of Compound J, 3.34 g (8.98 mmol) of Compound K, 0.23 g (0.408 mmol) of Pd(dba)$_2$, 1.30 ml (1.6 M solution, 0.82 mmol) of tri(tert-butylphosphine), and 2.35 g (24.5 mmol) of NaOt-Bu were added, and heated and refluxed in 100 ml of a toluene solvent at about 110° C. for about 5 hours. After cooling in the air, the crude product thus obtained was separated by silica gel chromatography and recrystallized to obtain 3.72 g (6.13 mmol, yield 75%) of a target material, Compound 34. A molecular ion peak of m/z=657.4 was verified by measuring FAB-MS, and from the result, the product was identified as the target material, Compound 34.

Synthesis of Compound 39

A monoamine compound according to an embodiment, Compound 39, may be synthesized, for example, by the following Reaction 6:

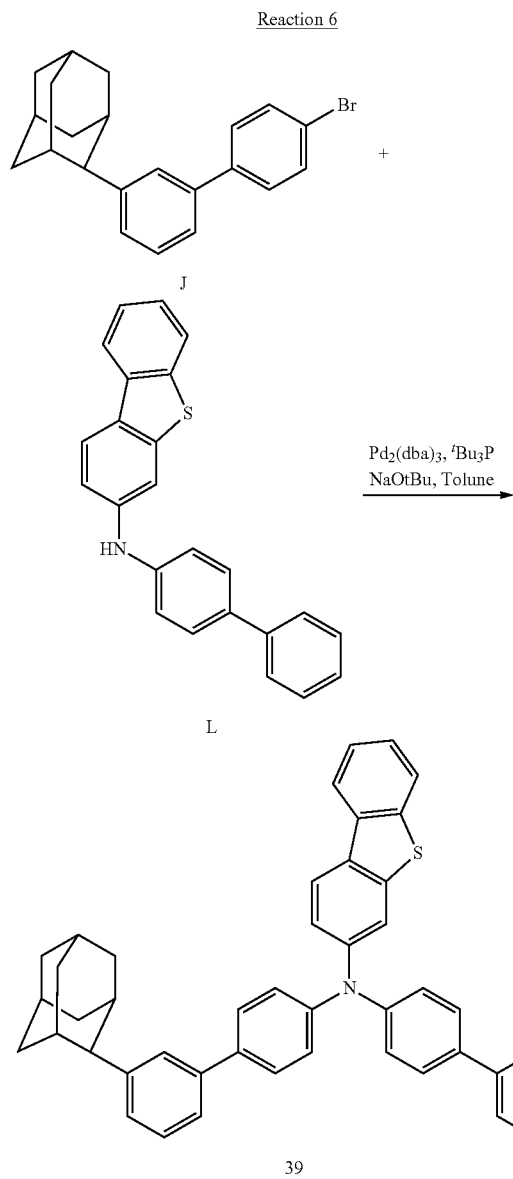

According to the process of Reaction 6, Compound 39 was synthesized. Referring to Reaction 6, Compound 39 was synthesized by performing the same (or substantially the same) method as the synthetic method of Compound 34 (Reaction 5), except for using Compound L instead of Compound K. By using Reaction 6, Compound 39 was obtained in a yield of 69% as a target material. A molecular ion peak of m/z=637.2 was verified by measuring FAB-MS, and from the result, the product was identified as the target material, Compound 39.

Synthesis of Compound 42

A monoamine compound according to an embodiment, Compound 42, may be synthesized, for example, by the following Reaction 7:

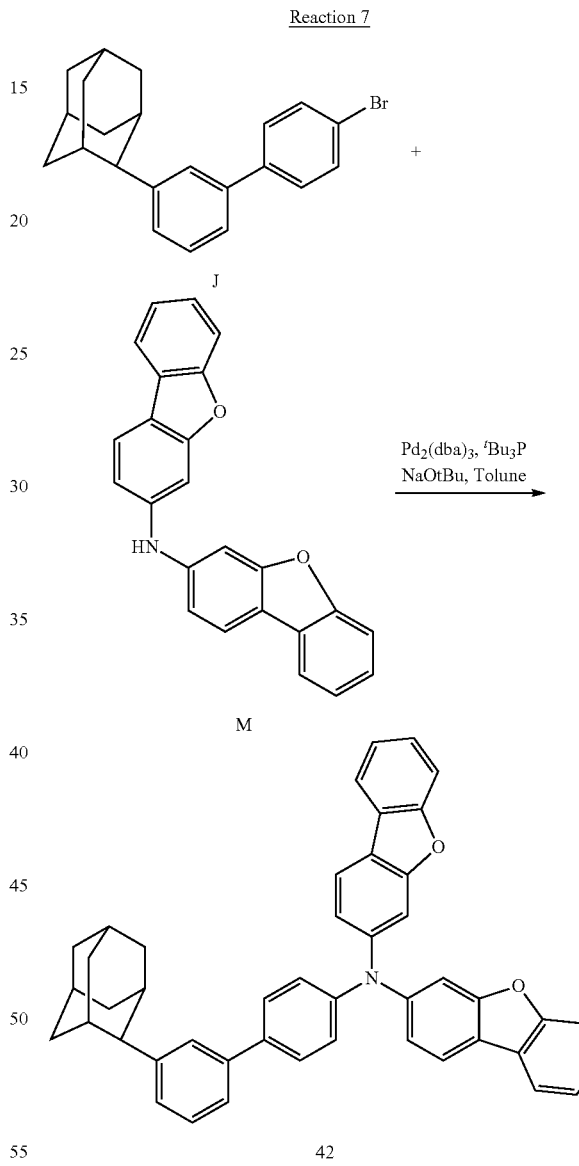

According to the process of Reaction 7, Compound 42 was synthesized. Referring to Reaction 7, Compound 42 was synthesized by performing the same (or substantially the same) method as the synthetic method of Compound 34 (Reaction 5), except for using Compound M instead of Compound K. By using Reaction 7, Compound 42 was obtained in a yield of 72% as a target material. A molecular ion peak of m/z=635.2 was verified by measuring FAB-MS, and from the result, the product was identified as the target material, Compound 42.

Synthesis of Compound 53

A monoamine compound according to an embodiment, Compound 53, may be synthesized, for example, by the following Reaction 8:

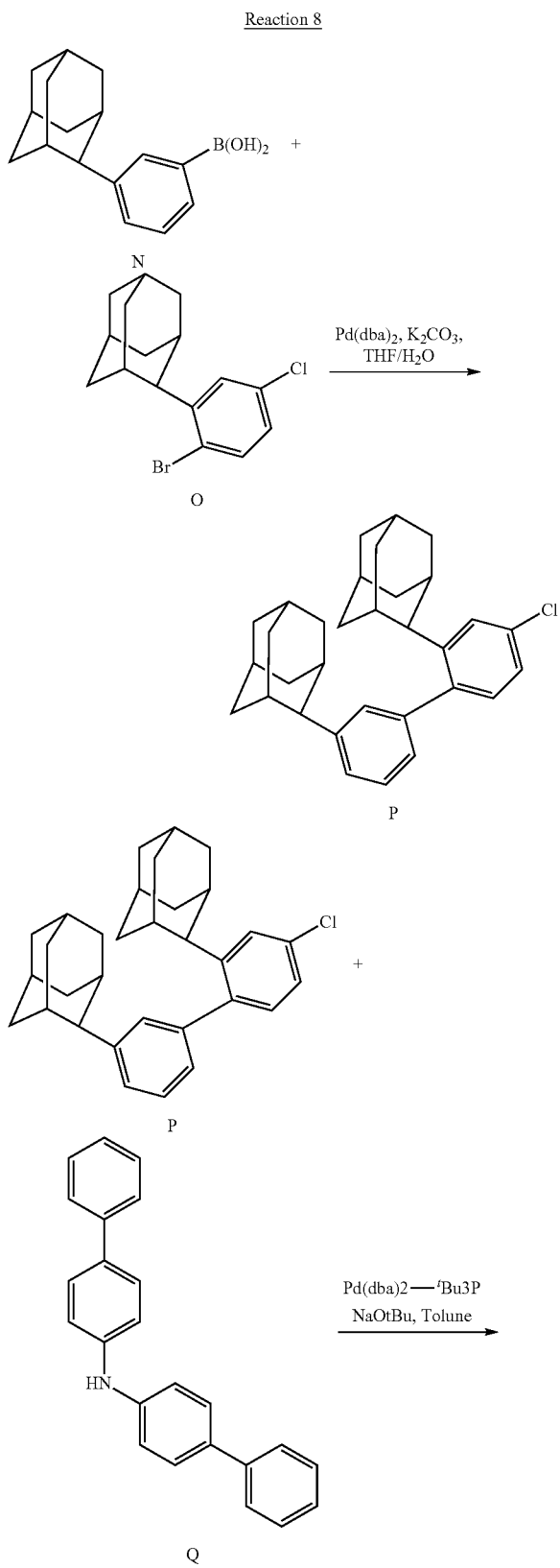

According to the process of Reaction 8, Compound 53 was synthesized. Referring to Reaction 8, under an argon (Ar) atmosphere, a mixed solution of THF/water (THF: water was in a ratio of 8:2) in which 5.00 g (19.52 mmol) of Compound N, 6.99 g (21.47 mmol) of Compound O, 0.56 g (0.98 mmol) of Pd(dba)$_2$, and 8.09 g of K$_2$CO$_3$ were dissolved, was heated and refluxed for about 5 hours. After cooling in the air, dichloromethane was added, an organic layer was separately taken, and solvents were removed. The crude product thus obtained was separated by silica gel chromatography to obtain 3.66 g (8.01 mmol, yield 41%) of Intermediate Compound P. A molecular ion peak of m/z=456.3 was verified by measuring FAB-MS, and from the result, the product was identified as the target material, Intermediate Compound P.

Referring to Reaction 5, Compound 53 was synthesized by performing the same (or substantially the same) method as the synthetic method of Compound 34, except for using Intermediate Compound P instead of Compound J and using Compound Q instead of Compound K. By using Reaction 8, Compound 53 was obtained in a yield of 52% as a target material. A molecular ion peak of m/z=741.3 was verified by measuring FAB-MS, and from the result, the product was identified as the target material, Compound 53.

Synthesis of Compound 77

A monoamine compound according to an embodiment, Compound 77, may be synthesized, for example, by the following Reaction 9:

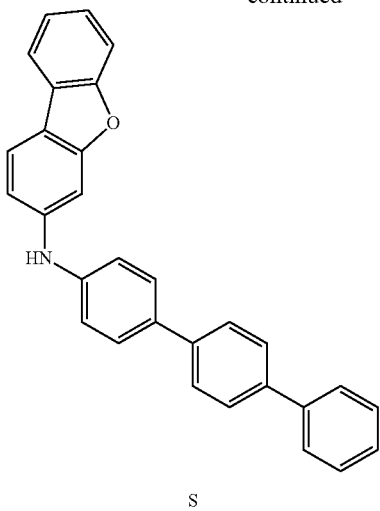

According to the process of Reaction 9, Compound 77 was synthesized. Referring to Reaction 9, Compound 77 was synthesized by performing the same (or substantially the same) method as the synthetic method of Compound 34 (Reaction 5), except for using Compound R instead of Compound J and using Compound S instead of Compound K. By using Reaction 9, Compound 77 was obtained in a yield of 72% as a target material. A molecular ion peak of m/z=621.3 was verified by measuring FAB-MS, and from the result, the product was identified as the target material, Compound 77.

2. Manufacture and Evaluation of Organic Electroluminescence Device Including the Monoamine Compound Manufacture of Organic Electroluminescence Device Organic electroluminescence devices of example embodiments including the monoamine compounds of example embodiments in a hole transport layer were manufactured by the method below. Organic electroluminescence devices of Examples 1-1 to 1-4 were manufactured using the monoamine compounds of Compound 1, Compound 4, Compound 13, and Compound 19 in Compound Group 1 as materials for the hole transport layer. Organic electroluminescence devices of Comparative Examples 1-1 to 1-3 were manufactured using Comparative Compounds C1-1 to C1-3 as materials for a hole transport layer.

In addition, organic electroluminescence devices of Examples 2-1 to 2-5 were manufactured using the monoamine compounds of Compound 34, Compound 39, Compound 42, Compound 53 and Compound 77 in Compound Group 2 as materials for the hole transport layer. Organic electroluminescence devices of Comparative Examples 2-1 to 2-4 were manufactured using Comparative Compounds C2-1 to C2-4 as materials for a hole transport layer.

The compounds used for forming hole transport layers in Examples 1-1 to 1-4 and Comparative Examples 1-1 to 1-3, and the compounds used for forming hole transport layers in Examples 2-1 to 2-5 and Comparative Examples 2-1 to 2-4, are listed in Table 1.

TABLE 1

Compound 1

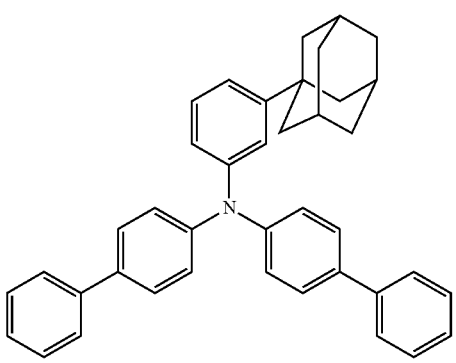

TABLE 1-continued
Compound 4
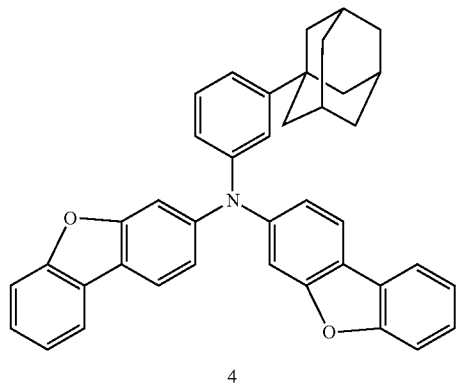 [SMILES: c1cc(N(c2ccc3c(c2)oc2ccccc23)c2ccc3c(c2)oc2ccccc23)cc(C23CC4CC(CC(C4)C2)C3)c1]
4
Compound 13
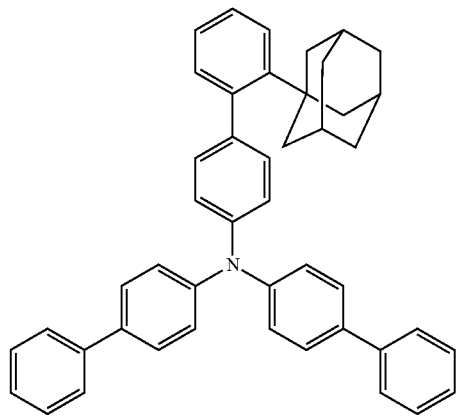
13
Compound 19
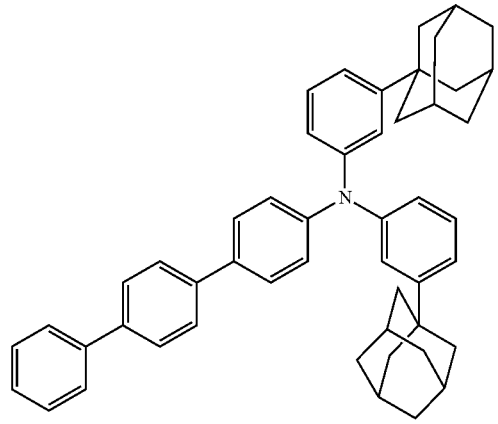
19

TABLE 1-continued
Compound 34
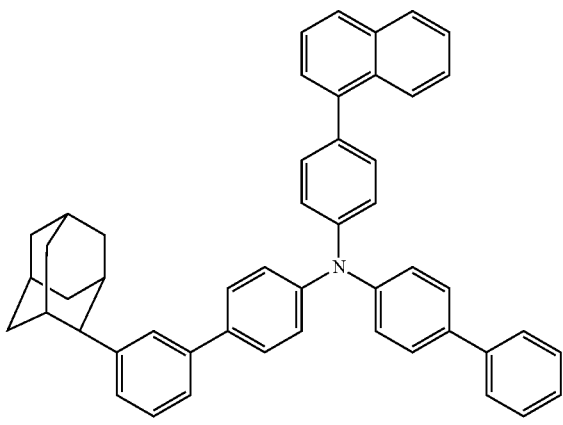
34
Compound 39
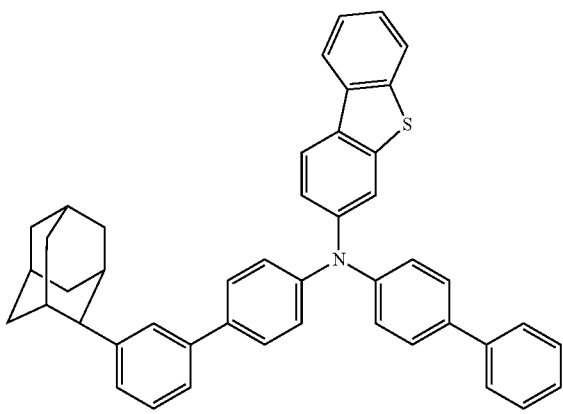
39
Compound 42
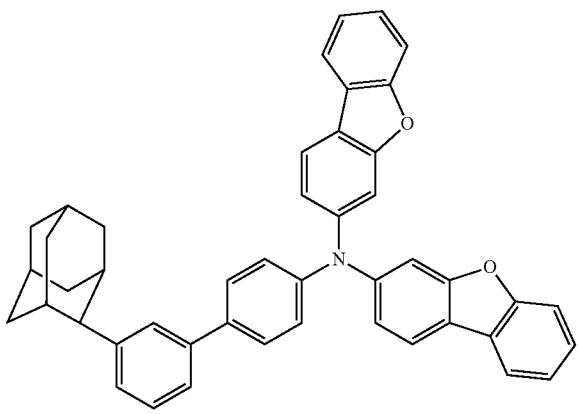
42

TABLE 1-continued
Compound 53
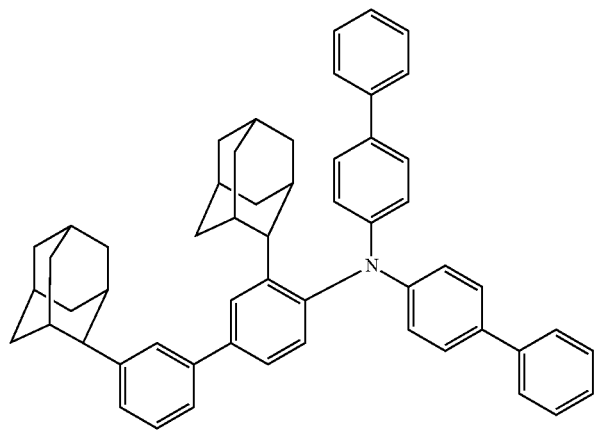
53
Compound 77
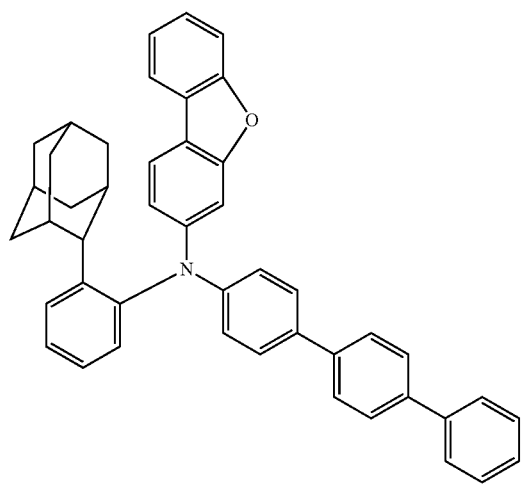
77
Comparative Compound C1-1
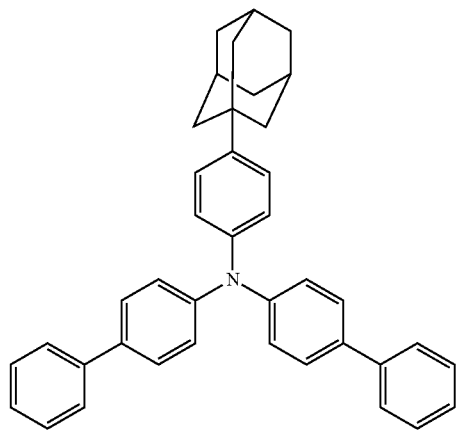
C1-1

TABLE 1-continued
| Comparative Compound C1-2 | 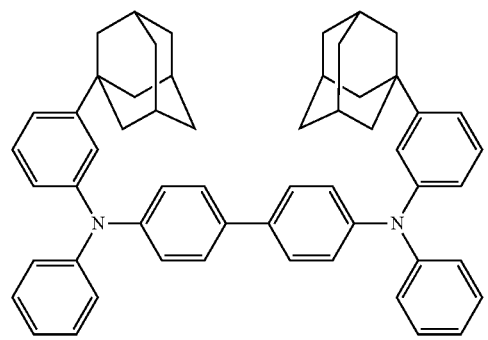 |
| --- | --- |
| | C1-2 |
| Comparative Compound C1-3 | 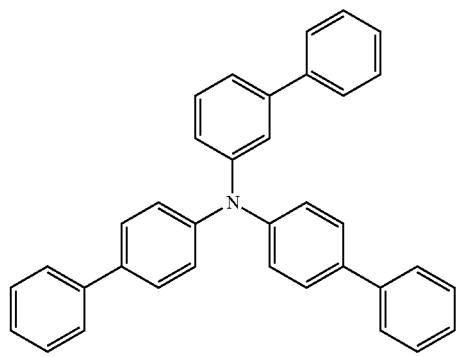 |
| | C1-3 |
| Comparative Compound C2-1 | 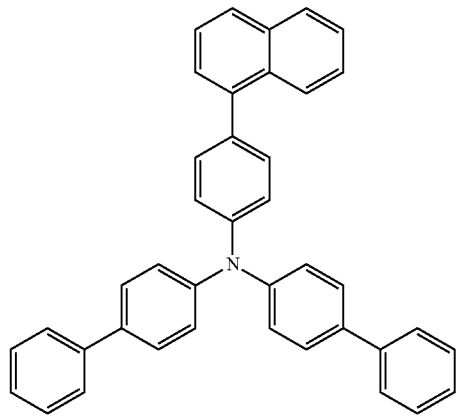 |
| | C2-1 |
| Comparative Compound C2-2 | 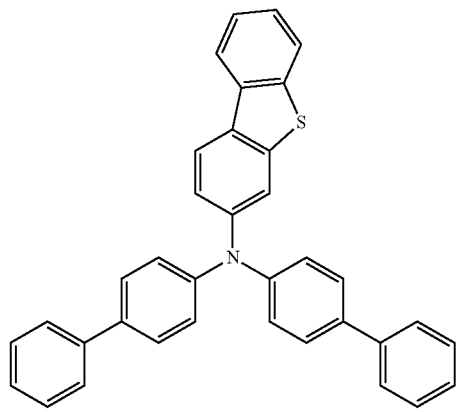 |
| | C2-2 |

TABLE 1-continued

Comparative Compound C2-3

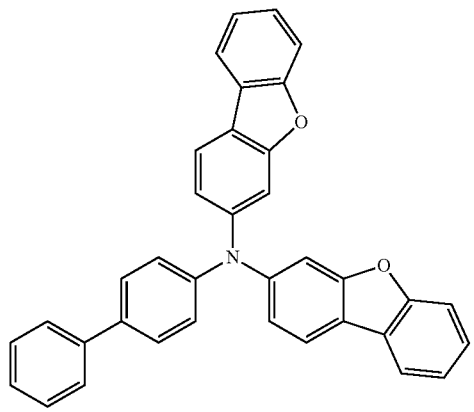

C2-3

Comparative Compound C2-4

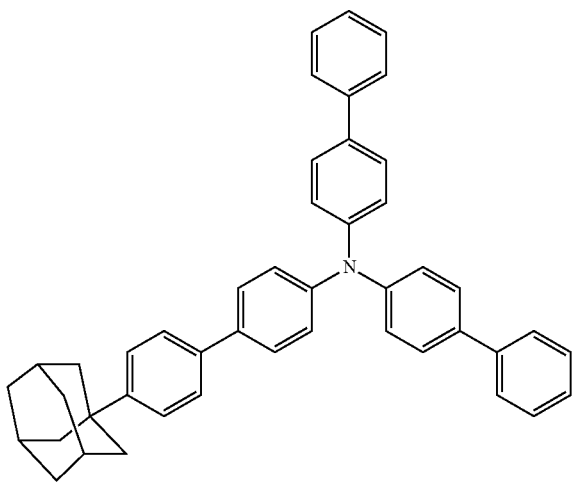

C2-4

On a glass substrate, ITO was patterned to a thickness of about 1,500 Å and washed with ultra-pure water, and a UV ozone treatment was conducted for about 10 minutes. Then, a hole injection layer was formed using 2-TNANA to a thickness of about 600 Å. A hole transport layer was formed using the corresponding example compound or the comparative compound to a thickness of about 300 Å.

Then, an emission layer was formed using ADN doped with 3% TBP to a thickness of about 250 Å. Then, an electron transport layer was formed using $Alq_3$ to a thickness of about 250 Å and an electron injection layer was formed using LiF to a thickness of about 10 Å.

Then, a second electrode was formed using Al to a thickness of about 1,000 Å.

In an embodiment, the hole injection layer, the hole transport layer, the emission layer, the electron transport layer, the electron injection layer and the second electrode were formed by using a vacuum deposition apparatus.

Evaluation of Properties of Organic Electroluminescence Device

The evaluation results of the organic electroluminescence devices according to Example 1-1 to Example 1-4, and Comparative Example 1-1 to Comparative Example 1-3 are shown in Table 2. In Table 2, the device efficiency and the device life of the organic electroluminescence devices thus manufactured are compared and shown. The evaluation results of the properties of the devices in examples and comparative examples in Table 2 are relative ratios with respect to 100% of the light emission efficiency and the life of the device of Comparative Example 1-1, in which Comparative Compound C1-1 was used in the hole transport layer.

In addition, Table 3 shows the evaluation results of the organic electroluminescence devices of Example 2-1 to Example 2-5, and Comparative Example 2-1 to Comparative Example 2-4. Table 3 shows the device efficiency of the organic electroluminescence devices thus manufactured. The evaluation results of the properties for the devices in examples and comparative examples in Table 3 are relative ratios with respect to 100% of the light emission efficiency of the device of Comparative Example 2-1, in which Comparative Compound C2-1 was used in the hole transport layer.

The light emission efficiencies of the organic electroluminescence devices of the examples and comparative examples were measured using a luminous brightness measurement apparatus, C9920-12 of HAMAMATSU Photonics Co., Ltd.

TABLE 2

| Device manufacturing example | Hole transport layer material | Light emission efficiency (%) | Life (%) |
|---|---|---|---|
| Example 1-1 | Compound 1 | 112 | 100 |
| Example 1-2 | Compound 4 | 108 | 105 |
| Example 1-3 | Compound 13 | 110 | 103 |
| Example 1-4 | Compound 19 | 108 | 112 |
| Comparative Example 1-1 | Comparative Compound C1-1 | 100 | 100 |
| Comparative Example 1-2 | Comparative Compound C1-2 | 95 | 70 |
| Comparative Example 1-3 | Comparative Compound C1-3 | 88 | 95 |

Referring to the results of Table 2, it may be found that the organic electroluminescence devices using the monoamine compounds of example embodiments of the inventive concept as hole transport materials showed excellent device life characteristics and excellent light emission efficiency as compared with the organic electroluminescence devices using comparative compounds as hole transport materials.

It may be found that Example 1-1 to Example 1-4 showed higher light emission efficiency when compared with Comparative Example 1-1. The monoamine compounds used in Example 1-1 to Example 1-4 have different substitution position of an adamantyl group when compared with the monoamine compound used in Comparative Example 1-1. That is, in the monoamine compounds used in Example 1-1 to Example 1-4, an adamantyl group was substituted so as to be ortho or meta position with respect to the nitrogen atom of the arylamine moiety, and the organic electroluminescence devices using the monoamine compound showed improved characteristics as compared with the device using Comparative Compound C1-1 in which an adamantyl group was substituted so as to be para position with respect to a nitrogen atom. For example, in the organic electroluminescence devices according to the present embodiments, electron blocking effect was high (e.g., improved), while maintaining hole transport capacity, and thus improved light emission efficiency was achieved.

In addition, Example 1-1 to Example 1-4 were found to show high light emission efficiency and improved emission life when compared with Comparative Example 1-2, in which a diamine compound was used in a hole transport layer, or with Comparative Example 1-3, in which an amine compound not including an adamantyl group as a substituent was used.

TABLE 3

| Device manufacturing example | Hole transport layer material | Light emission efficiency (%) |
|---|---|---|
| Example 2-1 | Compound 34 | 119 |
| Example 2-2 | Compound 39 | 116 |
| Example 2-3 | Compound 42 | 110 |
| Example 2-4 | Compound 53 | 122 |
| Example 2-5 | Compound 77 | 112 |
| Comparative Example 2-1 | Comparative Compound C2-1 | 100 |
| Comparative Example 2-2 | Comparative Compound C2-2 | 91 |
| Comparative Example 2-3 | Comparative Compound C2-3 | 98 |
| Comparative Example 2-4 | Comparative Compound C2-4 | 89 |

Referring to the results of Table 3, it may be found that the organic electroluminescence devices using the monoamine compounds of example embodiments of the inventive concept as hole transport materials showed higher light emission efficiency when compared with the organic electroluminescence devices of the comparative examples.

It may be found that Example 2-1 to Example 2-5 showed higher light emission efficiency when compared with Comparative Example 2-1 to Comparative Example 2-3. The monoamine compounds used in Example 2-1 to Example 2-5 were different from those used in Comparative Example 2-1 to Comparative Example 2-3 in including an adamantyl group as a substituent. That is, in the monoamine compounds of the examples, the adamantyl group having high steric hindrance as a substituent without $\pi$ electrons, surrounded the nitrogen atom of an arylamine moiety, and due to such conformation, the efficiency of the organic electroluminescence devices may be increased. In Example 2-1 to Example 2-5, monoamine compounds including an adamantyl group having such conformation were mainly distributed at the interface of an emission layer so that electrons which were not used for excitation stayed in the emission layer, and the degradation of a hole transport material, which had weak tolerance to electrons, might thus be restrained (or reduced), thereby improving the efficiency of the organic electroluminescence devices.

Comparative Example 2-4 included a monoamine compound having an adamantyl group at a different position from the examples. That is, in the monoamine compounds used in Example 2-1 to Example 2-5, an adamantyl group was substituted so as to be at ortho or meta position with respect to the nitrogen atom of an arylamine part, and the organic electroluminescence devices using the monoamine compound showed improved characteristics as compared with a device using Comparative Compound C2-4 in which an adamantyl group was substituted so as to be at para position with respect to a nitrogen atom. For example, in the organic electroluminescence devices according to the present embodiments, electron blocking effect was high (e.g., improved), while maintaining hole transport capacity, and thus improved light emission efficiency was achieved.

That is, the monoamine compound of an embodiment is used in a hole transport region to improve the light emission efficiency of an organic electroluminescence device.

The monoamine compound of an embodiment includes an adamantyl group as a substituent and has excellent (or suitable) heat resistance. When the substitution position of the adamantyl group is ortho or meta position with respect to the nitrogen atom of an arylamine group, charge balance may be increased, hole transport capacity may be maintained, and electron blocking effect may be achieved. That is, if the monoamine compound of an embodiment is used in the hole transport region of the organic electroluminescence device of an embodiment, the movement of excited excitons generated in an adjacent emission layer may be blocked (or reduced), and the light emission efficiency of the organic electroluminescence device may be improved.

The monoamine compound of an embodiment may improve the light emission efficiency of an organic electroluminescence device.

The organic electroluminescence device of an embodiment includes the monoamine compound of an embodiment in a hole transport region and may achieve high efficiency.

As used herein, the terms "use," "using," and "used" may be considered synonymous with the terms "utilize," "utilizing," and "utilized," respectively.

In addition, the terms "substantially," "about," and similar terms are used as terms of approximation and not as terms of degree, and are intended to account for the inherent deviations in measured or calculated values that would be recognized by those of ordinary skill in the art.

Also, any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

Although the example embodiments of the present invention have been described herein, it is understood that the present invention should not be limited to these example embodiments but various changes and modifications can be made by one ordinary skilled in the art within the spirit and scope of the present invention as defined by the following claims and equivalents thereof.

What is claimed is:

1. An organic electroluminescence device, comprising:
a first electrode;
a second electrode on the first electrode; and
a plurality of organic layers between the first electrode and the second electrode,
wherein at least one organic layer among the plurality of organic layers comprises a monoamine compound represented by the following Formula 1:

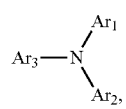

Formula 1 wherein, in Formula 1,
at least one selected from $Ar_1$, $Ar_2$ and $Ar_3$ is represented by the following Formula 2, and the remaining ones of $Ar_1$, $Ar_2$ and $Ar_3$ are each independently a substituted or unsubstituted aryl group having 6 to 30 carbon atoms for forming a ring, or a substituted or unsubstituted heteroaryl group having 2 to 30 carbon atoms for forming a ring:

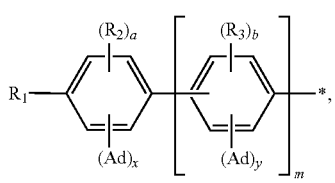

Formula 2 in Formula 2,
$R_1$ to $R_3$ are each independently a hydrogen atom, a deuterium atom, a halogen atom, a cyano group, a substituted or unsubstituted silyl group, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, "m" is 0 or 1, "a", "b", "x" and "y" are each independently an integer of 0 to 4, wherein if "m" is 0, "x" is an integer of 1 or more, and if "m" is 1, "x+y" is an integer of 1 or more, and Ad is represented by the following Formula 3:

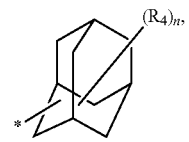

Formula 3 in Formula 3,
$R_4$ is a hydrogen atom, a deuterium atom, a halogen atom, a cyano group, a substituted or unsubstituted silyl group, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, and "n" is an integer of 0 to 15.

2. The organic electroluminescence device of claim 1, wherein the plurality of organic layers comprise:
an emission layer; and
a hole transport region between the first electrode and the emission layer,
wherein the hole transport region comprises the monoamine compound represented by Formula 1.

3. The organic electroluminescence device of claim 1, wherein the plurality of organic layers comprise:
an emission layer;
a hole injection layer between the first electrode and the emission layer; and
a hole transport layer between the hole injection layer and the emission layer,
wherein the hole transport layer comprises the monoamine compound represented by Formula 1.

4. The organic electroluminescence device of claim 1, wherein Formula 3 is represented by the following Formula 3-1 or Formula 3-2:

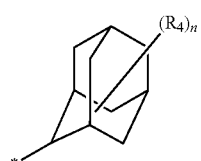

Formula 3-1

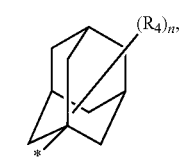

Formula 3-2 wherein, in Formula 3-1 and Formula 3-2, R₄ and "n" are the same as defined in Formula 3.

5. The organic electroluminescence device of claim 1, wherein Formula 1 is represented by the following Formula 1-A or Formula 1-B:

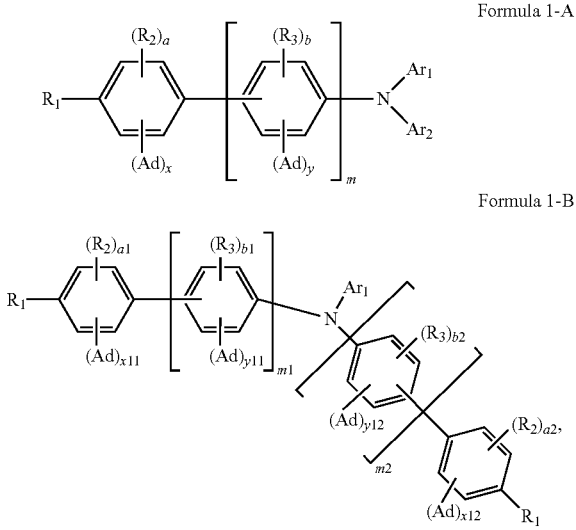

Formula 1-A

Formula 1-B wherein, in Formula 1-B,
"m1" and "m2" are each independently 0 or 1, and
"a1", "a2", "b1", "b2", "x11", "x12", "y11", and "y12" are each independently an integer of 0 to 4,
where if "m1" is 0, "x11" is an integer of 1 or more, if "m1" is 1, "x11+y11" is an integer of 1 or more,
if "m2" is 0, "x12" is an integer of 1 or more, and if "m2" is 1, "x12+y12" is an integer of 1 or more, and
in Formula 1-A and Formula 1-B, Ar₁ and Ar₂ are the same as defined in Formula 1, and R₁ to R₃, "a", "b", "x", "y", and Ad are the same as defined in Formula 2.

6. The organic electroluminescence device of claim 5, wherein Formula 1-A is represented by any one selected from the following Formula 1-1 to Formula 1-3:

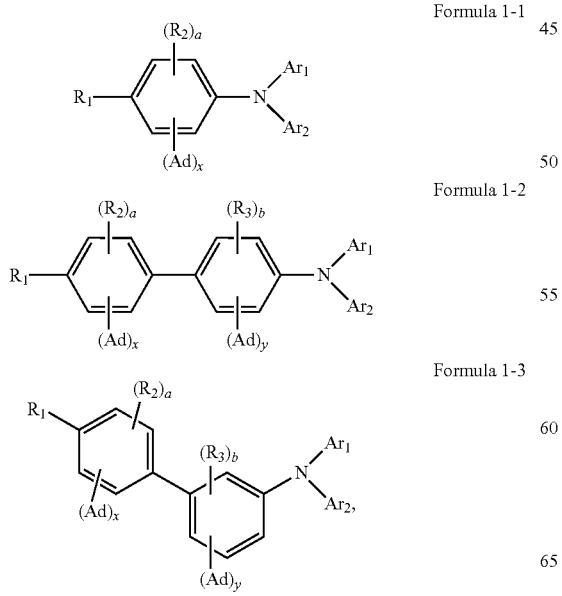

Formula 1-1

Formula 1-2

Formula 1-3 wherein, in Formula 1-1 to Formula 1-3, Ar₁ and Ar₂ are the same as defined in Formula 1, and R₁ to R₃, "a", "b", "b", "x", "y", and Ad are the same as defined in Formula 2.

7. The organic electroluminescence device of claim 5, wherein Ar₁ and Ar₂ are each independently a substituted or unsubstituted phenyl group, a substituted or unsubstituted biphenyl group, a substituted or unsubstituted terphenyl group, a substituted or unsubstituted phenanthryl group, a substituted or unsubstituted dibenzofuran group, or a substituted or unsubstituted dibenzothiophene group.

8. The organic electroluminescence device of claim 5, wherein Ar₁ and Ar₂ are each independently an aryl group having 6 to 30 carbon atoms for forming a ring, the aryl group being an unsubstituted aryl group or an aryl group substituted with at least one selected from a halogen atom, a cyano group, an alkyl group having 1 to 20 carbon atoms, an alkoxy group having 1 to 10 carbon atoms, an aryloxy group having 1 to 20 carbon atoms, an alkylthio group having 1 to 10 carbon atoms, an arylthio group having 1 to 20 carbon atoms, a triarylsilyl group having 18 to 50 carbon atoms, and an adamantyl group, or
a heteroaryl group having 2 to 30 carbon atoms for forming a ring, the heteroaryl group being an unsubstituted heteroaryl group or a heteroaryl group substituted with at least one selected from a halogen atom, a cyano group, an alkyl group having 1 to 20 carbon atoms, an alkoxy group having 1 to 10 carbon atoms, an aryloxy group having 1 to 20 carbon atoms, an alkylthio group having 1 to 10 carbon atoms, an arylthio group having 1 to 20 carbon atoms, a triarylsilyl group having 18 to 50 carbon atoms, and an adamantyl group.

9. The organic electroluminescence device of claim 5, wherein Ar₁ and Ar₂ are each independently represented by any one selected from the following Formula A-1 to Formula A-20:

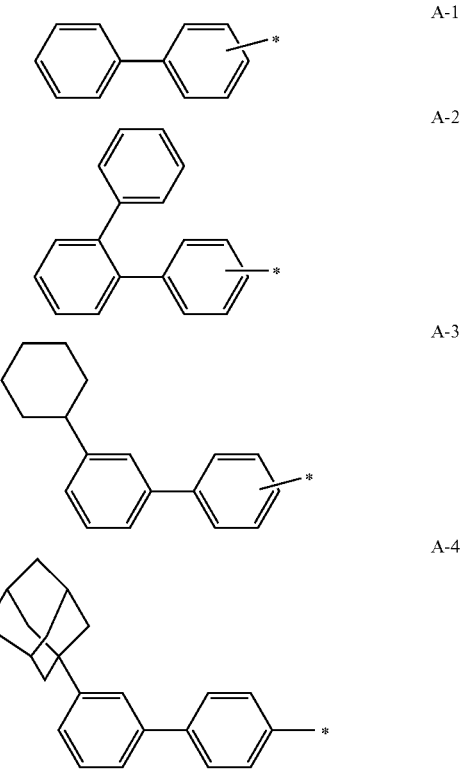

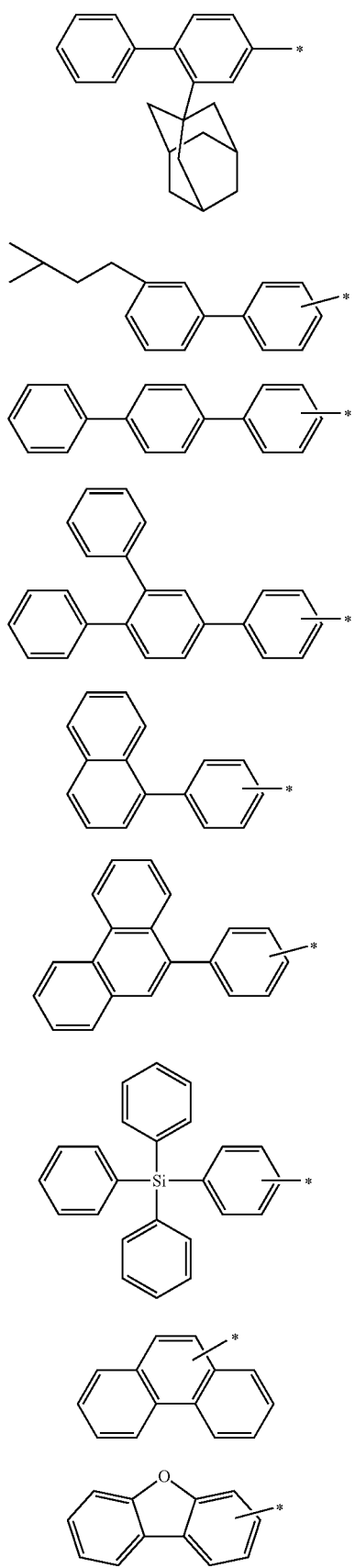
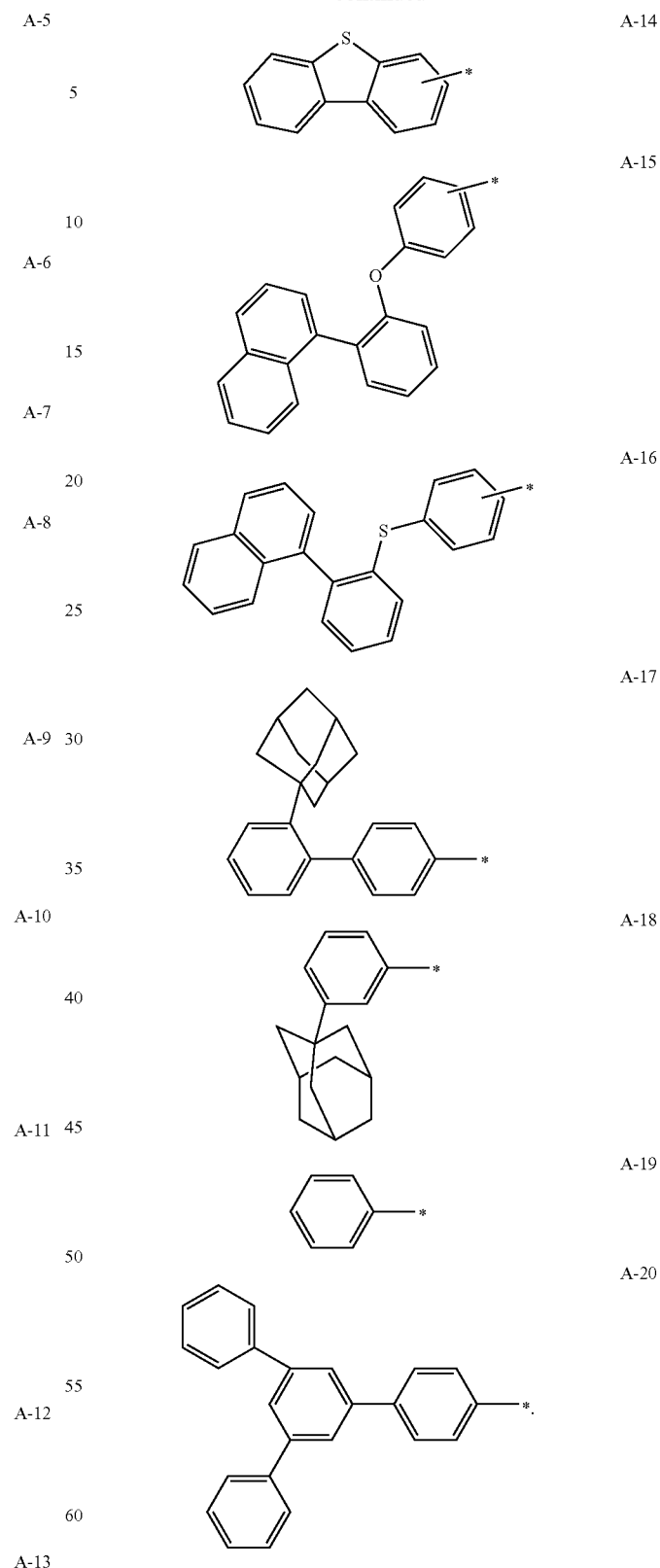
10. The organic electroluminescence device of claim 1, wherein the monoamine compound comprises at least one selected from compounds in the following Compound Group 1 and Compound Group 2:

Compound Group 1
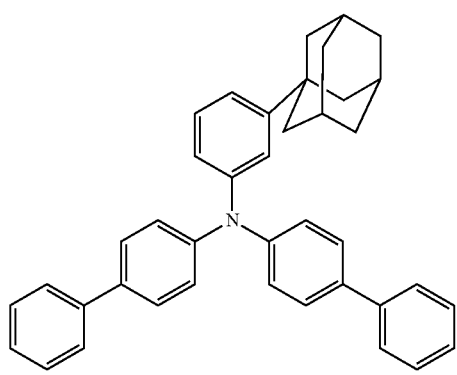
1
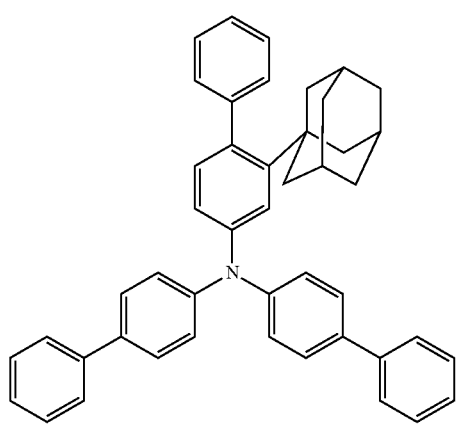
2
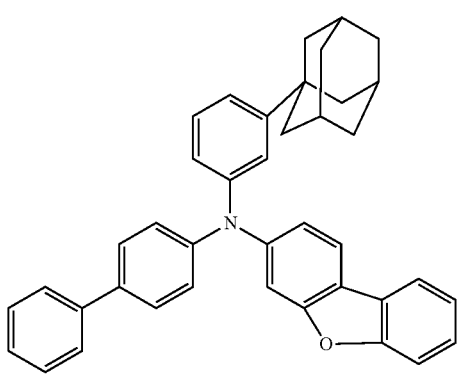
3
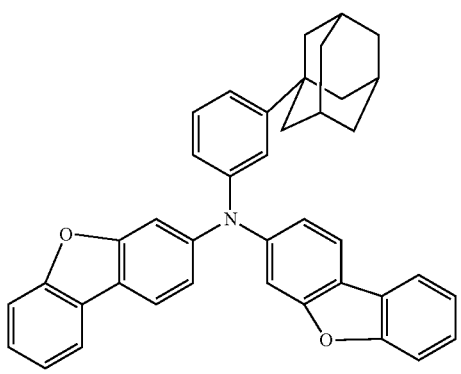
4
-continued
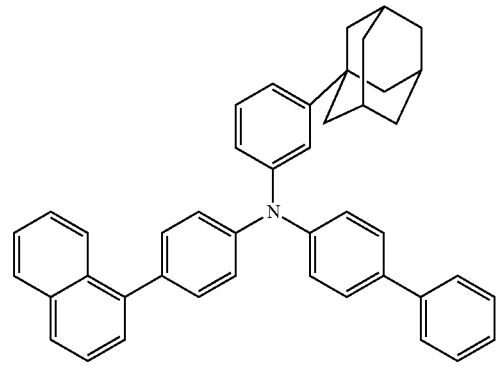
5
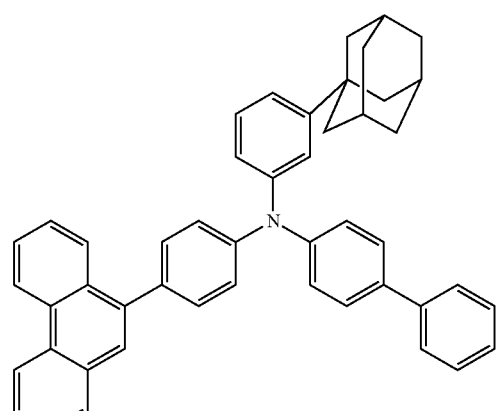
6
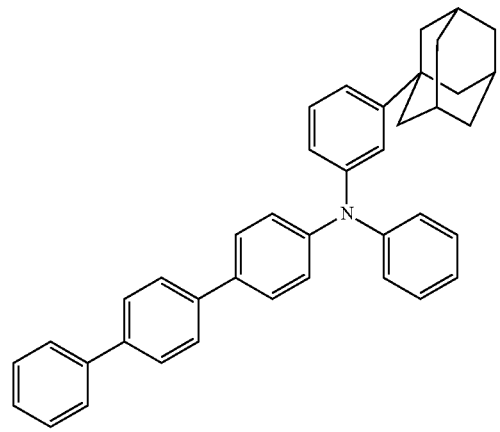
7

125
-continued
8
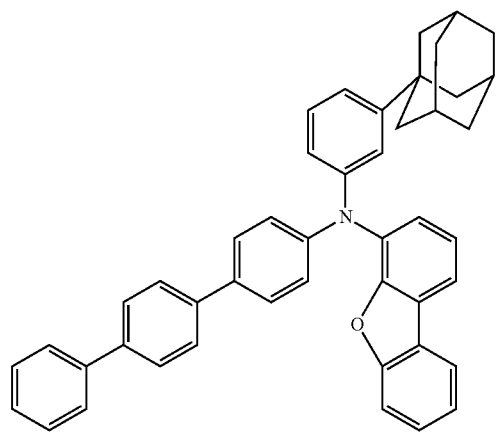
9
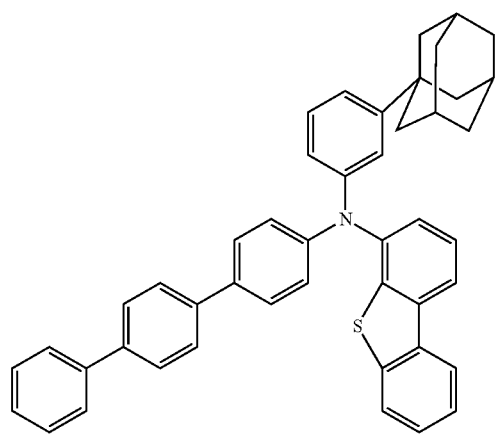
10
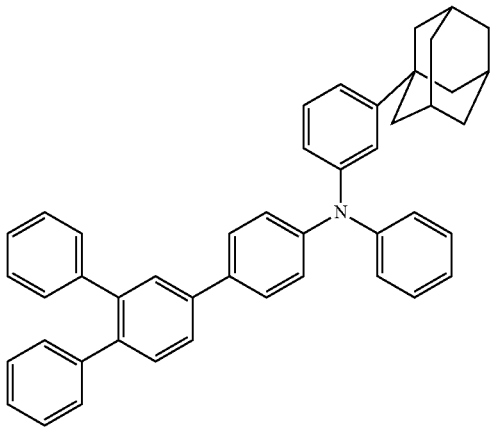
126
-continued
11
12
13
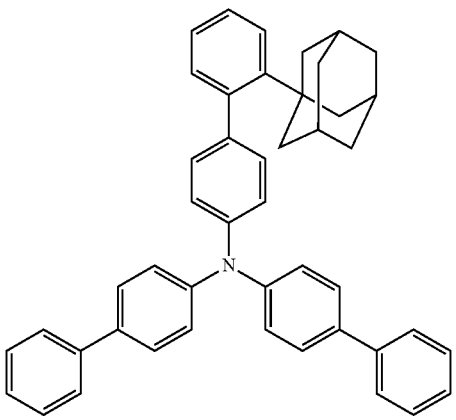

127
-continued
14
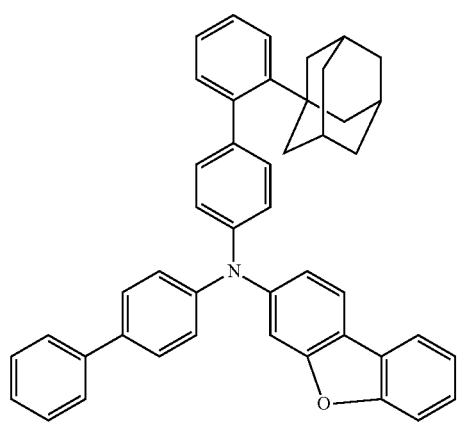
15
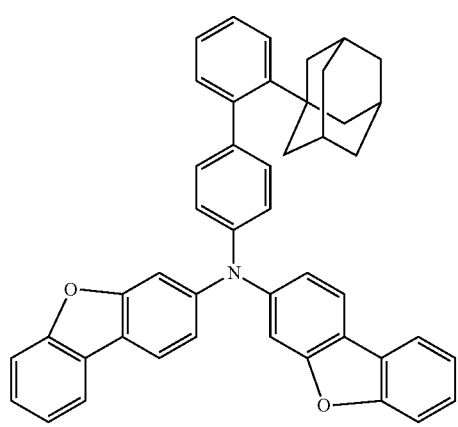
16
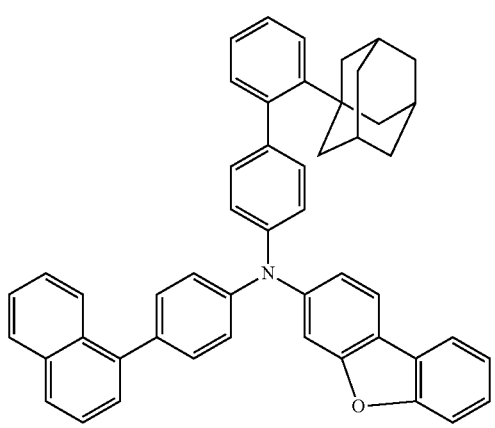
128
-continued
17
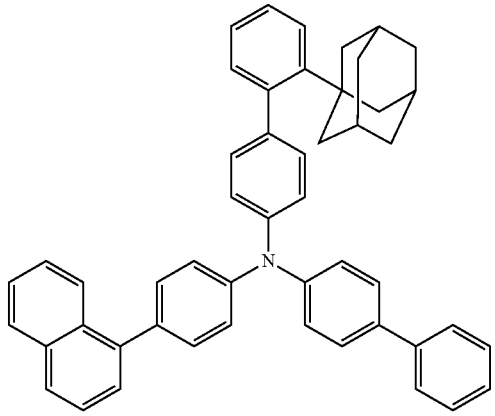
18
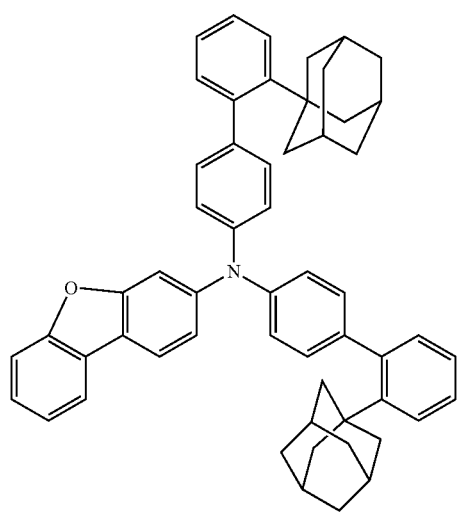
19
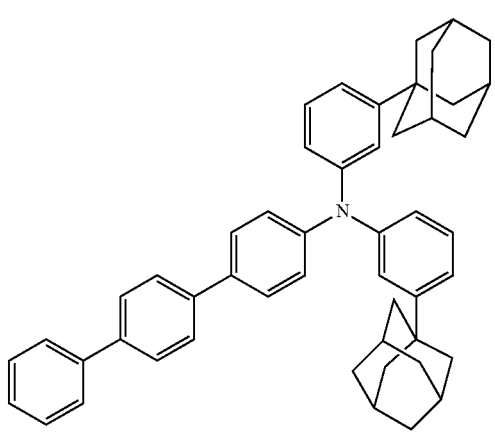

20
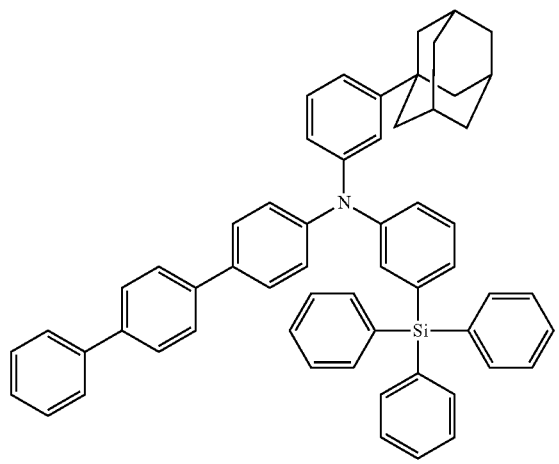
21
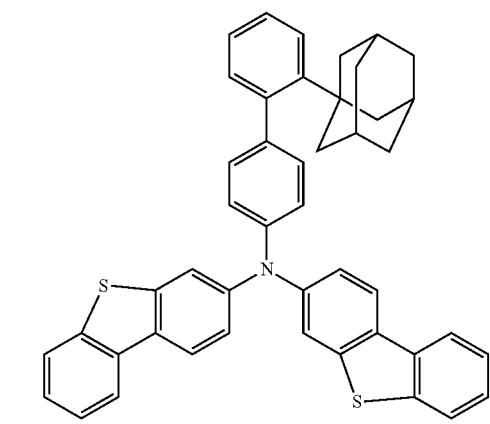
22
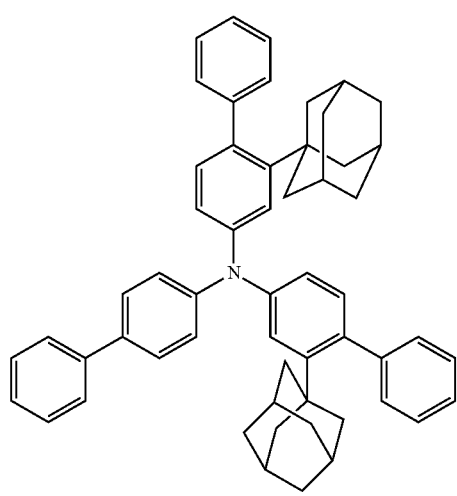
23
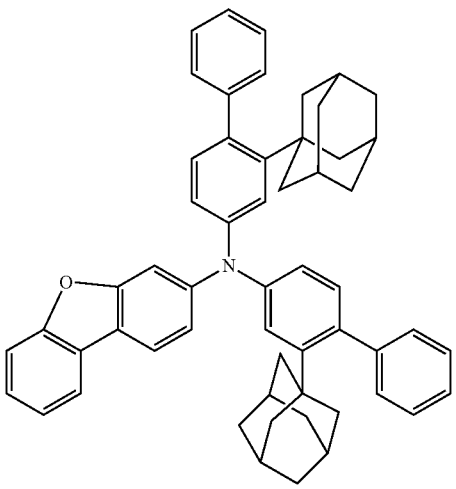
24
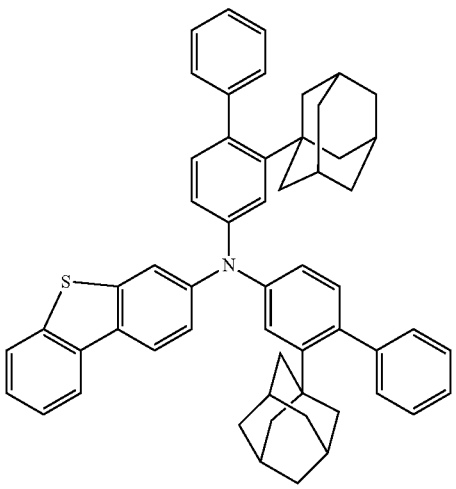
25
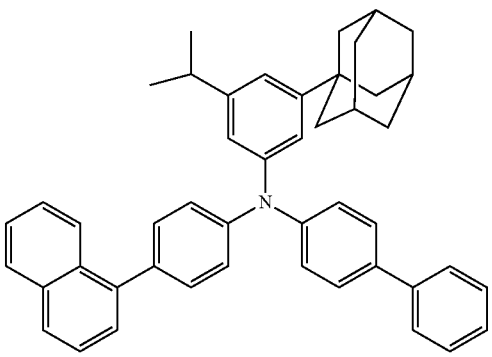

26
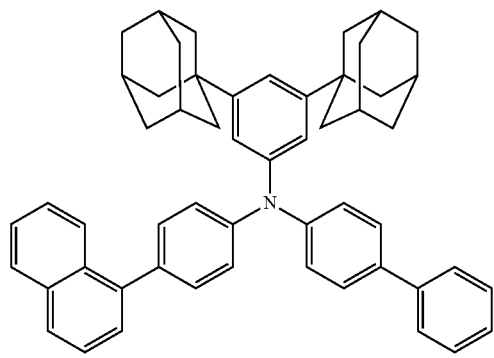
27
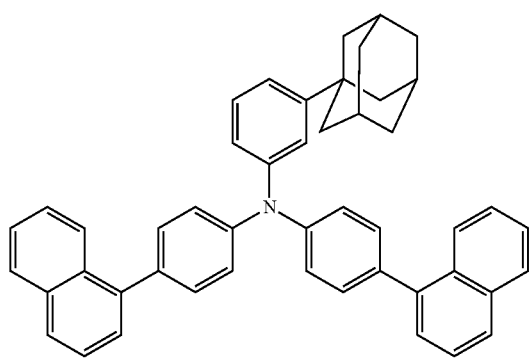
28
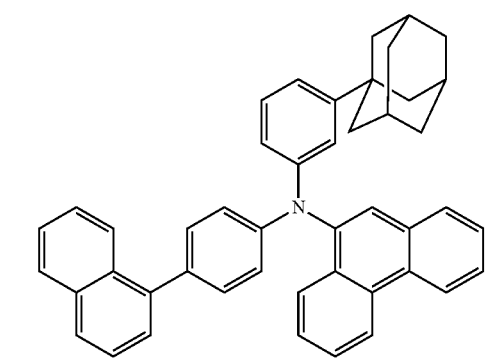
29
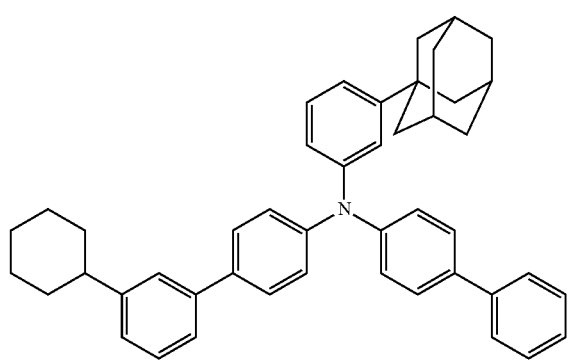
30
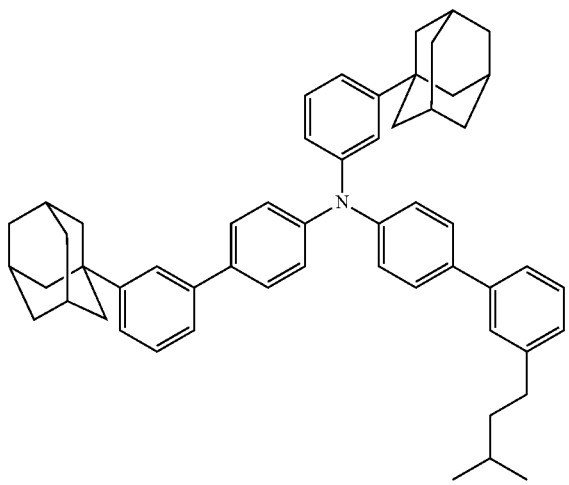
31
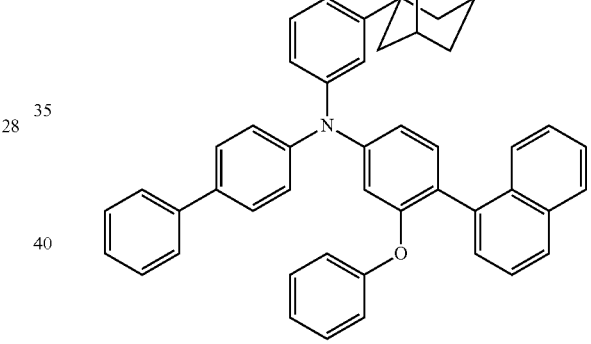
32
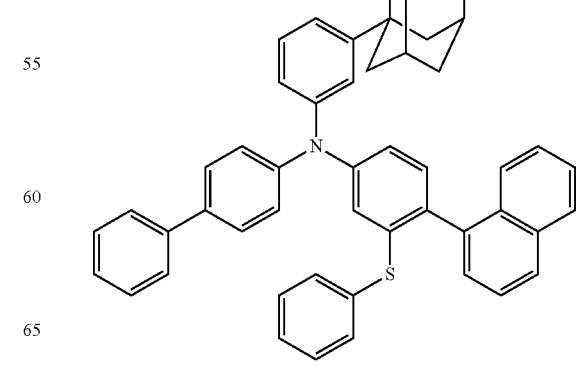

Compound Group 2
33
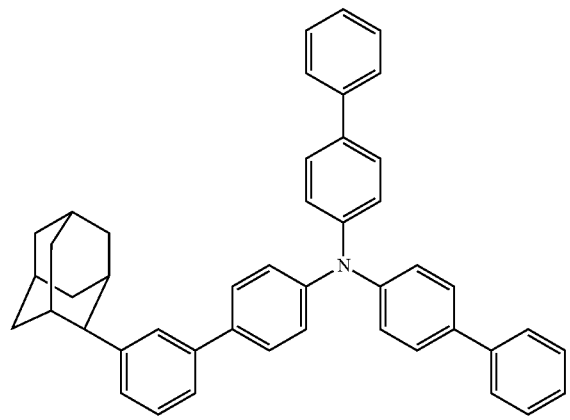
34
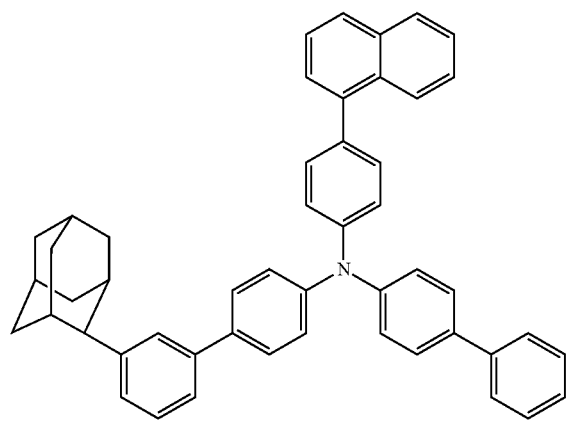
35
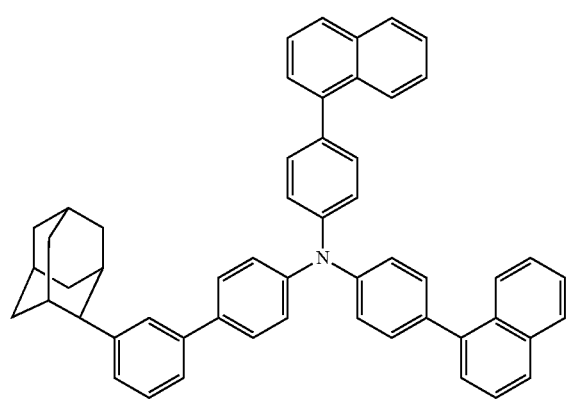
36
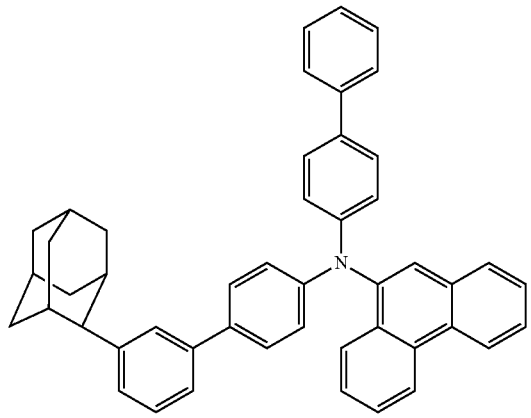
37
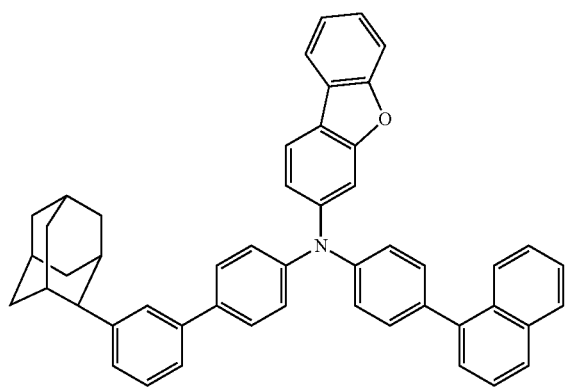
38
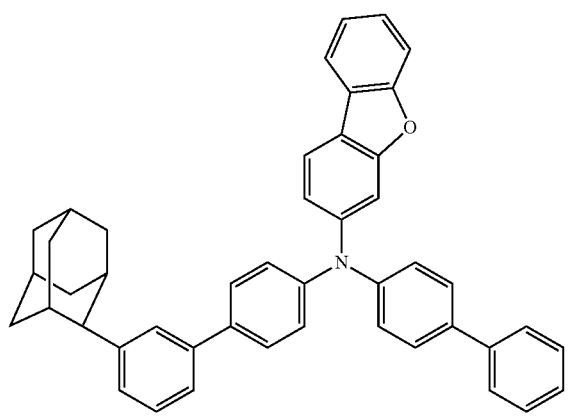

39
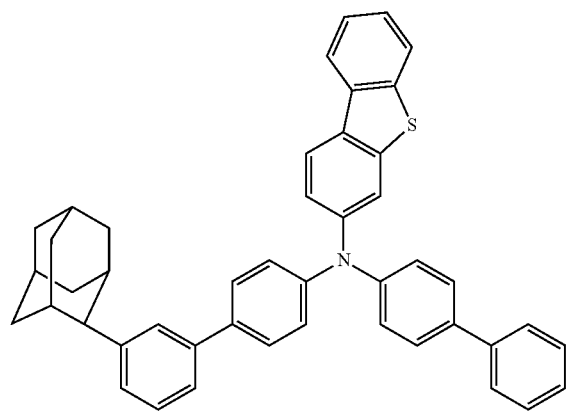
40
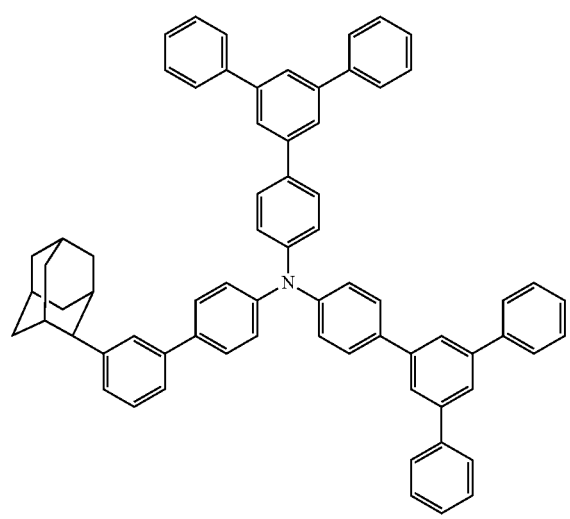
41
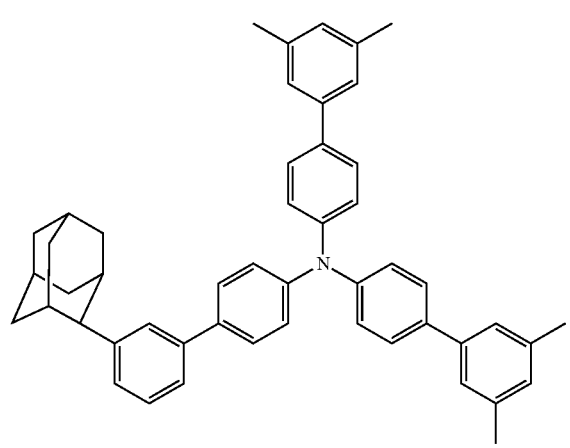
42
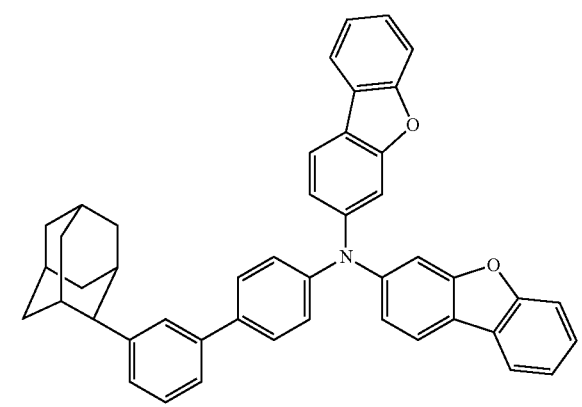
43
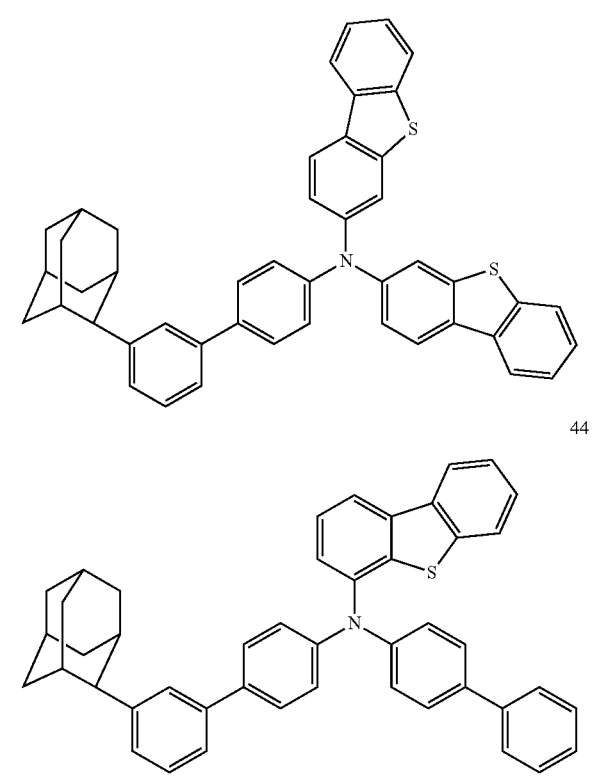

-continued
46
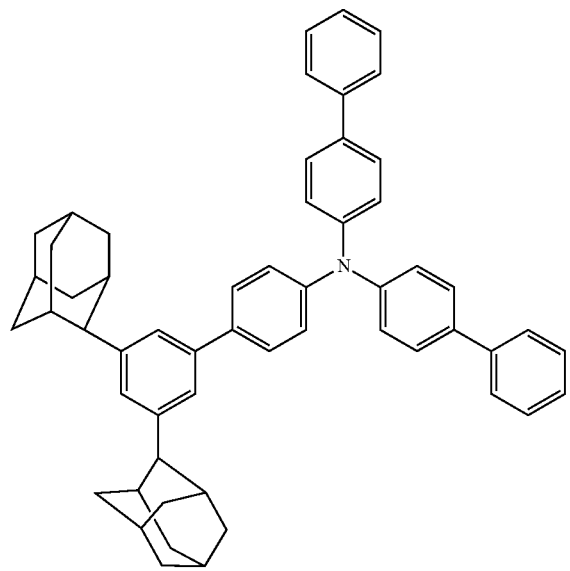
47
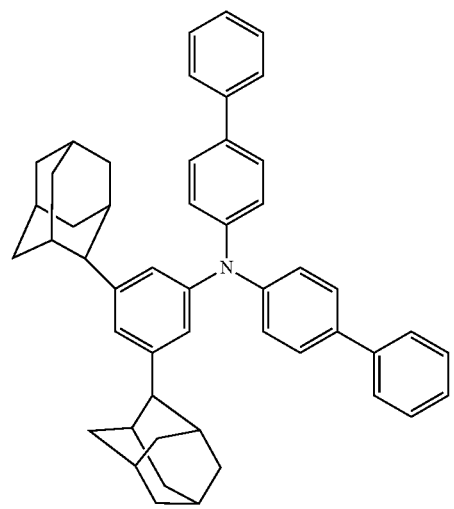
48
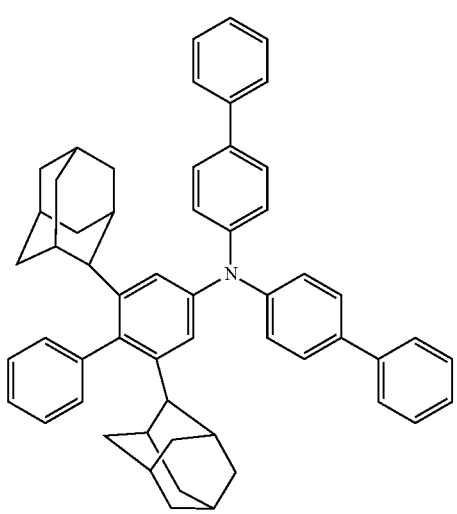
-continued
49
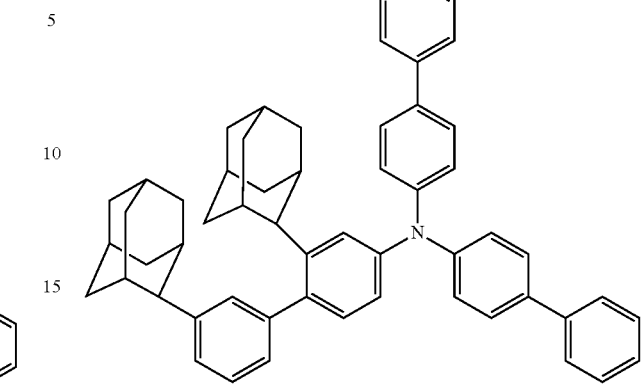
50
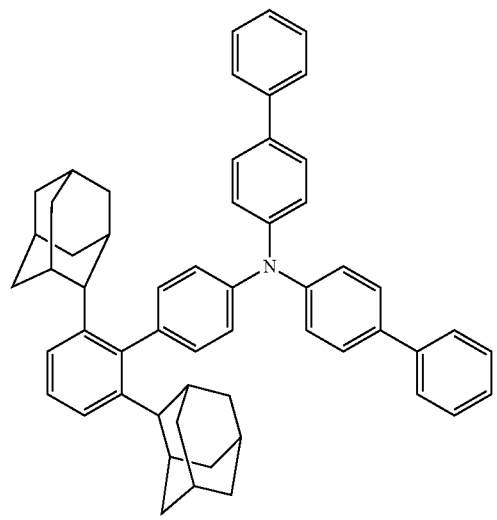
51
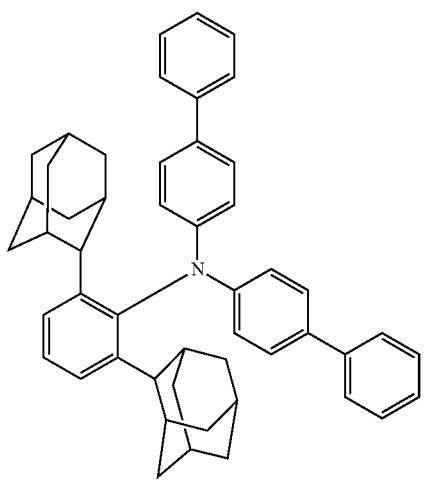

52
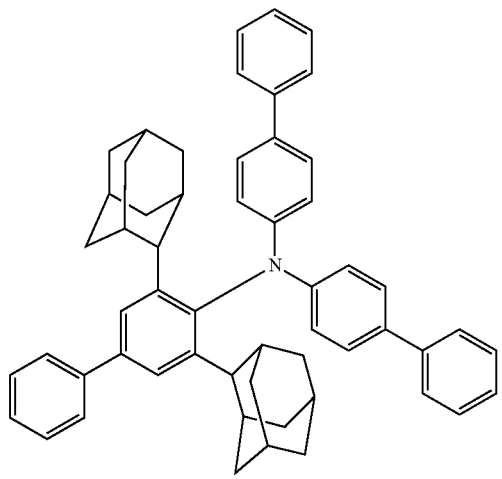
53
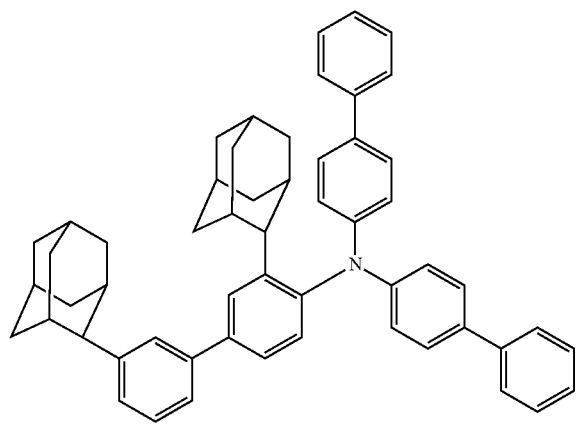
54
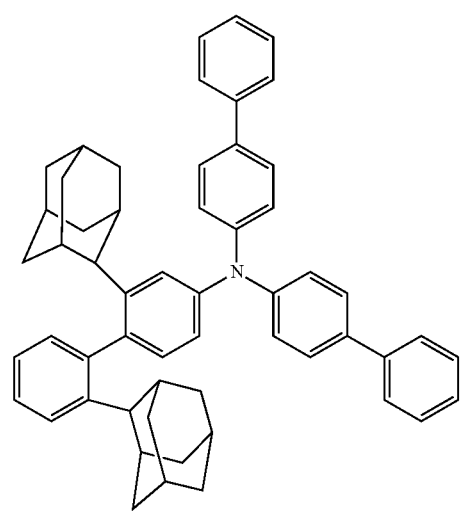
55
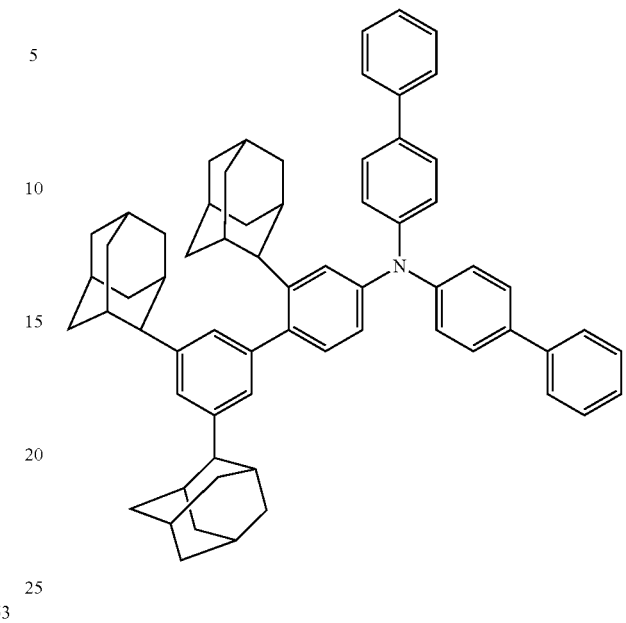
56
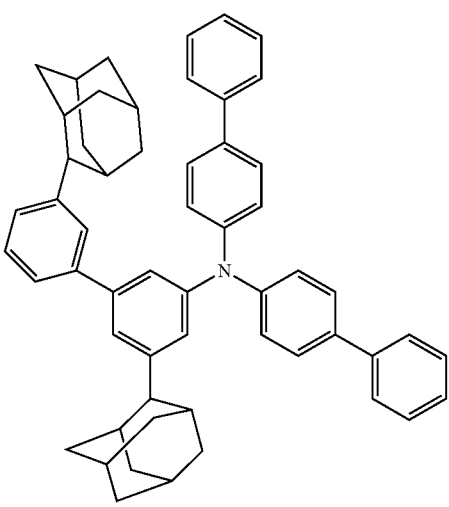
57

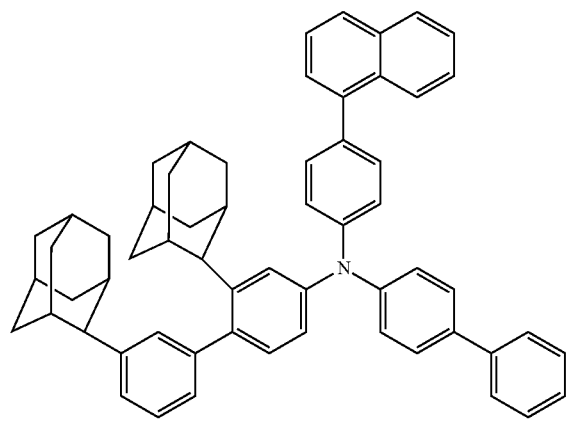
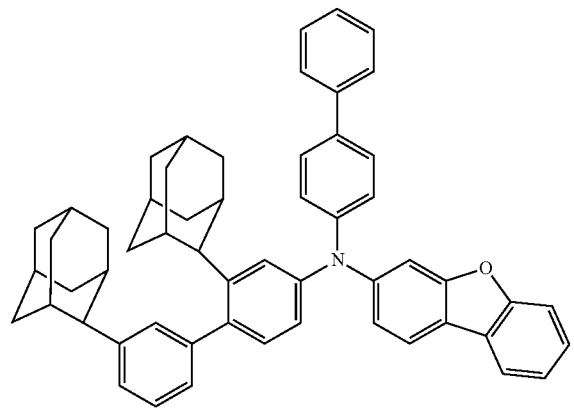
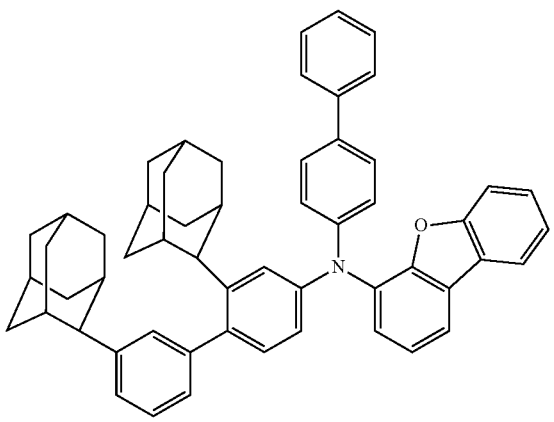
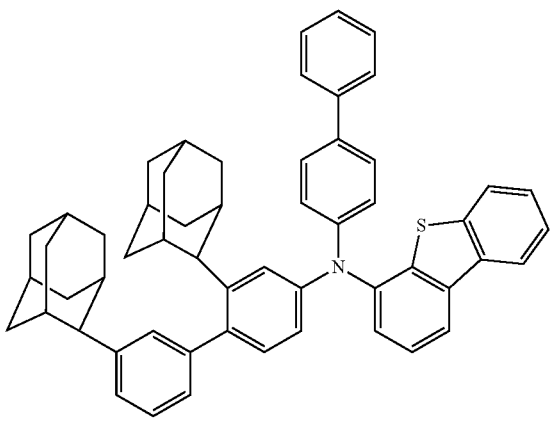

143
-continued
65
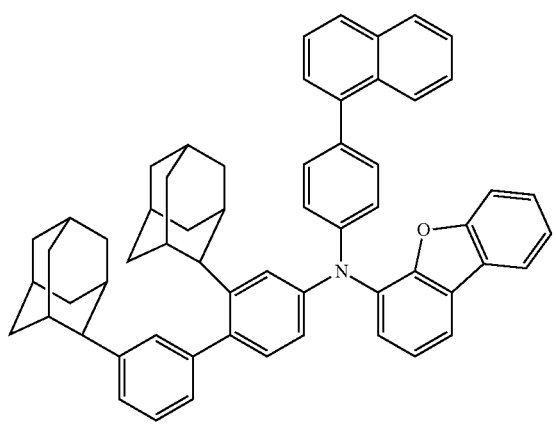
66
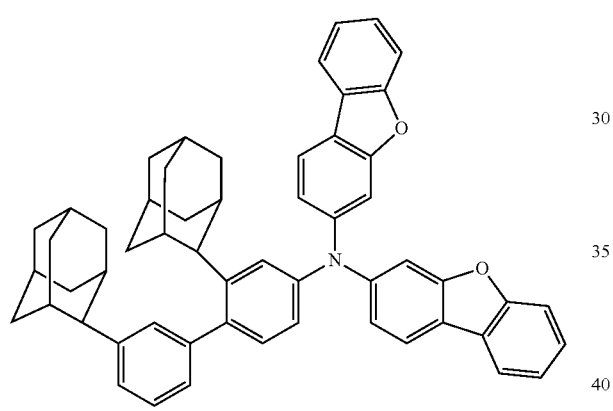
67
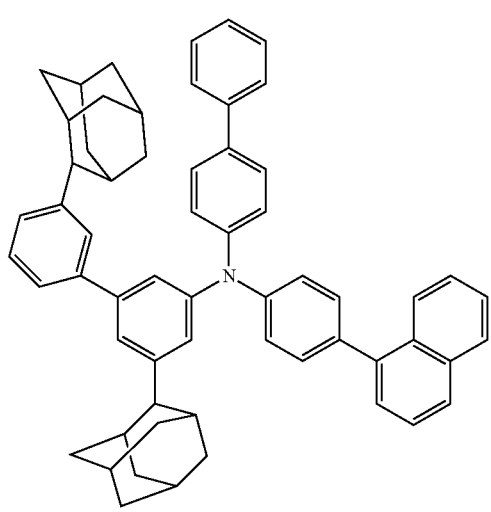
144
-continued
68
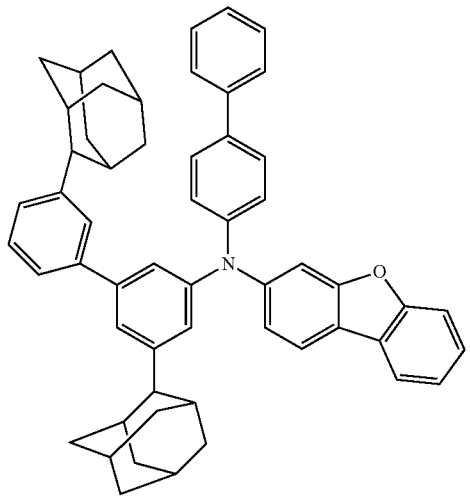
69
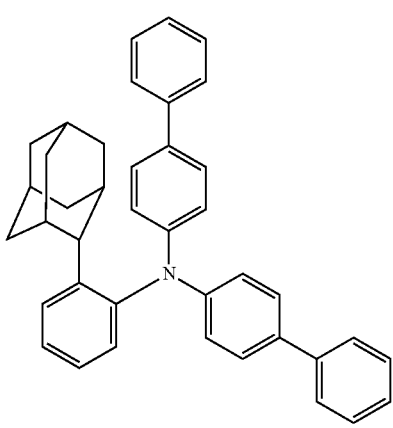
70
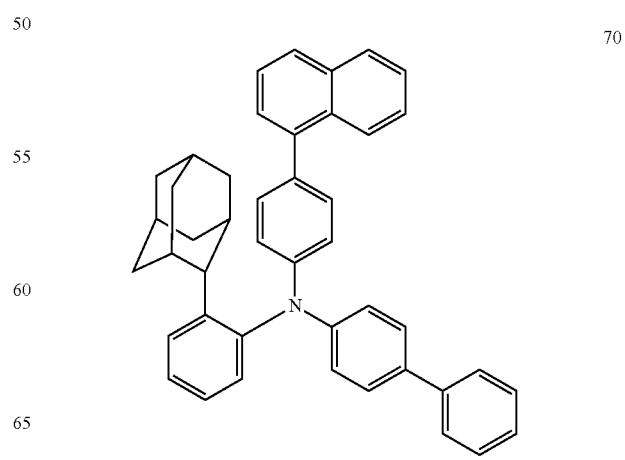

71
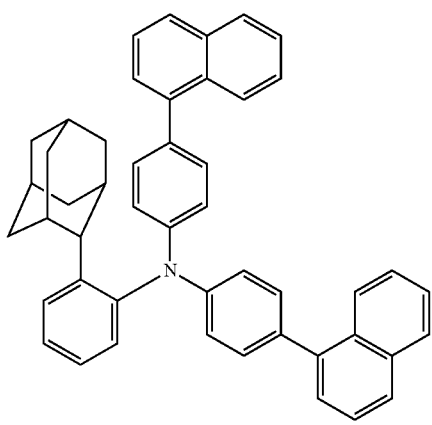
72
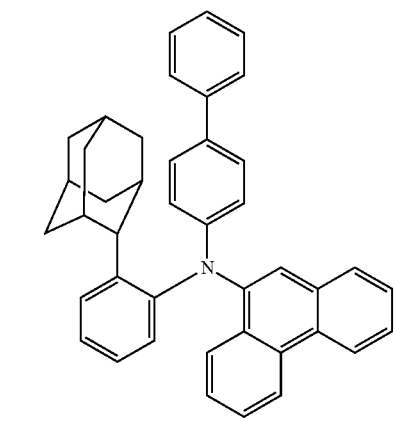
73
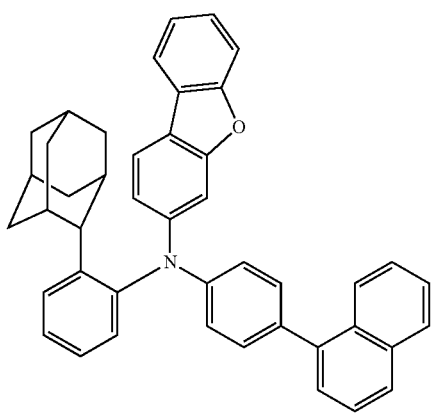
74
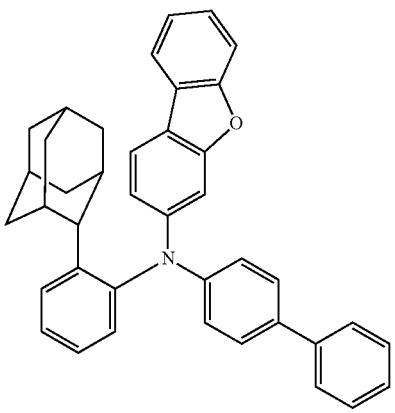
75
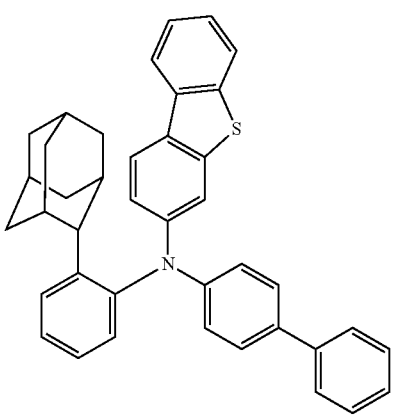
76
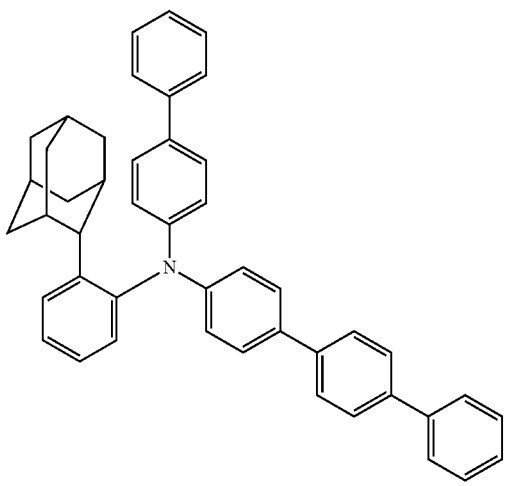

147
-continued
77
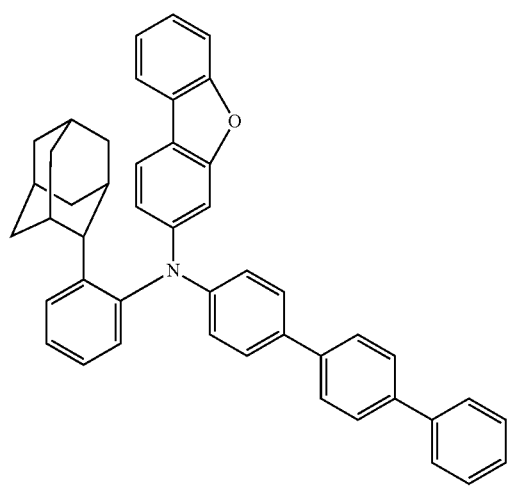
78
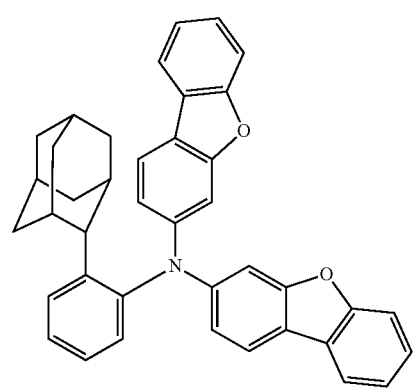
79
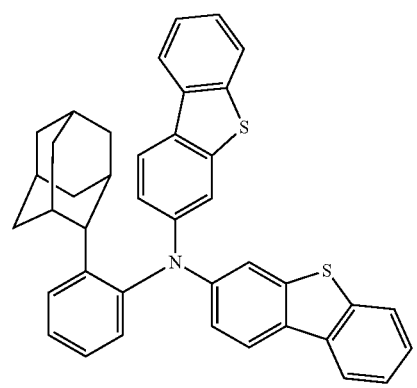
80
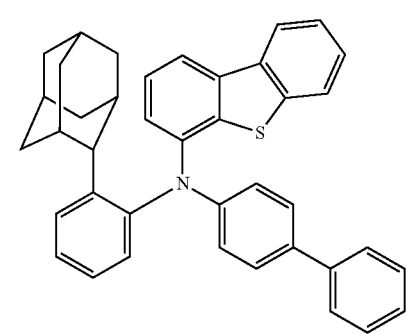
148
-continued
81
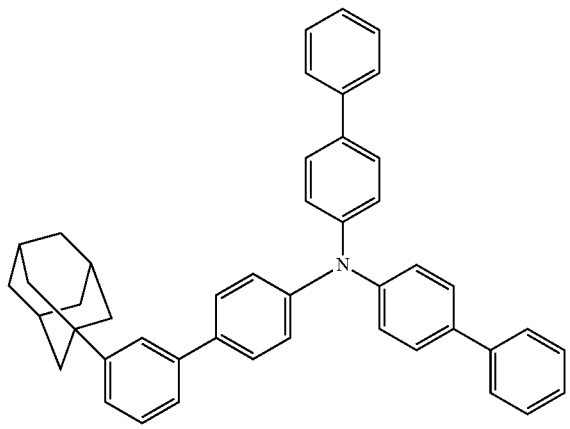
82
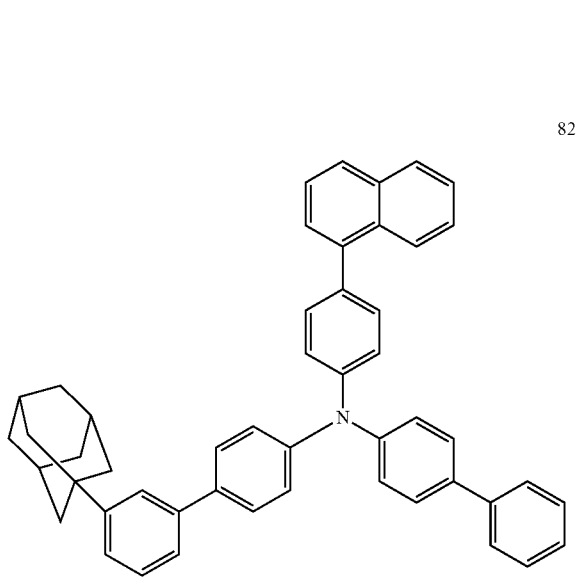
83
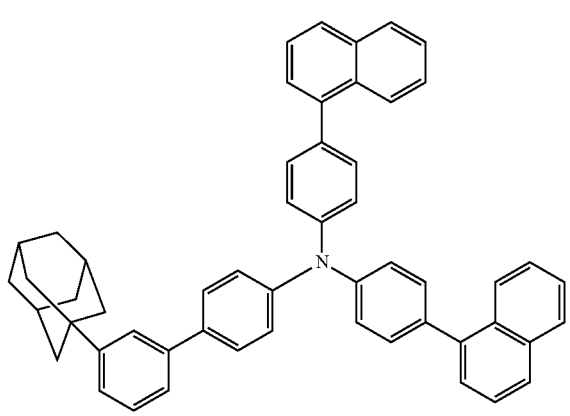

84
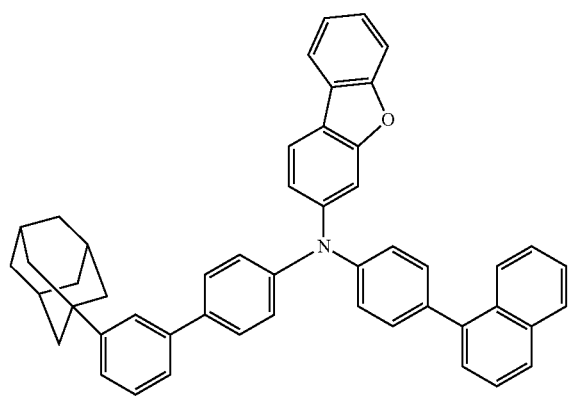
85
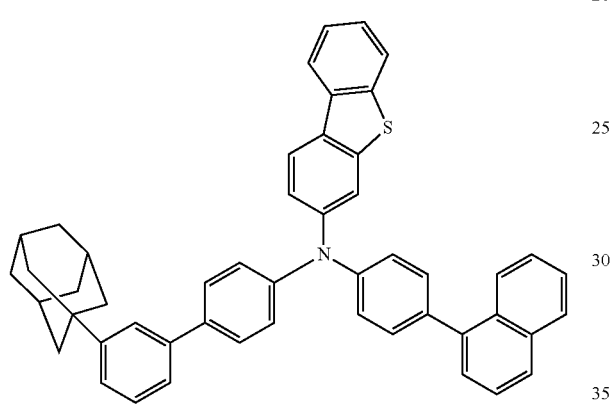
86
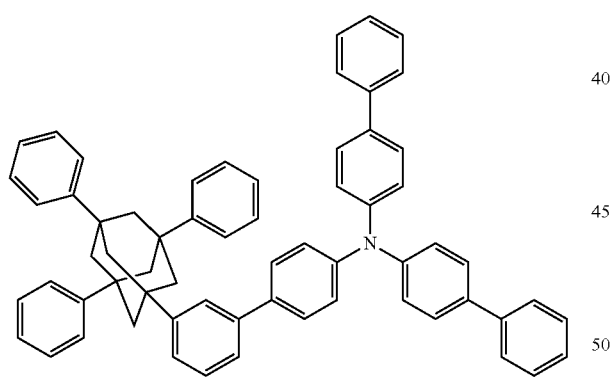
87
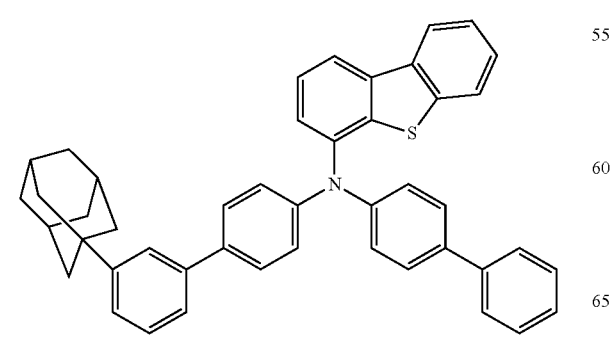
88
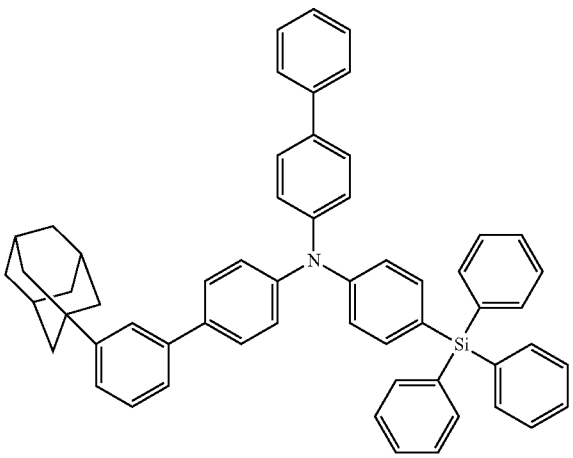
89
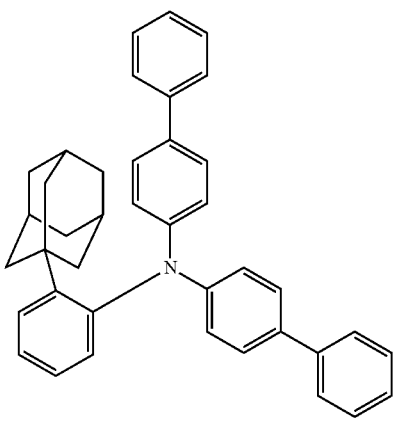
90
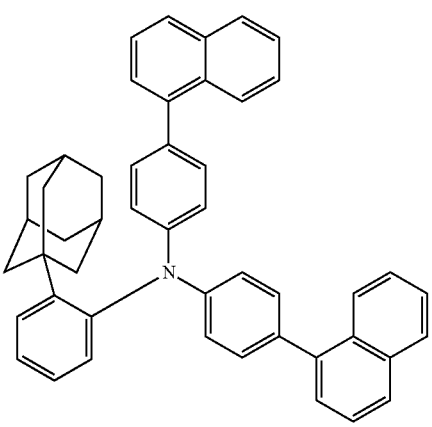

91

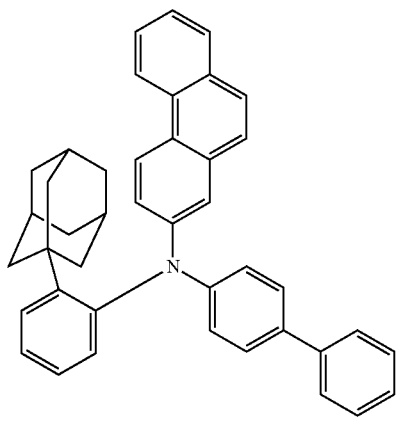

92

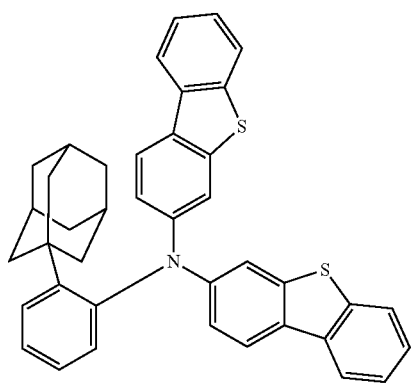

93

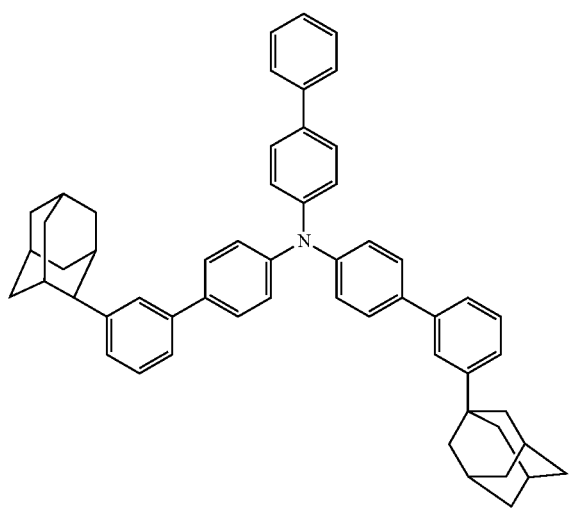

94

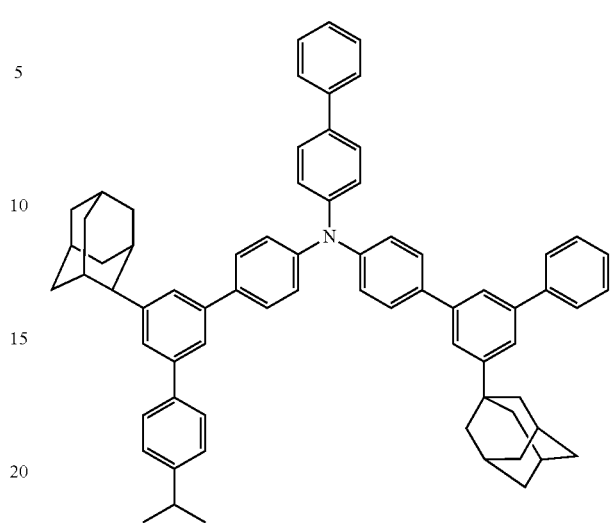

95

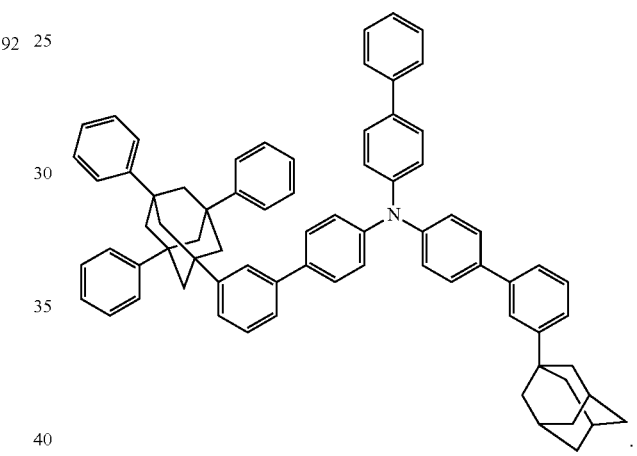

11. A monoamine compound represented by the following Formula 1:

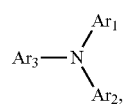

Formula 1 wherein, in Formula 1,
at least one selected from $Ar_1$, $Ar_2$ and $Ar_3$ is represented by the following Formula 2, and the remaining ones of $Ar_1$, $Ar_2$ and $Ar_3$ are each independently a substituted or unsubstituted aryl group having 6 to 30 carbon atoms for forming a ring, or a substituted or unsubstituted heteroaryl group having 2 to 30 carbon atoms for forming a ring:

Formula 2

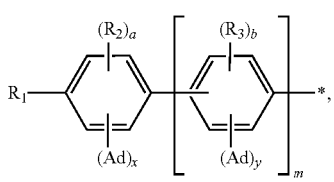

in Formula 2, $R_1$ to $R_3$ are each independently a hydrogen atom, a deuterium atom, a halogen atom, a cyano group, a substituted or unsubstituted silyl group, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, "m" is 0 or 1, "a", "b", "x" and "y" are each independently an integer of 0 to 4, wherein, if "m" is 0, "x" is an integer of 1 or more, and if "m" is 1, "x+y" is an integer of 1 or more, Ad is represented by the following Formula 3:

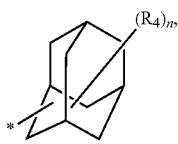

Formula 3 in Formula 3, $R_4$ is a hydrogen atom, a deuterium atom, a halogen atom, a cyano group, a substituted or unsubstituted silyl group, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, and "n" is an integer of 0 to 15.

12. The monoamine compound of claim 11, wherein Formula 3 is represented by the following Formula 3-1 or Formula 3-2:

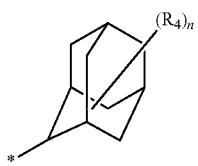

Formula 3-1

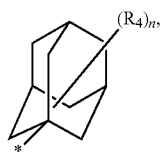

Formula 3-2 in Formula 3-1 and Formula 3-2, $R_4$ and "n" are the same as defined in Formula 3.

13. The monoamine compound of claim 11, wherein Formula 1 is represented by the following Formula 1-A or Formula 1-B:

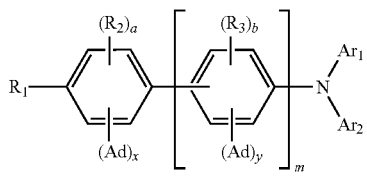

Formula 1-A

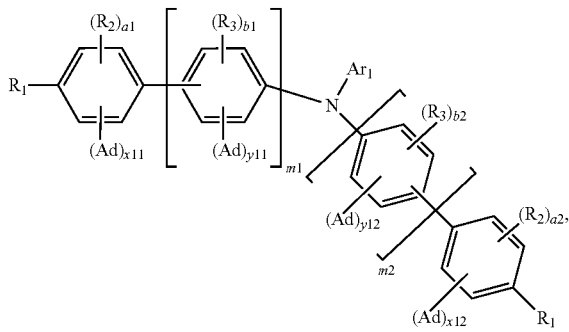

Formula 1-B in Formula 1-B,

"m1" and "m2" are each independently 0 or 1, and

"a1", "a2", "b1", "b2", "x11", "x12", "y11", and "y12" are each independently an integer of 0 to 4, wherein, if "m1" is 0, "x11" is an integer of 1 or more, if "m1" is 1, "x11+y11" is an integer of 1 or more, if "m2" is 0, "x12" is an integer of 1 or more, and if "m2" is 1, "x12+y12" is an integer of 1 or more, and in Formula 1-A and Formula 1-B, $Ar_1$ and $Ar_2$ are the same as defined in Formula 1, and $R_1$ to $R_3$, "a", "b", "b", "x", "y", and Ad are the same as defined in Formula 2.

14. The monoamine compound of claim 13, wherein Formula 1-A is represented by any one selected from the following Formula 1-1 to Formula 1-3:

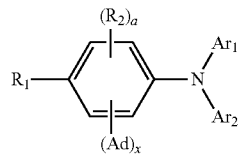

Formula 1-1

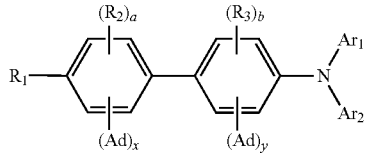

Formula 1-2

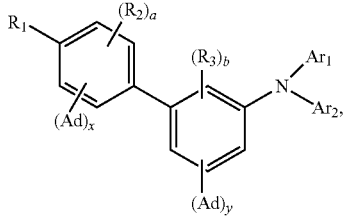

Formula 1-3 in Formula 1-1 to Formula 1-3, $Ar_1$ and $Ar_2$ are the same as defined in Formula 1, and $R_1$ to $R_3$, "a", "b", "x", "y", and Ad are the same as defined in Formula 2.

15. The monoamine compound of claim 14, wherein Formula 1-1 is represented by any one selected from the following Formula 1-1a to Formula 1-1e:

Formula 1-1a

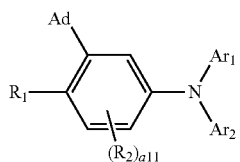

Formula 1-1b

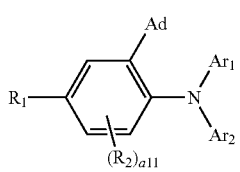

Formula 1-1c

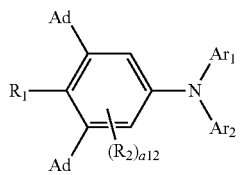

Formula 1-1d

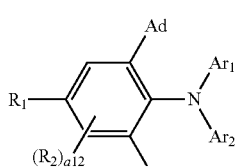

Formula 1-1e

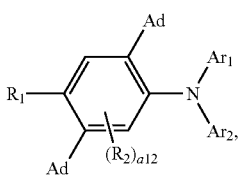

in Formula 1-1a and Formula 1-1b, "a11" is an integer of 0 to 3, in Formula 1-1c, Formula 1-1d, and Formula 1-1e, "a12" is an integer of 0 to 2, and in Formula 1-1a to Formula 1-1e, $Ar_1$ and $Ar_2$ are the same as defined in Formula 1, and $R_1$, $R_2$, and Ad are the same as defined in Formula 2.

16. The monoamine compound of claim 14, wherein Formula 1-2 is represented by any one selected from the following Formula 1-2a to Formula 1-2c:

Formula 1-2a

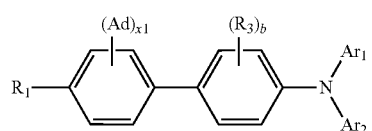

Formula 1-2b

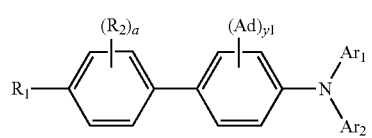

Formula 1-2c

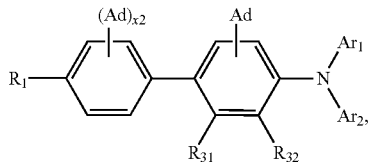

in Formula 1-2a, "x1" is 1 or 2,
in Formula 1-2b, "y1" is 1 or 2,
in Formula 1-2c, "x2" is 1 or 2,
$R_{31}$ and $R_{32}$ are each independently a hydrogen atom, a deuterium atom, a halogen atom, a cyano group, a substituted or unsubstituted silyl group, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, and in Formula 1-2a to Formula 1-2c, $Ar_1$ and $Ar_2$ are the same as defined in Formula 1, and "a", "b", $R_1$, $R_2$, $R_3$, and Ad are the same as defined in Formula 2.

17. The monoamine compound of claim 14, wherein Formula 1-3 is represented by any one selected from the following Formula 1-3a to Formula 1-3c:

Formula 1-3a

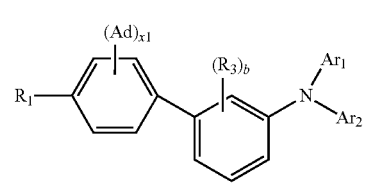

Formula 1-3b

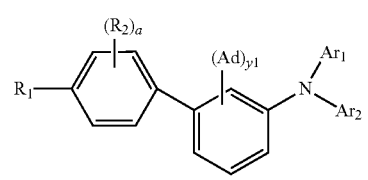

Formula 1-3c

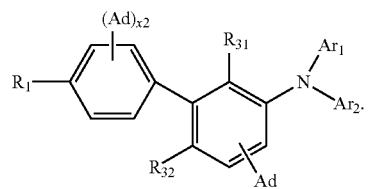

in Formula 1-3a, "x1" is 1 or 2,
in Formula 1-3b, "y1" is 1 or 2,
in Formula 1-3c, "x2" is 1 or 2,
$R_{31}$ and $R_{32}$ are each independently a hydrogen atom, a deuterium atom, a halogen atom, a cyano group, a substituted or unsubstituted silyl group, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, and in Formula 1-3a to Formula 1-3c, $Ar_1$ and $Ar_2$ are the same as defined in Formula 1, and "a", "b", $R_1$, $R_2$, $R_3$, and Ad are the same as defined in Formula 2.

18. The monoamine compound of claim 13, wherein $Ar_1$ and $Ar_2$ are each independently a substituted or unsubstituted phenyl group, a substituted or unsubstituted biphenyl group, a substituted or unsubstituted terphenyl group, a substituted or unsubstituted phenanthryl group, a substituted or unsubstituted dibenzofuran group, or a substituted or unsubstituted dibenzothiophene group.

19. The monoamine compound of claim 13, wherein $Ar_1$ and $Ar_2$ are each independently an aryl group having 6 to 30 carbon atoms for forming a ring, the aryl group being an unsubstituted aryl group or an aryl group substituted with at least one selected from a halogen atom, a cyano group, an alkyl group having 1 to 20 carbon atoms, an alkoxy group having 1 to 10 carbon atoms, an aryloxy group having 1 to 20 carbon atoms, an alkylthio group having 1 to 10 carbon atoms, an arylthio group having 1 to 20 carbon atoms, a triarylsilyl group having 18 to 50 carbon atoms, and an adamantyl group, or a heteroaryl group having 2 to 30 carbon atoms for forming a ring, the heteroaryl group being an unsubstituted heteroaryl group or a heteroaryl group substituted with at least one selected from a halogen atom, a cyano group, an alkyl group having 1 to 20 carbon atoms, an alkoxy group having 1 to 10 carbon atoms, an aryloxy group having 1 to 20 carbon atoms, an alkylthio group having 1 to 10 carbon atoms, an arylthio group having 1 to 20 carbon atoms, a triarylsilyl group having 18 to 50 carbon atoms, and an adamantyl group.

20. The monoamine compound of claim 13, wherein $Ar_1$ and $Ar_2$ are each independently represented by any one selected from the following Formula A-1 to Formula A-20:

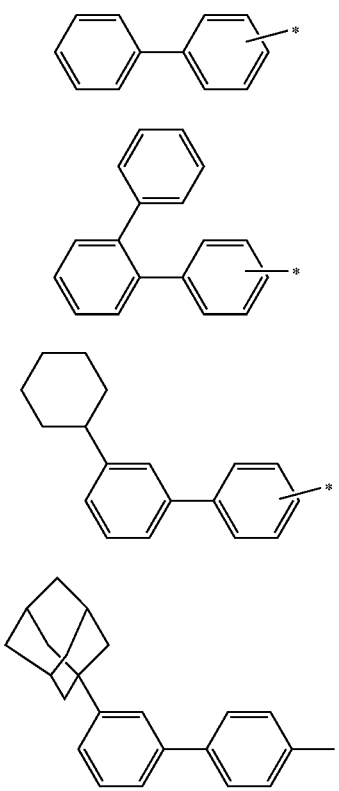

A-1

A-2

A-3

A-4

-continued

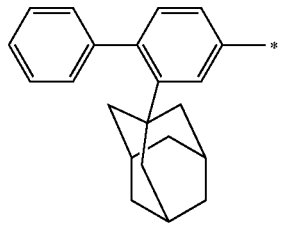

A-5

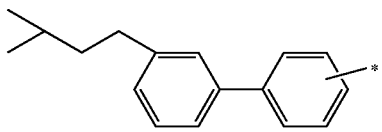

A-6

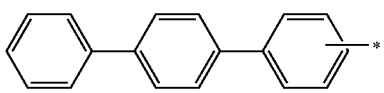

A-7

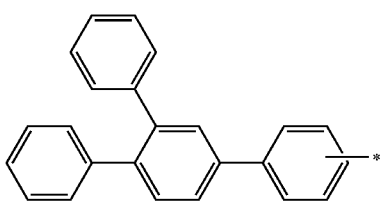

A-8

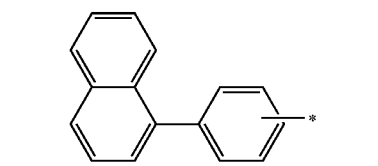

A-9

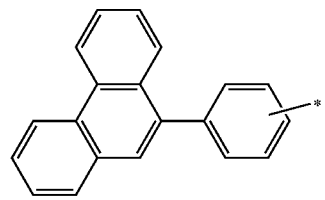

A-10

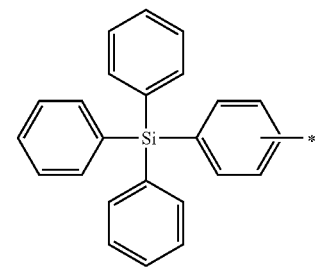

A-11

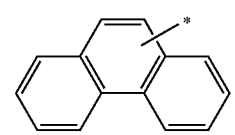

A-12

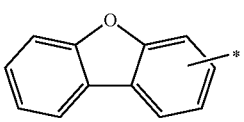

A-13

-continued
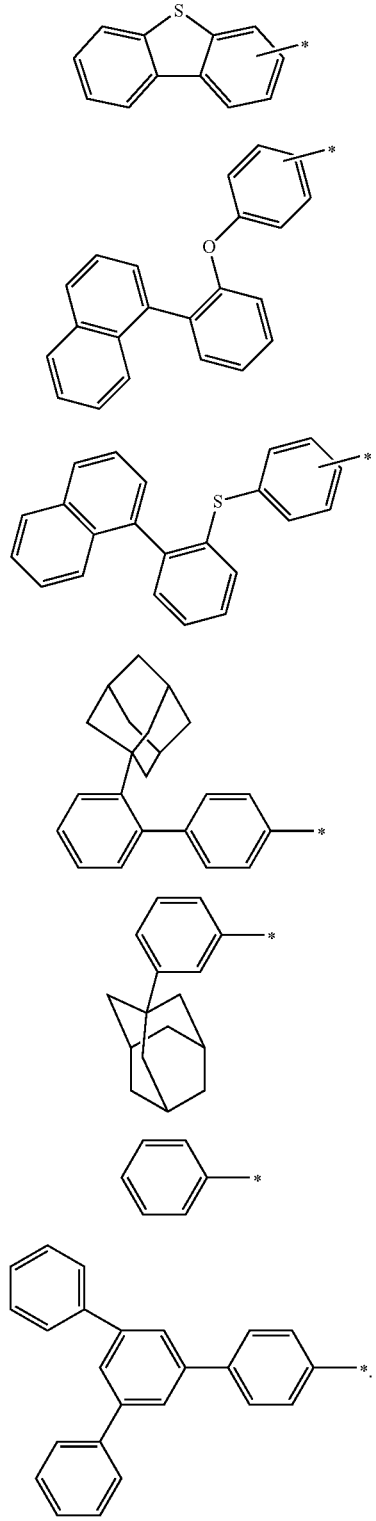
A-14
A-15
A-16
A-17
A-18
A-19
A-20
21. The monoamine compound of claim 11, wherein R₁ is a hydrogen atom or an unsubstituted phenyl group.
22. The monoamine compound of claim 11, wherein the monoamine compound represented by Formula 1 is represented by any one selected from compounds in the following Compound Group 1 and Compound Group 2:
Compound Group 1
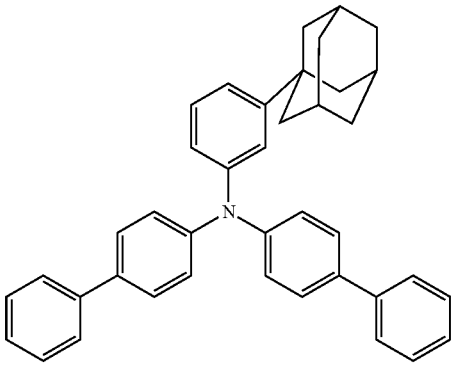
1
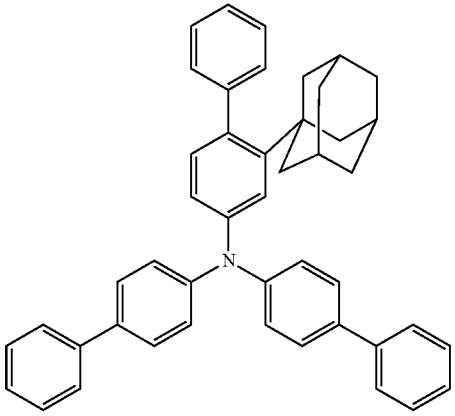
2
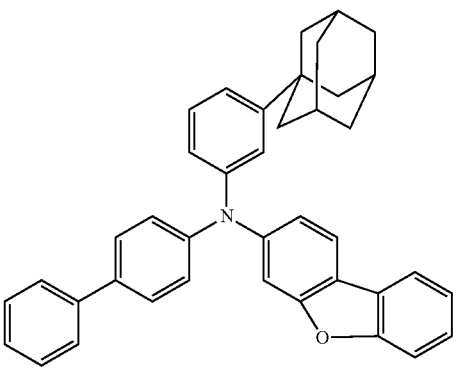
3
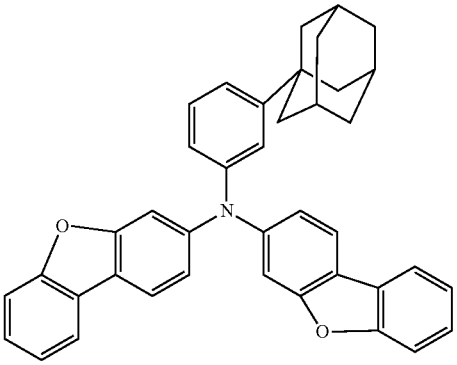
4

161
-continued
5
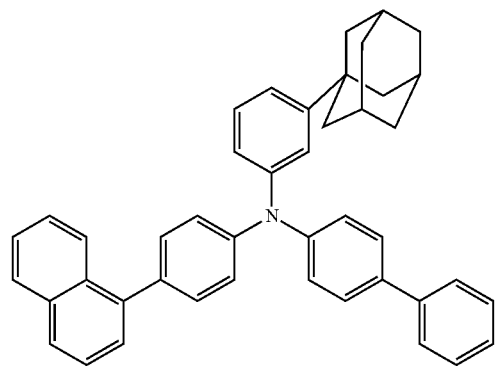
6
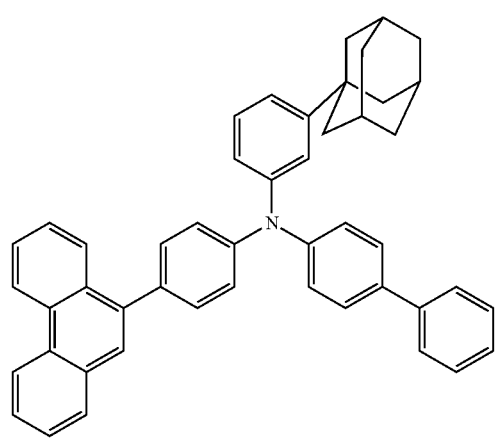
7
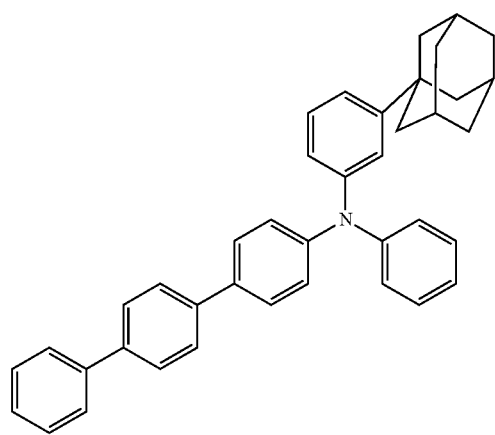
162
-continued
8
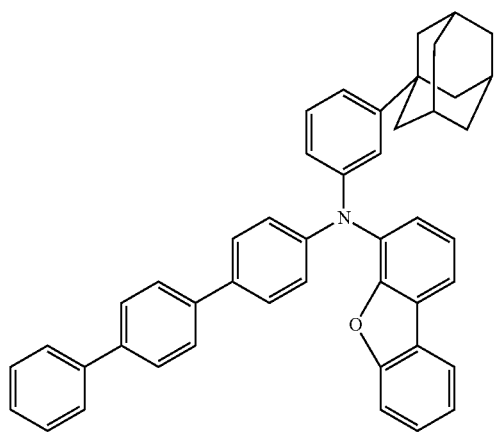
9
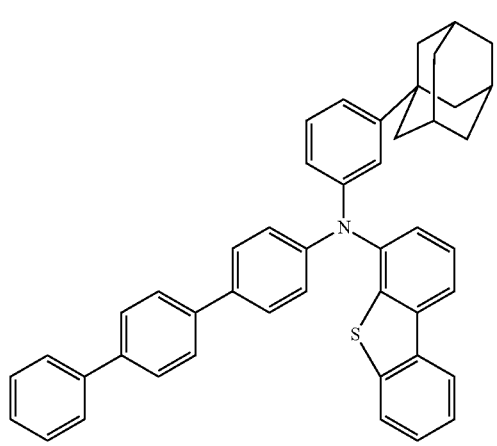
10

163
-continued
11
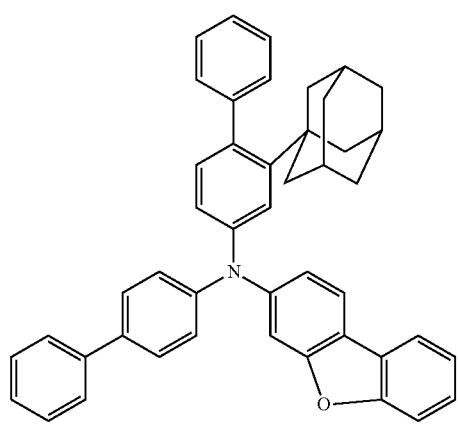
12
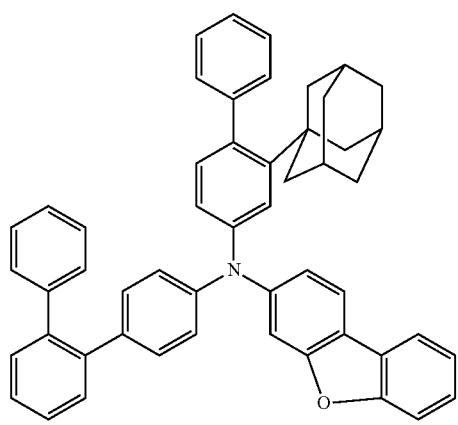
13
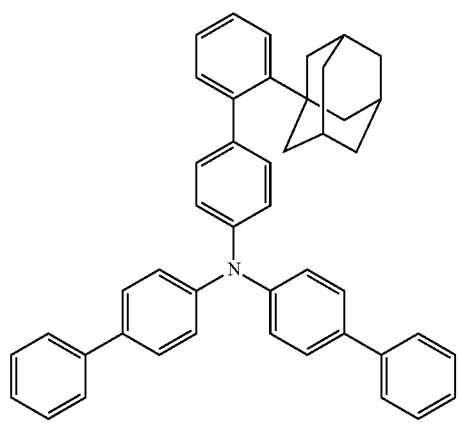
164
-continued
14
15
16
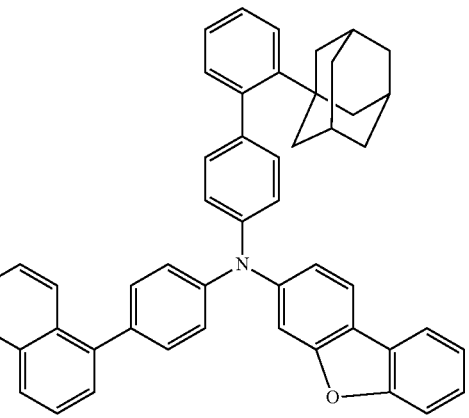

17
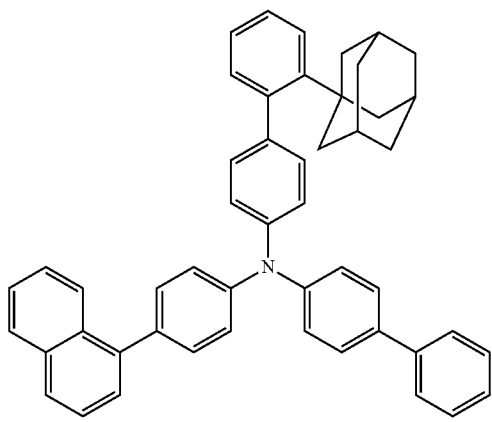
18
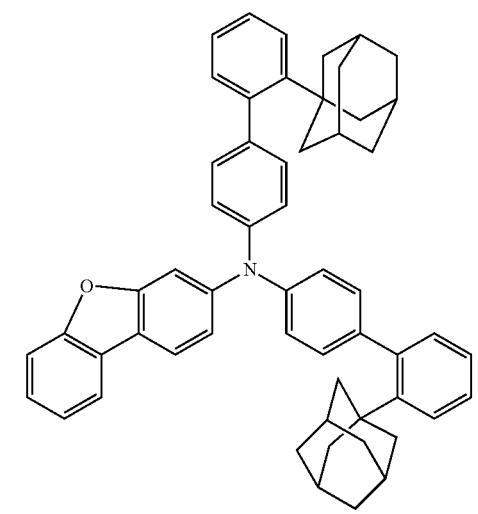
19
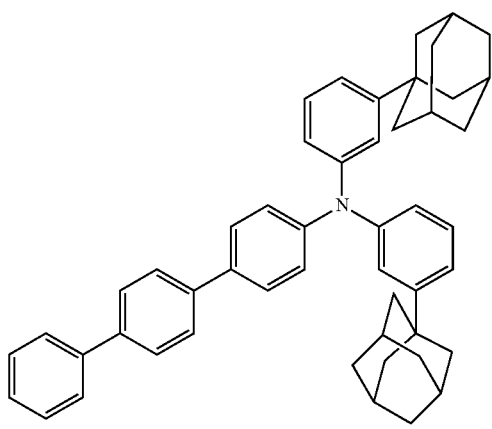
20
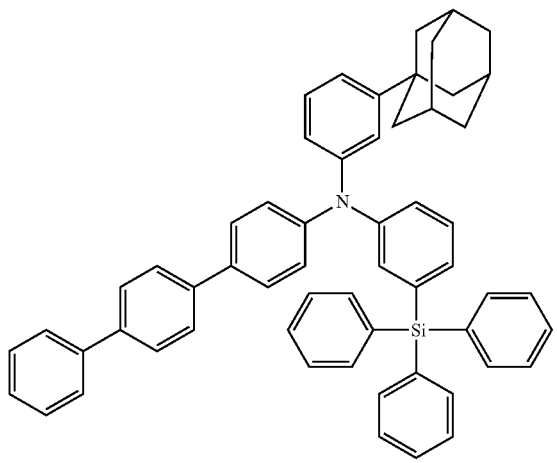
21
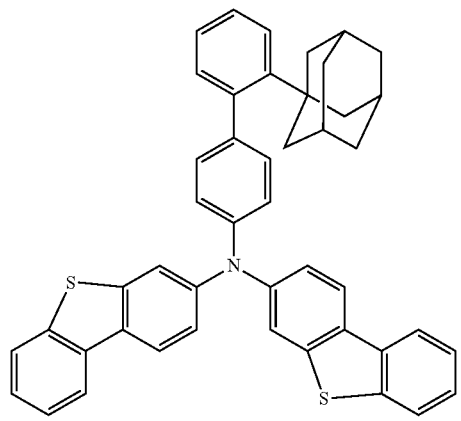
22
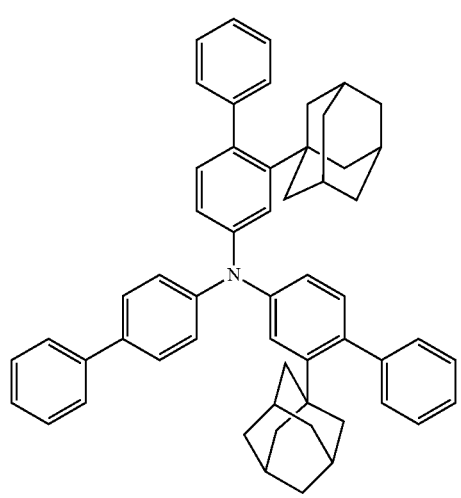

23
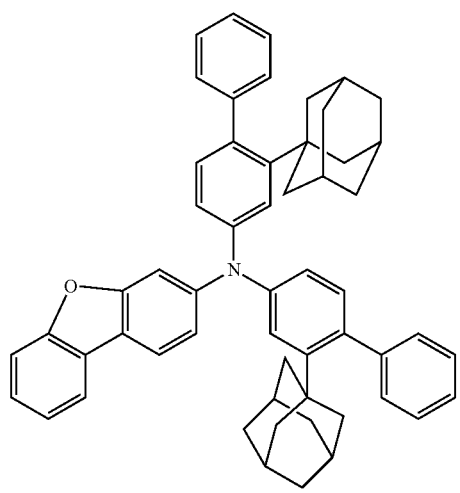
24
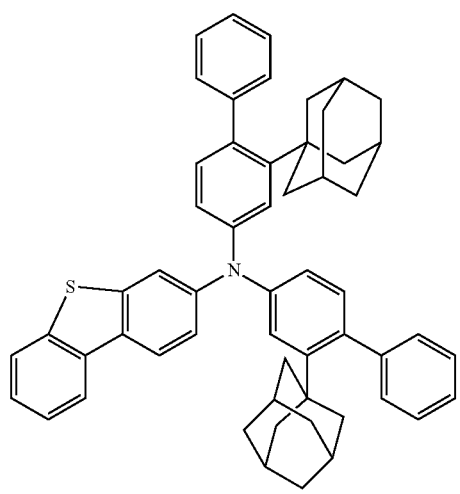
25
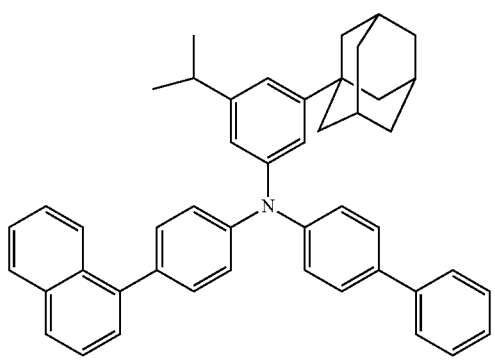
26
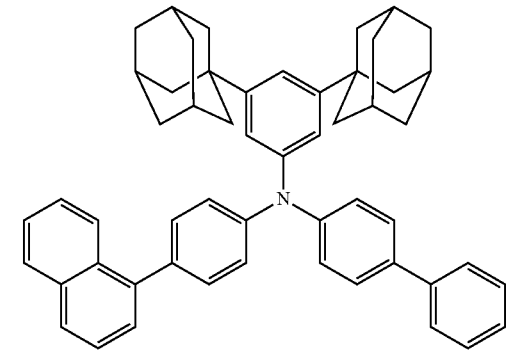
27
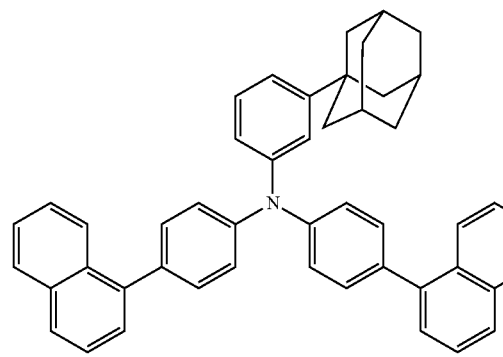
28
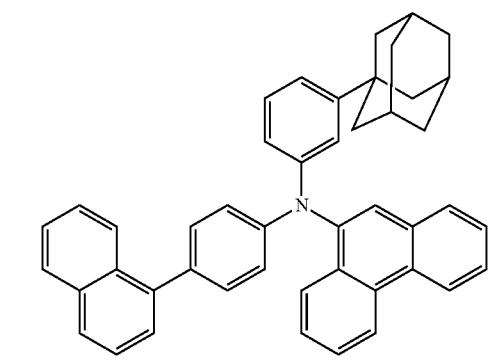
29
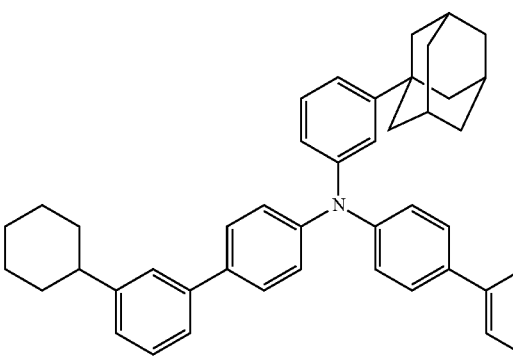

30
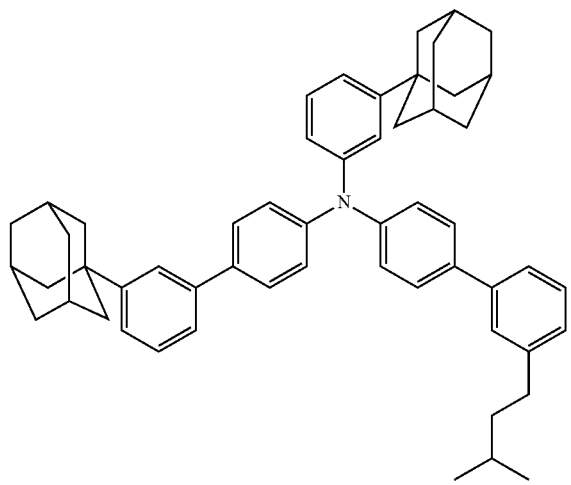
31
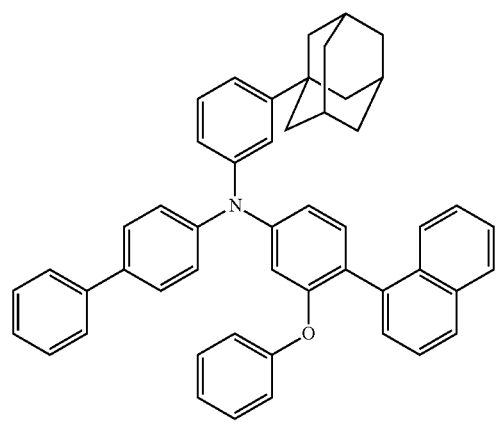
32
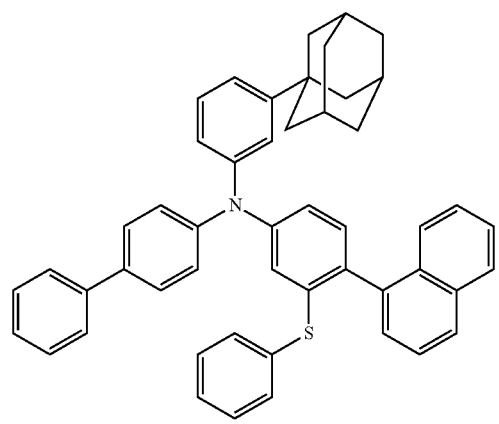
Compound Group 2
33
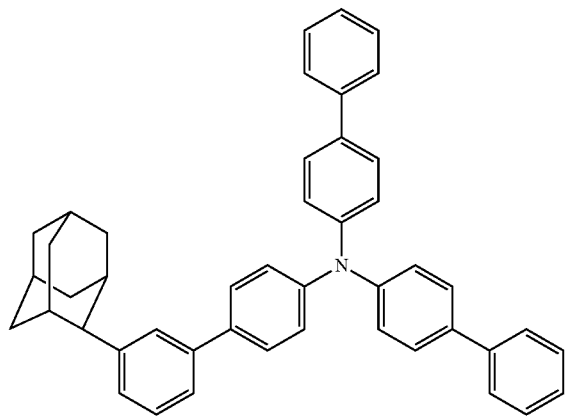
34
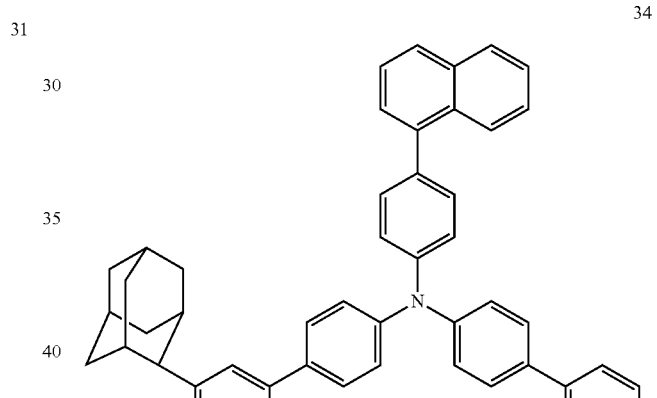
35
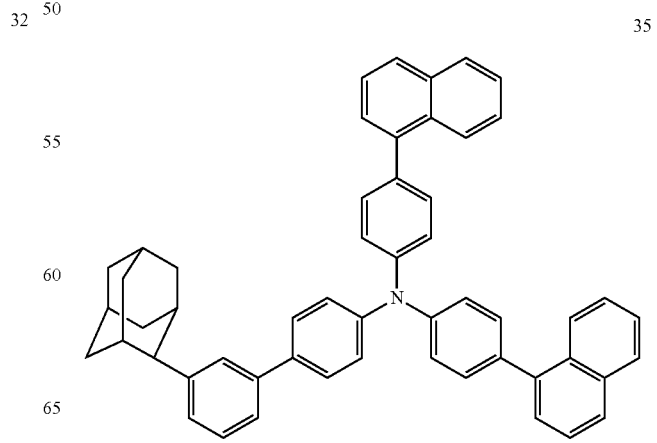

36
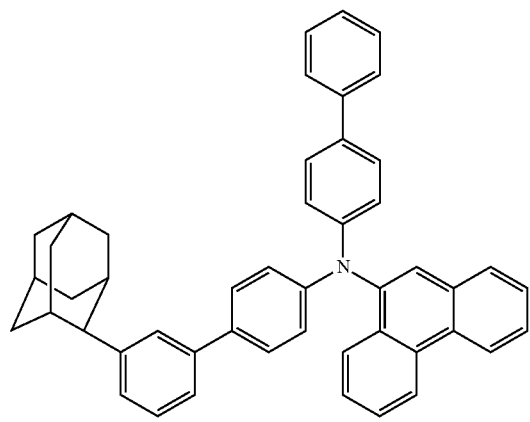
37
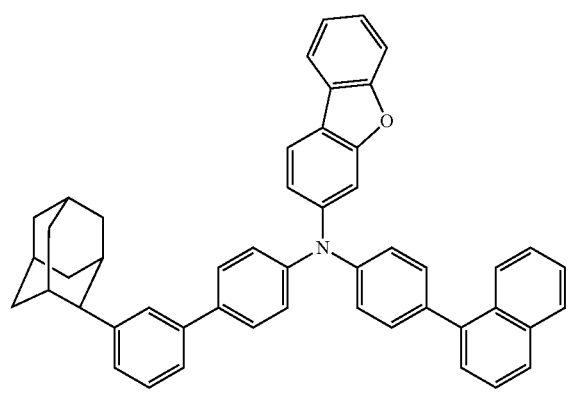
38
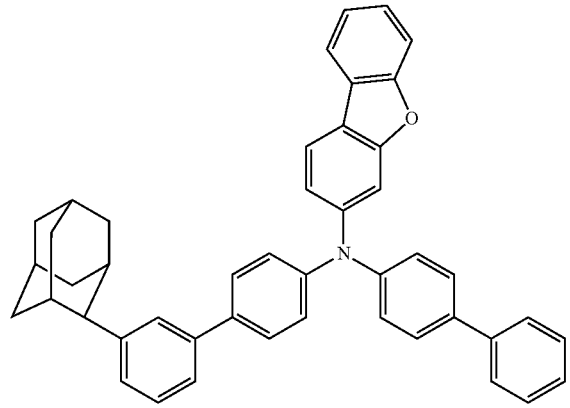
39
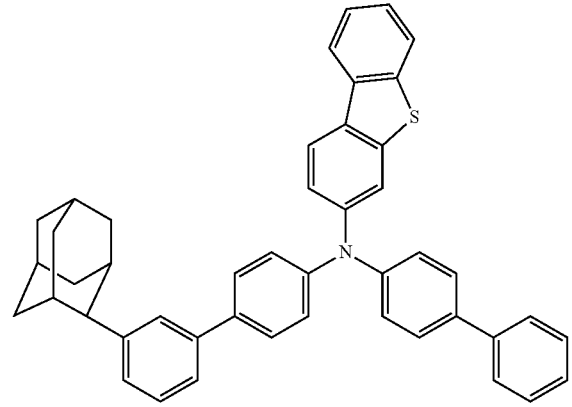
40
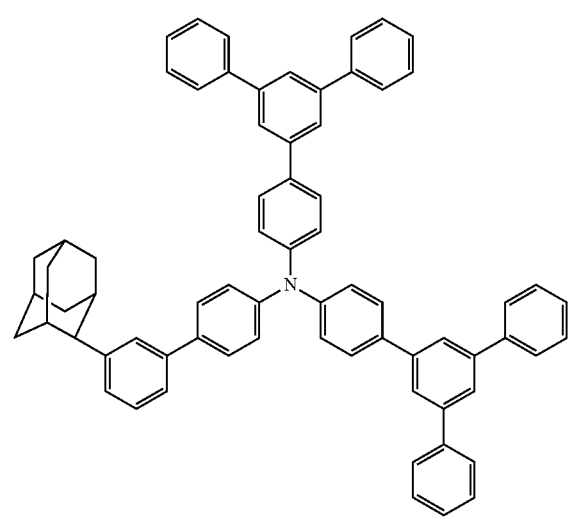
41
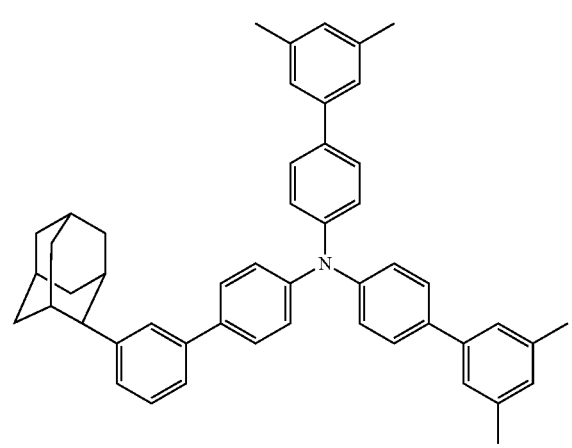

42
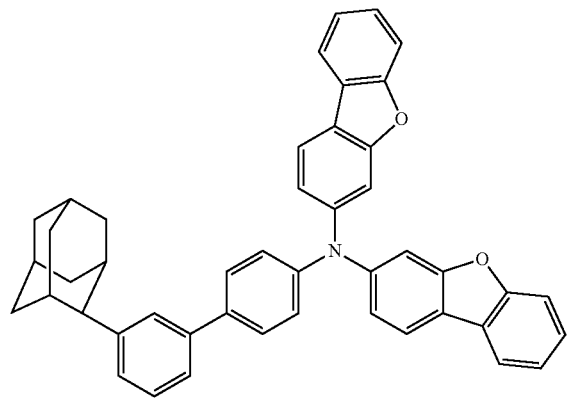
43
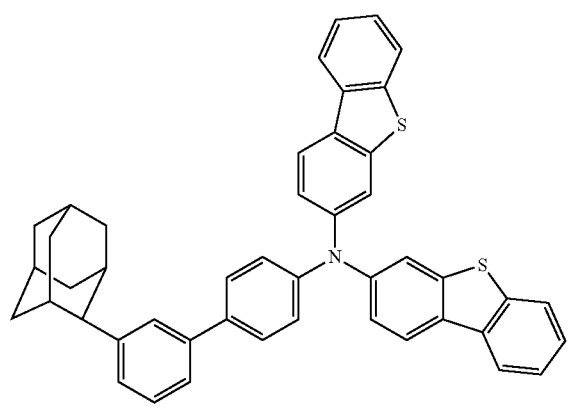
44
45
46
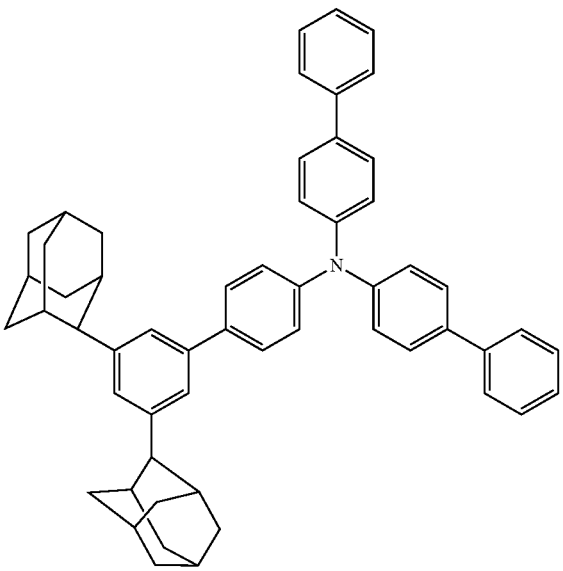
47
48
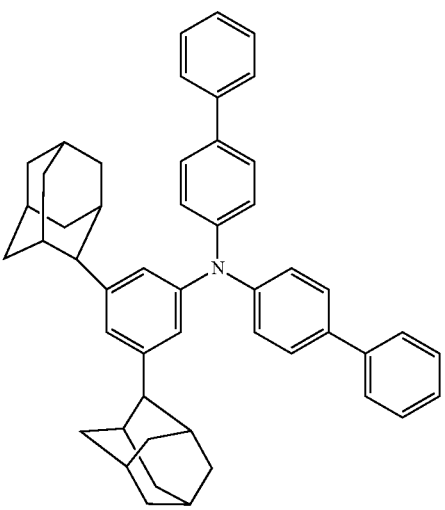
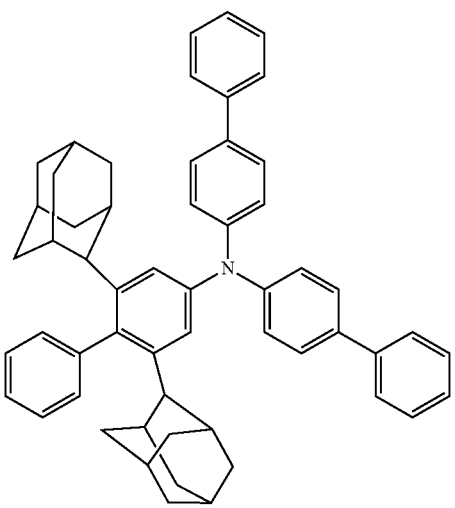

175
-continued
49
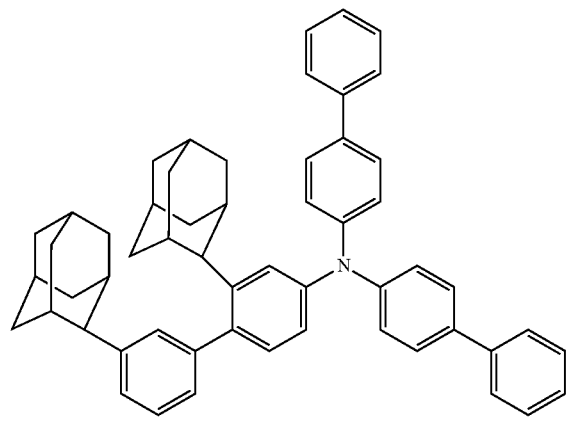
50
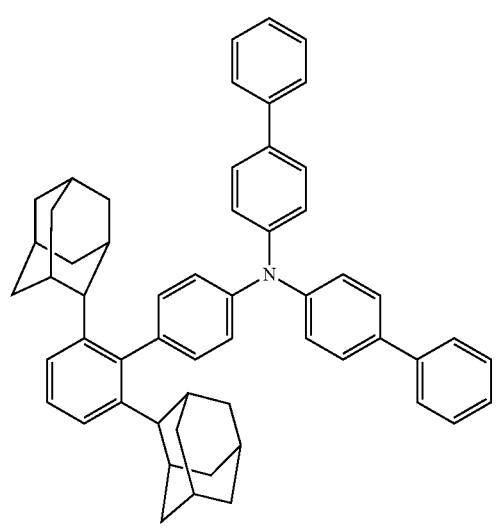
51
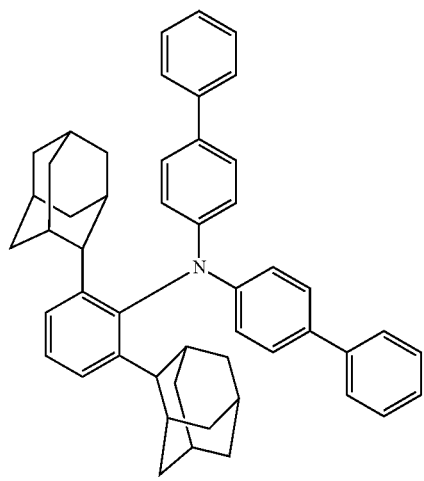
176
-continued
52
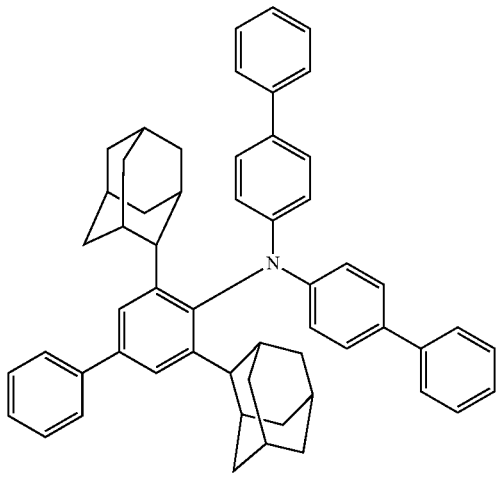
53
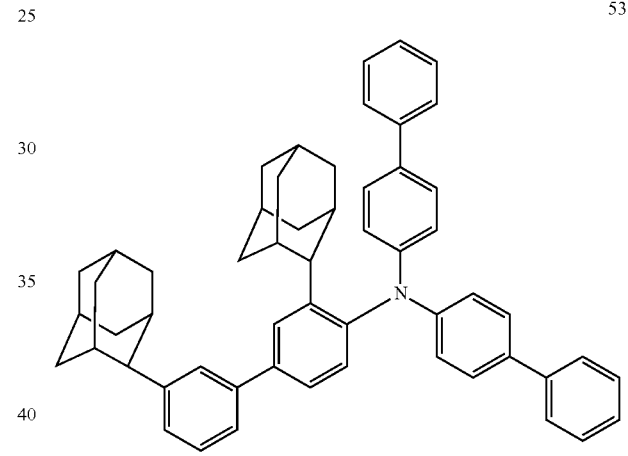
54
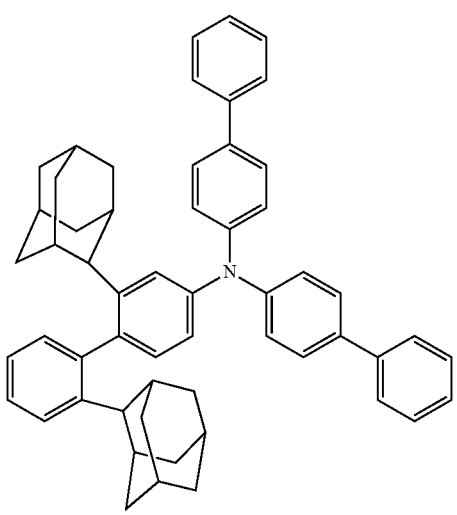

55
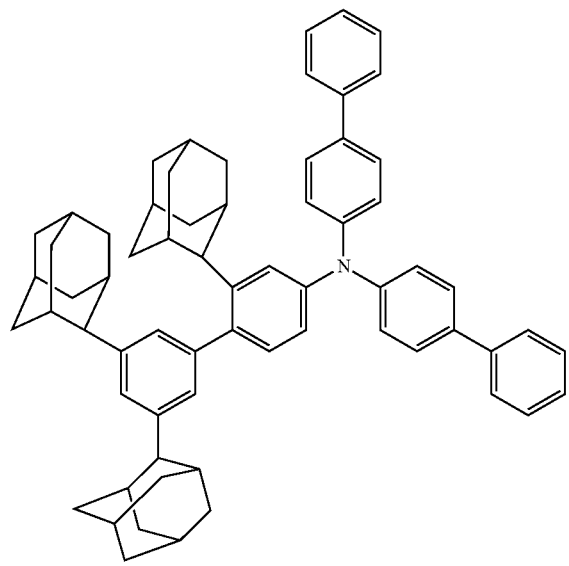
56
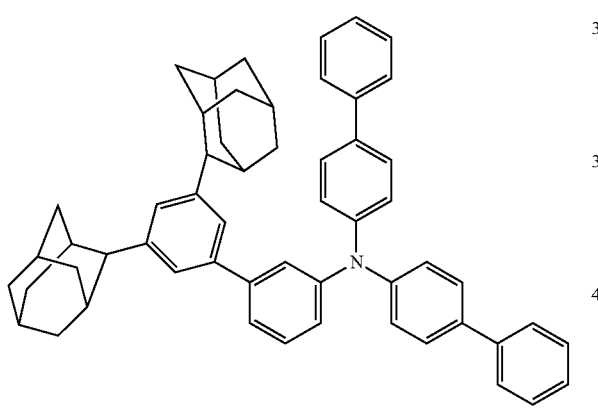
57
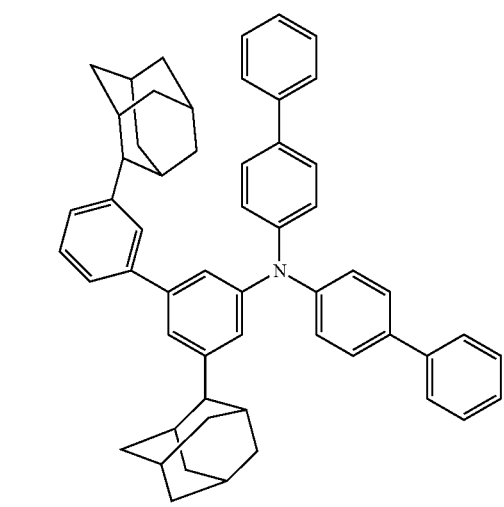
58
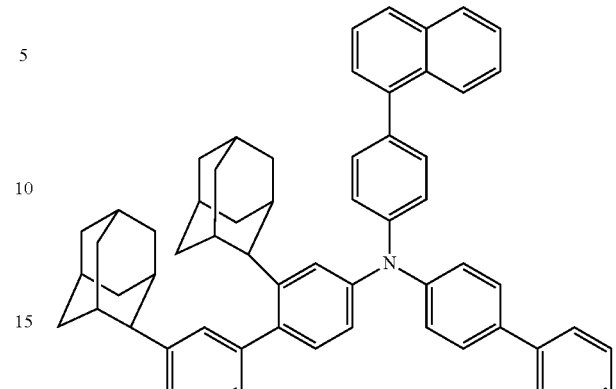
59
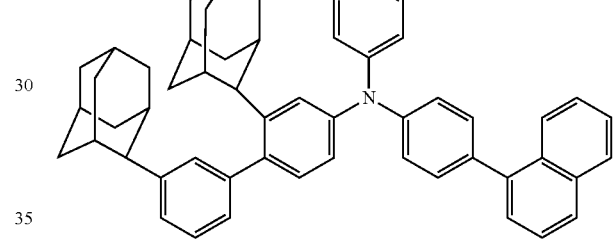
60
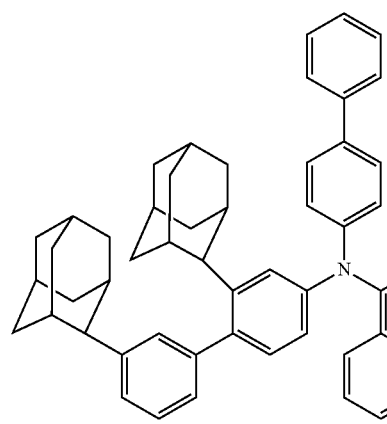
61
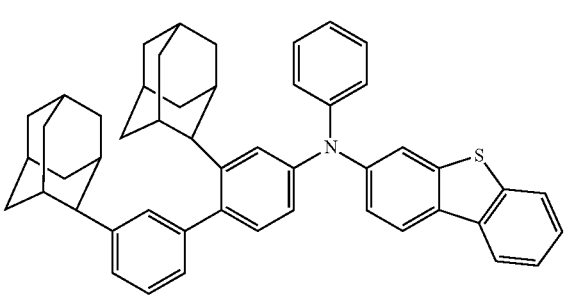

179
-continued
62
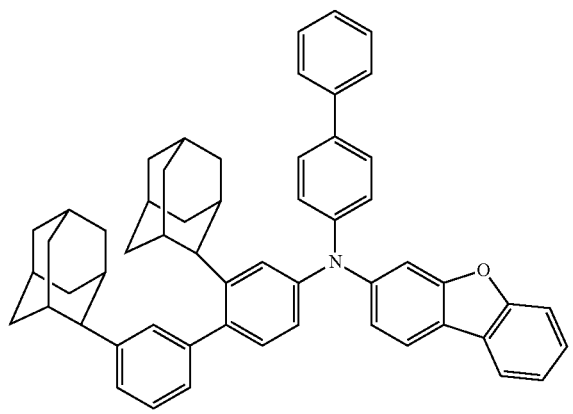
63
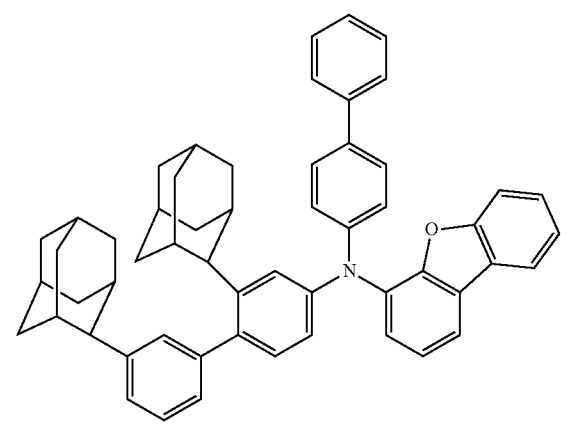
64
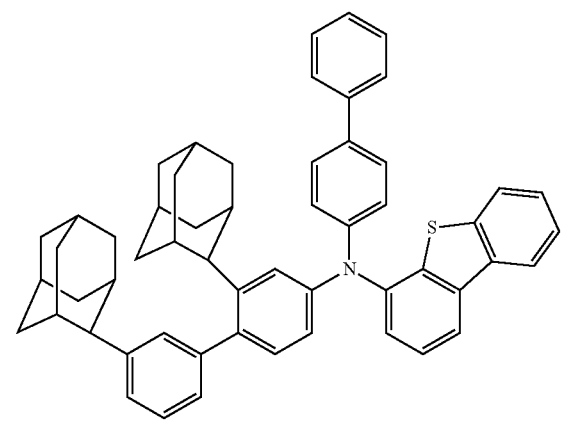
180
-continued
65
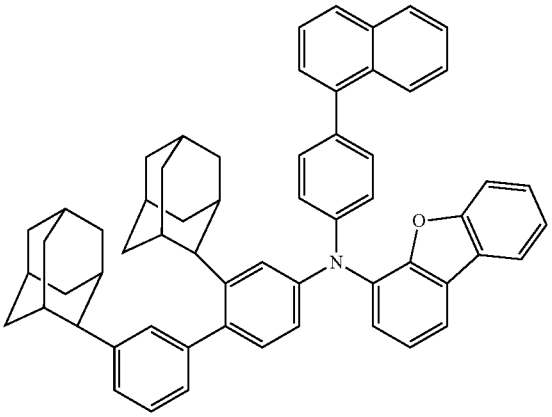
66
67
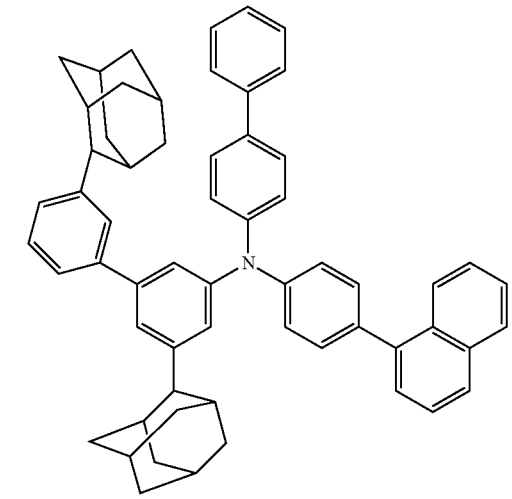

68
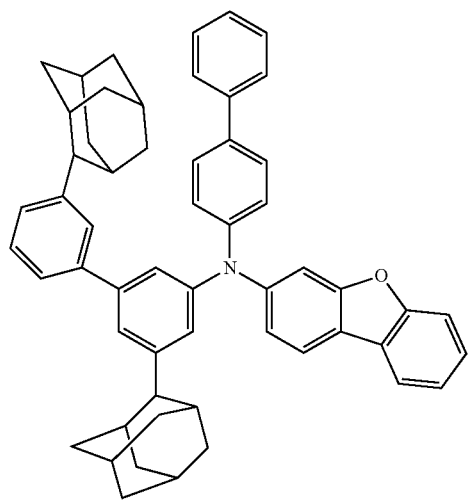
69
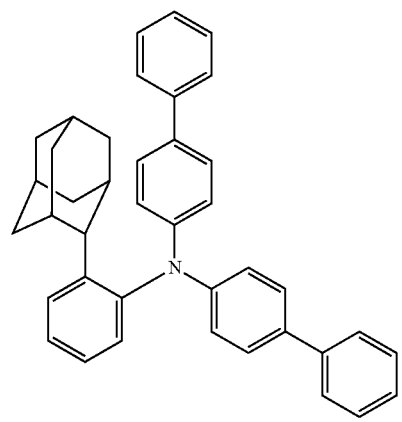
70
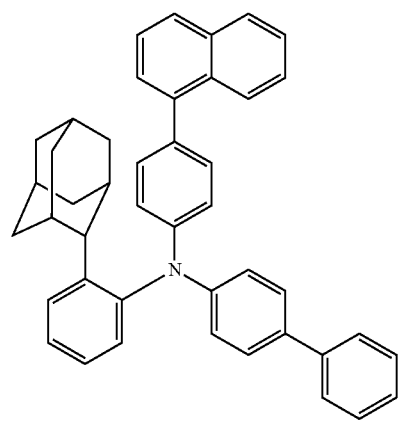
71
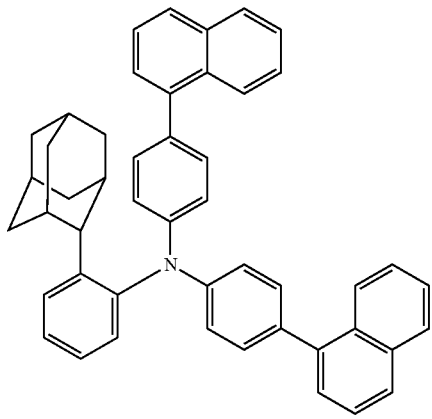
72
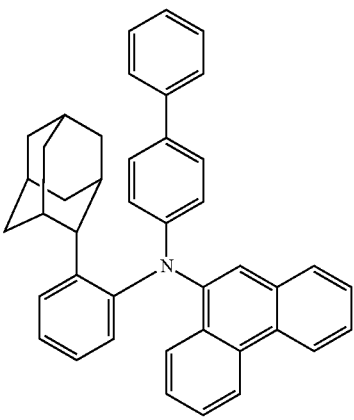
73
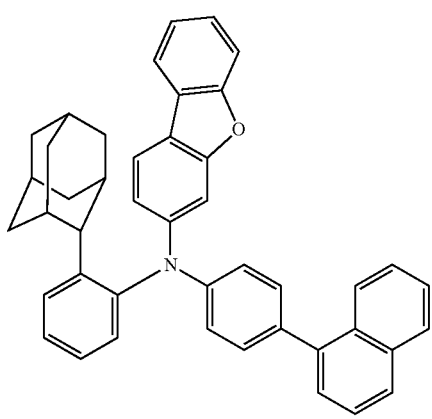

74
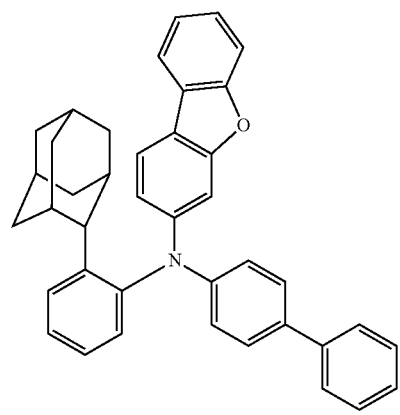
75
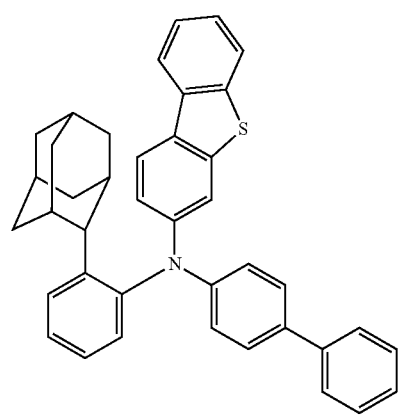
76
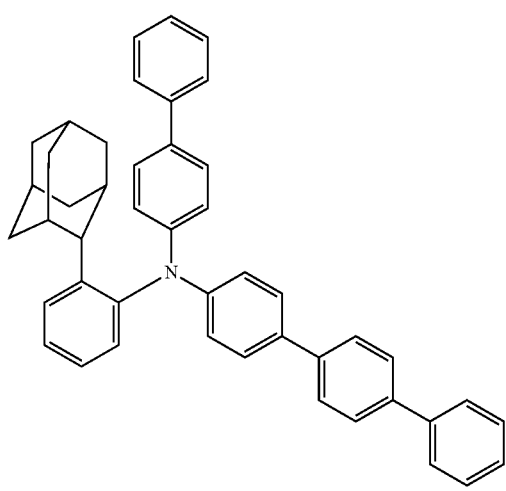
77
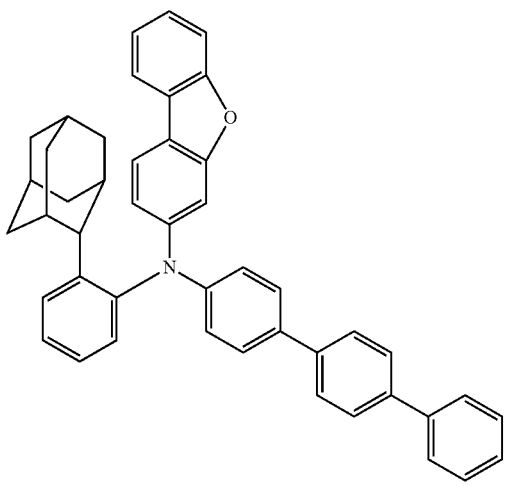
78
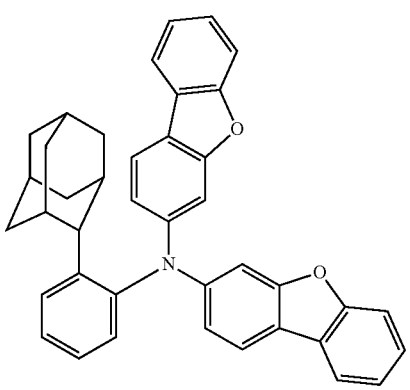
79
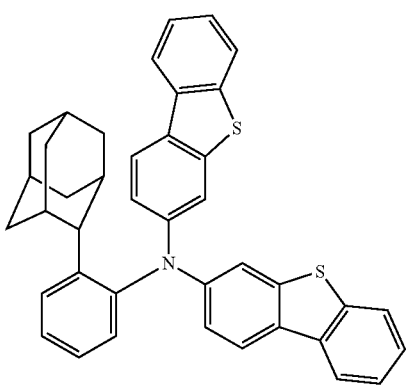
80
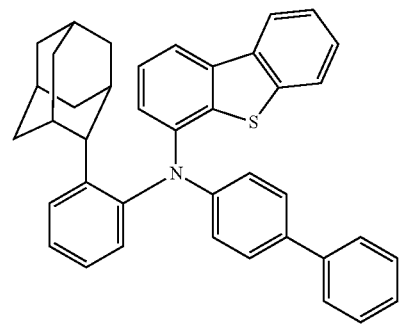

-continued
81
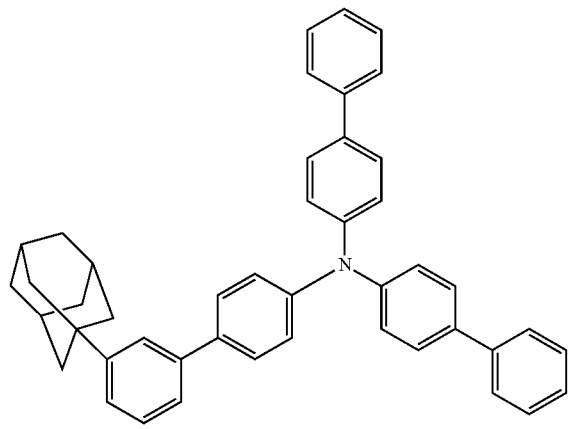
82
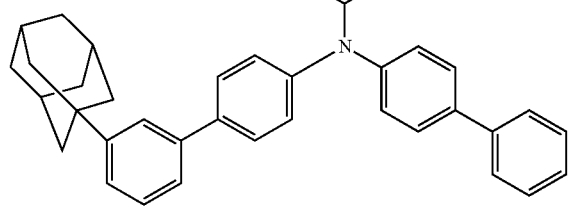
83
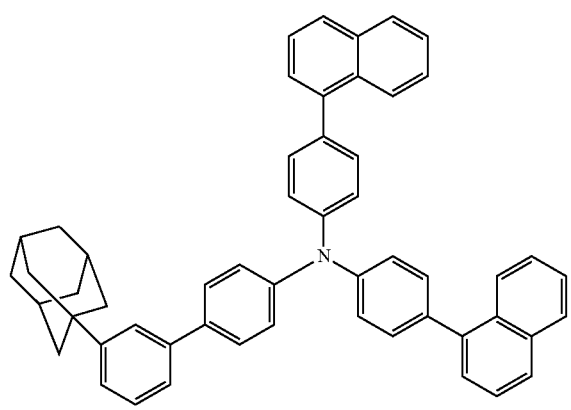
-continued
84
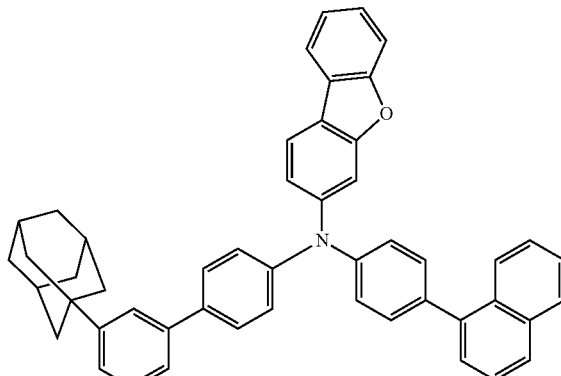
85
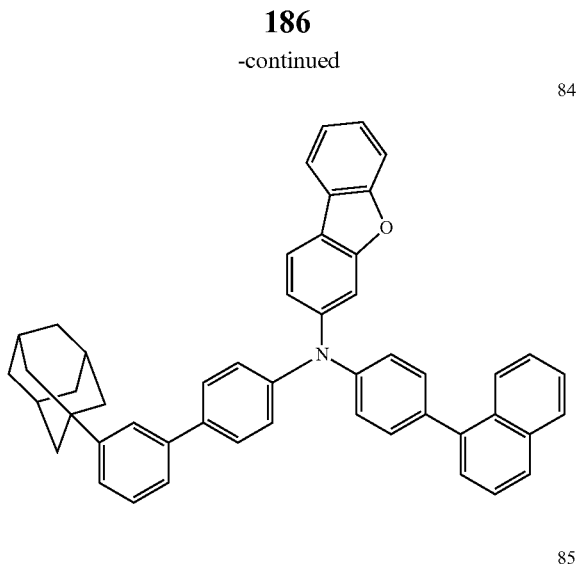
86
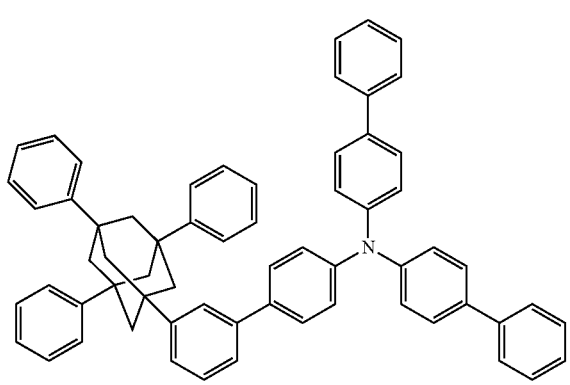
87
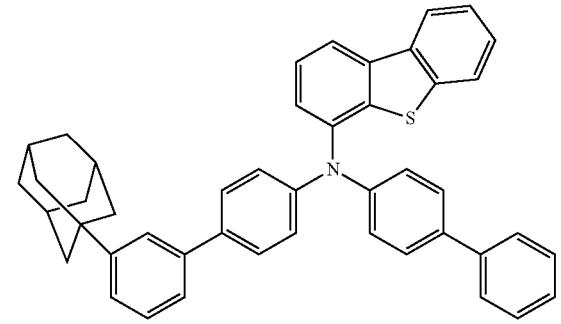

88
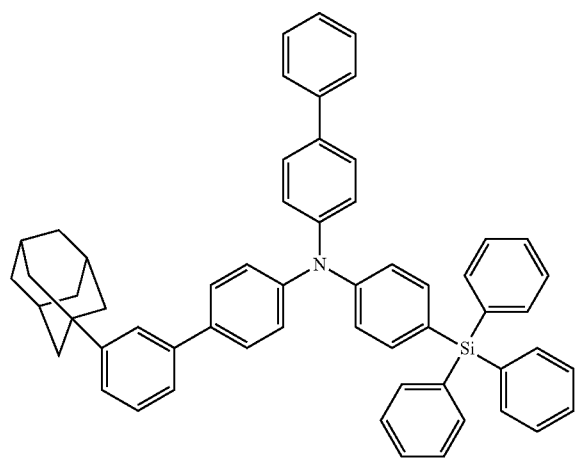
89
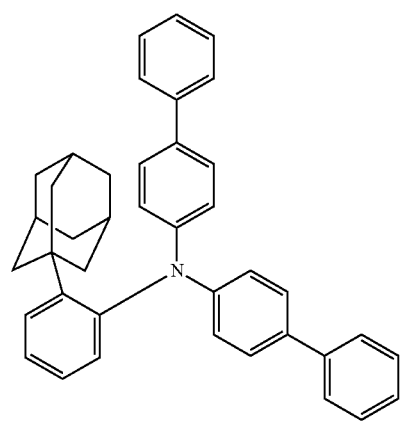
90
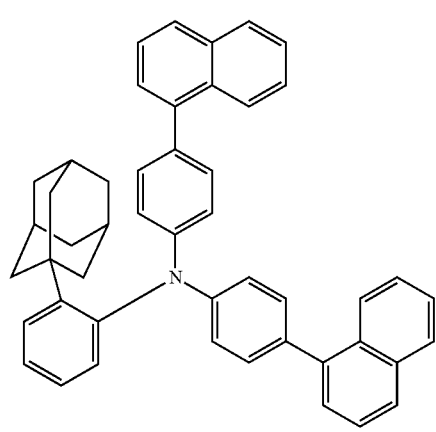
91
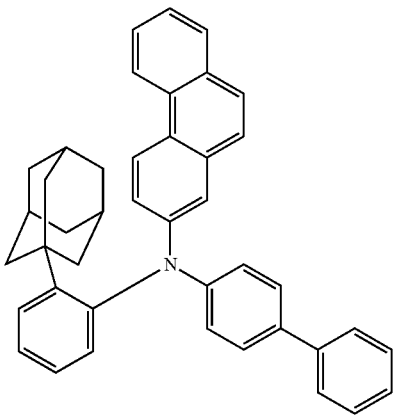
92
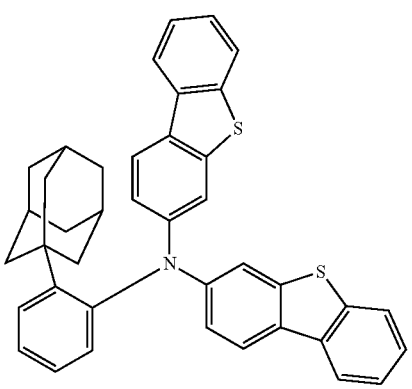
93
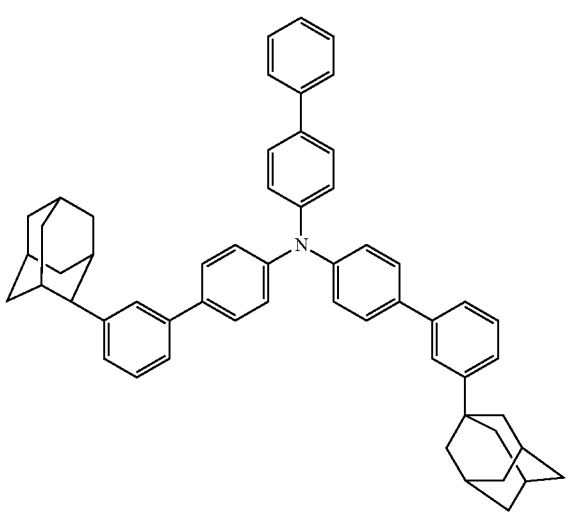

189
190
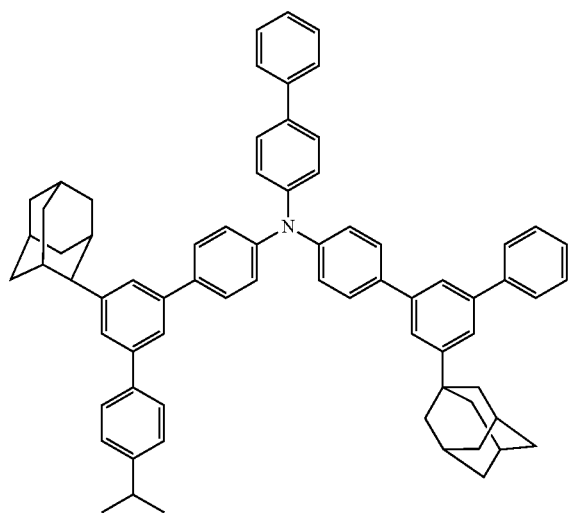
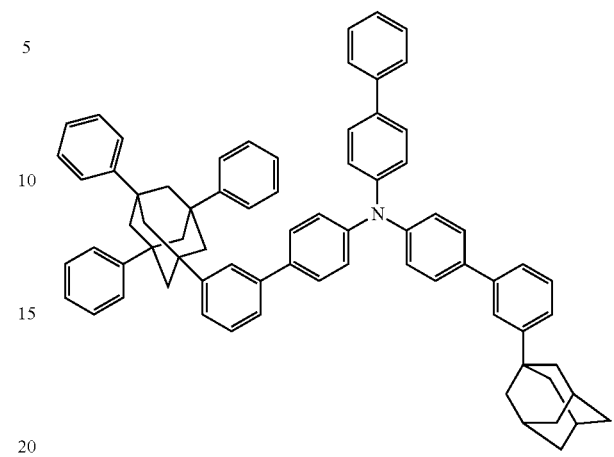
* * * * *

UNITED STATES PATENT AND TRADEMARK OFFICE
CERTIFICATE OF CORRECTION

| | | |
|---|---|---|
| PATENT NO. | : 11,038,111 B2 | |
| APPLICATION NO. | : 16/200412 | |
| DATED | : June 15, 2021 | |
| INVENTOR(S) | : Ichinori Takada et al. | |

It is certified that error appears in the above-identified patent and that said Letters Patent is hereby corrected as shown below:

In the Claims

Column 120, Line 3, Claim 6      Delete ""b", "b"," and
Insert -- "b", --

Column 154, Lines 29-30, Claim 13      Delete ""b", "b"," and
Insert -- "b", --

Signed and Sealed this
Second Day of August, 2022

Katherine Kelly Vidal
*Director of the United States Patent and Trademark Office*